(12) United States Patent
Mirochnitchenko et al.

(10) Patent No.: US 9,382,310 B2
(45) Date of Patent: Jul. 5, 2016

(54) **EXPRESSION OF TRIPLE-HELICAL COLLAGEN-LIKE PRODUCTS IN *E. COLI***

(75) Inventors: Oleg Mirochnitchenko, Rockville, MD (US); Masayori Inouye, New Brunswick, NJ (US); Barbara Brodsky, Brookline, MA (US); John Ramshaw, Pascoe Vale (AU)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/148,066

(22) PCT Filed: Feb. 5, 2010

(86) PCT No.: PCT/US2010/023318
§ 371 (c)(1),
(2), (4) Date: Dec. 23, 2011

(87) PCT Pub. No.: WO2010/091251
PCT Pub. Date: Aug. 12, 2010

(65) Prior Publication Data
US 2012/0116053 A1 May 10, 2012

Related U.S. Application Data

(60) Provisional application No. 61/150,375, filed on Feb. 6, 2009.

(51) Int. Cl.
C07K 14/48 (2006.01)
A61K 38/39 (2006.01)
C07K 14/78 (2006.01)

(52) U.S. Cl.
CPC .................................... C07K 14/78 (2013.01)

(58) Field of Classification Search
CPC ............... C07K 14/78; C07K 2319/01; C07K 2319/50; A61K 38/39
See application file for complete search history.

(56) References Cited

U.S. PATENT DOCUMENTS

| | | | |
|---|---|---|---|
| 6,110,689 A | 8/2000 | Qvist et al. | |
| 6,953,839 B2 * | 10/2005 | Hook et al. | 530/356 |
| 2003/0148944 A1 | 8/2003 | Holmdahl et al. | |
| 2003/0220245 A1 | 11/2003 | Hubbell et al. | |
| 2004/0214282 A1 | 10/2004 | Hook et al. | |

OTHER PUBLICATIONS

Ferretti et al. 2001; Complete genome sequence of an M1 stain of *Streptococcus pyrogenes*. PNAS. 98(8): 4658-4663.*
Brazel et al. 1987; Completion of the amino acid sequence of the alpha 1 chain of human basement membrane collagen (type IV) reveals 21 non-triplet interuptions located within the collagen domain. European Journal of Biochemistry. 168: 529-536.*
Emsley et al. 2000; Structural basis of collagne recognition by integrin alpha2beta1. Cell. 101: 47-56.*
Rouslahti 1996; RGD and other recognition sequences for integrins. Annual Review of Cell and Developmental Biology. 12: 697-715.*
Lucas et al. May 2008; Complete sequence of Rhodopseudomonas palustris TIE-1; EMBL ACF02609.*
Copeland et al. Feb. 2008; Complete sequence of chromosome of *Methylobacterium* sp. 4-46. Embl ACA18713.*
Shoulders et al. 2009; Collagen structure and stability. Annual Review of Biochemistry 78:929-958.*
Nakazato, et al. "Gelation of the Lens Capsule Type IV Collagen Solution at a Neutral pH." J. Biochem. 20(5): 889-894. (1996).
Mohs, et al. "Conformational Features of a Natural Break in the Type IV Collagen Gly-X-Y Repeat." JBC 281(25): 17197-17202. (2006).
Konitsiotis, et al. "Characterization of High Affinity Binding Motifs for the Discoidin Domain Receptor DDR2 in Collagen." JBC 283(11): 6861-6868. (2008).
Twardowski, et al. "Type I Collagen and Collagen Mimetics as Angiogenesis Promoting Superpolymers." Current Pharmaceutical Design 13(35): 3608-3621. (2007).
Sumby, et al. "Collagen-Like Surface Protein." Uniprot Direct Submission Q48Z23. Sep. 13, 2005. <<http://www.uniprot.org/uniprot/Q48Z23.html>>. Last accessed Jul. 30, 3010.
Lucas, et al. "Collagen Triple Helix Repeat." Uniprot Direct Submission B3QFU6. Sep. 2, 2008. <<http://www.uniprot.org/uniprot/B3QFU6.html>>. Last accessed Jul. 30, 3010.
Dolz, et al. "Folding of Collagen IV." Eur. J. Biochem. 178(2): 357-366. (1988).
Han, et al. "Assessment of Prokaryotic Collagen-Like Sequences Derived from *Streptococcal* Scl1 and Scl2 Proteins as a Source of Recombinant GXY Polymers." Appl. Microbiol. Biotechnol. 72(1): 109-115. (2006).

* cited by examiner

*Primary Examiner* — Karen Cochrane Carlson
(74) *Attorney, Agent, or Firm* — Fox Rothschild LLP

(57) ABSTRACT

Recombinant bacterial triple-helical collagen-like proteins comprising two or more repetitive sequences of Gly-Xaa-Yaa yielding high-stability polymeric constructs without the need for post-translational modifications and which may incorporate one or more functional domains of biological or structural importance. The polymers are capable of high-yield production for a variety of applications.

30 Claims, 18 Drawing Sheets a.
V-CL
V-CL-CL
b.
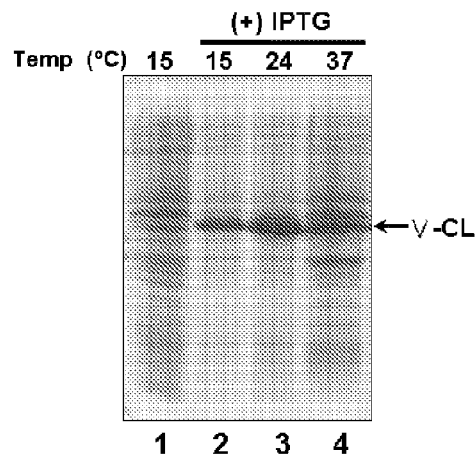
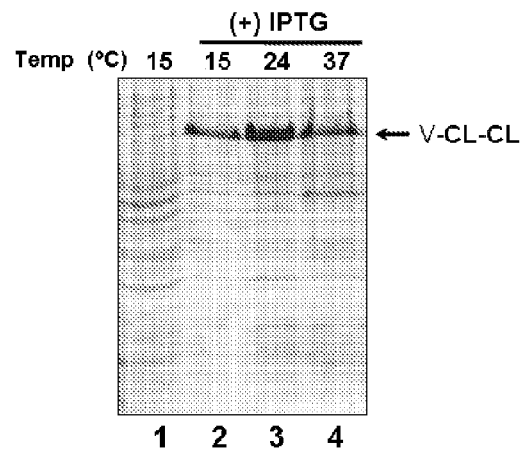
Fig. 6A and 6B

Monomer

Dimer

A.

B.

C.

D.

EXPRESSION OF TRIPLE-HELICAL COLLAGEN-LIKE PRODUCTS IN *E. COLI*

CROSS-REFERENCE TO RELATED APPLICATION

The instant application is the U.S. National Phase of International Patent Application Serial No. PCT/US10/23318, filed Feb. 5, 2011, which claims priority under 35 U.S.C. §119(e) to U.S. Provisional Patent Application Ser. No. 61/150,375, filed Feb. 6, 2009, the contents of which are incorporated herein by reference in their entireties.

STATEMENT REGARDING FEDERALLY SPONSORED RESEARCH OR DEVELOPMENT

This invention was produced in part using funds obtained through grant EB007198 from the National Institutes of Health. The federal government may have certain rights in this invention.

FIELD OF THE INVENTION

The present invention relates to a modular, recombinant collagen-like protein that is stable at mammalian bodily temperatures, either in its native state or after chemical cross-linking, and aggregating the protein for use in a wide range of applications.

BACKGROUND OF THE INVENTION

Collagen is a key player in human development, maintenance of health, and a range of common and uncommon diseases. It is considered to be the characteristic structural molecule of the extracellular matrix in multicellular animals. Fibril-forming collagens and basement membrane collagens are ubiquitous in vertebrates and invertebrates, whereas families of more specialized collagens have developed in different organisms.

The collagen structure is defined by the distinctive supercoiled triple-helix conformation, having a $(Gly-Xaa-Yaa)_n$ amino acid sequence. In this configuration, Gly provides a glycine residue with Xaa and Yaa independently comprising any known imino or amino acid residue for each repeat unit. Unique properties of the collagen triple-helix motif include its molecular hydrodynamic properties, extensive hydration, ability to bind diverse ligands, and capacity to self-associate to form fibrils and other higher order structures. These distinctive features have been exploited by nature to fill a wide range of structural and functional niches. For example, in humans, characteristic collagen fibrils with an axial D=67 nm period provide the structural backbone of tendons, skin, bone, cartilage, and other connective tissues. A network-like structure of type IV collagen is also important for basement membranes, such as those in the kidney glomerulus and lining of blood vessels.

A high content of hydroxyproline (Hyp) is a unique stabilizing feature found within most animal collagens. Indeed, it is widely believed that Hyp residues stabilize the collagen helical structure so it will not denature when exposed to mammalian body temperatures. Hyp residues are typically formed from the post-translational modification of proline residues at the Yaa positions by the enzyme prolyl hydroxylase. Once modified, Hyp confers a thermal stability that has been shown to be much greater than that conferred by Pro residues, or any other imino or amino acid, alone. Indeed, previously evaluated collagens without any Hyp have been found to be unstable when exposed to mammalian bodily temperatures.

There have been numerous attempts to design biomaterial products utilizing isolated animal-derived collagen. Such products, while functional, give rise to increasing concerns including the risk of contamination by infectious agents, as well as product standardization. Moreover, animal-derived collagen is limited in that extracted collagens cannot be designed to enhance or modify specific biological properties. Accordingly, attention has shifted away from isolation of animal collagen and toward production of recombinant collagens produced within micro-organism models.

Production of recombinant collagen in an industrial quantity has been very difficult because bacterial hosts lack the biological mechanisms for the post-translational modification of proline residues to hydroxyprolines. Notwithstanding, potentially useful triple-helix-containing collagen-like proteins have been identified in a number of bacteria in recent years. In several pathogenic bacteria, collagen-like proteins have been shown to be expressed and to form stable triple-helical proteins which play a role in pathogenicity. For example, Scl1 and Scl2 proteins from bacterium group A *Streptococcus pyogenes* (GAS) are expressed on the bacterial cell surface, and are thought to mediate GAS internalization by human cell. Even without post-translational modification of proline, Scl1 and Scl2 have been shown to form heat stable triple-helical structures when expressed as recombinant proteins, particularly when expressed with an amino-terminal globular domain ($V_{Sp}$). Other prokaryotic collagen-like have also been characterized and include *Bacillus cereus* and *Bacillus anthracis* proteins associated with the exosporium with a probable role in spore-host interactions; pneumococcal collagen-like protein A (PclA) contributing to adhesion and invasion of host cells; and a family of seven collagen-like proteins, called SclC-SclI from *Streptococcus equi* subspecies, which are expressed upon infection of horses leading to the pathological condition known as strangles.

These bacterial collagen-like proteins offer an opportunity to create stable triple-helix protein products in a high yield bacterial expression system. The bacterial origin of the collagen-like protein ensures compatibility in the bacterial expression system in terms of codon usage and other factors. Beyond the previously identified sequences, a collagen product is desirable that can easily be produced by recombinant methods on a large scale, while providing greater heat stability, the ability refold in vivo after denaturation, and improving the biological use of the final product. Such collagens, could potentially be aggregated and would be used to make various products, to include biomaterials. As provided herein, the present invention addresses the foregoing needs.

SUMMARY OF THE INVENTION

The present invention relates to a modular, recombinant collagen-like protein structure which is stable at mammalian bodily temperatures (i.e. between 35-40° C.), in its native form or after stabilization by chemical cross-linking, comprising the formula I:

$$[(Gly\text{-}Xaa\text{-}Yaa)_m\text{-}(insert)_n]_p$$

where m is between about 1 to 200 and $(Gly\text{-}Xaa\text{-}Yaa)_m$ represents a bacterially produced triple helical domain with Xaa and Yaa being independently any natural or unnatural imino or amino acid for each repeat unit. In further non-limiting embodiments, neither Xaa nor Yaa is a hydroxyproline. The insert is comprised of about 1 to 50 of any imino or amino acids, with n being 0 or 1, and p being any number from about 2 to about 10 wherein the value of n is unique for each repeat and at least one insert is provided in the collagen-like protein.

The overall content of Xaa and Yaa provides a proline rich structure where the total percentage of proline of all residues in the Xaa and Yaa positions is greater than 19%, but optimally, though not exclusively, between 19.5-40%. Alternatively, or in conjunction with the proline concentration, the triple helical motif may also contain a concentration of charged residues (e.g. Asp, Glu, Lys, Arg, His) of greater than 14% and optimally, though not exclusively, between 14-35%. Such domains should also aggregate, either naturally or synthetically, at a neutral pH or otherwise using one or a variation of such protocols discussed herein or otherwise known in the art.

The triple helical domains may be isolated from one or multiple pathogenic or non-pathogenic bacterial organisms. By way of example, the triple helical domains can include domains derived from *Streptococcus pyogenes, Clostridium perfringens, Methylobacterium* sp. 4-46, *Solibacter usitatus* Ellin6076 or *Rhodopseudomonos palustris* tie-1, which exhibit the desired heat stability in either its native state or after stabilization by chemical cross-linking. Such sequences may include those identified herein as SEQ ID NOS: 7-11 or similar triple helical collagen-like sequences identified in U.S. Pat. No. 6,953,839, the contents of which are incorporated herein by reference. Alternatively, each triple helical domain may include repeats, fragments, homologues or combinations of the foregoing peptide sequences.

The insert sequences may be adapted to improve the bendability or elasticity of the biomaterial or otherwise serve as a natural binding domain or biological cleavage sequence. Natural breaks or interruption sequences, for example, may include those of non-fibrillar human collagens, which are typically provided as 1 to 50 amino acids spaced between two glycine residues. While the instant invention is not so limited, examples of such sequences include those provided below by SEQ ID NOS: 12-14, 16, 17, 50, and 65 as well as repeats, fragments, homologues or combinations thereof.

The insert regions may also, or alternatively, include at least one integrin binding site or other cell binding sites (e.g. DDR2 sites), or combinations thereof. Examples of such integrin domains include, but are not limited to, one or more of the sequences identified in SEQ ID NO: 15 or 18, as well as repeats, fragments, homologues or combination thereof. An example of such a DDR2 domain includes, but is not limited to, SEQ ID NO.: 78.

In even further embodiments, the insert regions may also, or alternatively, include at least one matrix metalloproteinase cleavage site. Examples of such domains include, but are not limited to, one or more of the sequences identified in SEQ ID NOS: 19-28, 62, and 67-75, as well as repeats, fragments, homologues or combination thereof.

To facilitate the proper formation of the triple helical structure, the recombinant protein of the instant invention may also be expressed with non-collagenous folding domain bound at either or both its amino terminus end or a carboxy terminus end. An example of a non-collagenous domain derived from bacterial origin that provides helical folding when bound to the N-terminus of the protein includes SEQ ID NO: 47. An example of a non-collagenous domain derived from bacterial origin that provides helical folding when bound to the C-terminus of the protein includes SEQ ID NO: 51. The instant invention, however, is not so limited and may also include similar or otherwise homologous globular proteins, coiled-coil forming sequences, C-propeptide domains or foldons found in the microorganisms discussed herein, artificially produced, or otherwise known in the art to assist with helical folding.

In another embodiment the instant invention provides a biological aggregate for use in a biomedical product where the aggregates are made from recombinant bacterial collagen-like protein structure that is stable at mammalian bodily temperatures, either in its native state or after stabilization by chemical cross-linking, and may be represented by the formula

$$[(Gly\text{-}Xaa\text{-}Yaa)_m\text{-}(insert)_n]_p$$

where m is between about 1 to 200 and $(Gly\text{-}Xaa\text{-}Yaa)_m$ represents a triple helical domain with Xaa and Yaa independently being any natural or unnatural imino or amino acid for each repeat unit. The insert is comprised of about 1 to 50 of any imino or amino acids, with n being 0 or 1, and p being any number from about 2 to about 10, wherein the value of n is unique for each repeat and at least one insert is provided in the collagen-like protein. Also, optionally, a non-collagenous domain bound to the protein at either or both an amino terminus end or a carboxy terminus end, which facilitates protein folding of the triple helical domain.

The biological aggregate may be utilized in biomedical products including, but not limited to, soluble recombinant collagens, such as for use in dermal implants, drug carriers, plastic coatings for medical devices, implant coatings (orthopedic and vascular), shape-formation materials, viscosurgery, vascular sealants, cosmetics, and regulators of enzymes activity (e.g., metalloproteinases); sponge-like materials, such as for use in three-dimensional cell cultures, tissue and organ engineering, hemostatic agents, and wound therapy (artificial skin and wound dressings); fibers, such as for use in surgical sutures and hemostatic agents; gel-like materials, such as for use in tissue implants, corneal shields, contact lens, and matrices for cell culture; and membrane-like materials, such as for use in anti-adhesion membranes, drug delivery systems, artificial skin, and the like. Additionally, the aggregate may be used outside of the biomedical arena with industrial applications including, but not limited to, the following: leather industry applications, stabilizers, thickeners in glue manufacture, emulsifiers, foaming agents suitable for paper or textile manufacture, photographic films, manufacture of rubber substitutes, food industry applications, and the like.

Methods of producing a recombinant collagen-like protein include isolating 2 or more nucleic acid sequences each encoding separate triple helical domains formed from repeat sub-units of the formula $(Gly\text{-}Xaa\text{-}Yaa)_m$, as defined above. Two or more isolated sequences are inserted into a single nucleic acid vector and expressed using standard methods that are generally known in the art. In one non-limiting example, two or more triple helical domains are inserted within the vector and optionally one or more non-collagen insert sequences encoding 1 to about 50 amino acids are spaced between the isolated sequences. Additionally, a non-collagenous domain nucleic acid sequence which facilitates protein folding of the triple helical domain upon expression may be provided at either or both an amino terminus end or a carboxy terminus end of a triple helical domain. One end of the sequence is then labeled with a sequence tag and cloned into a micro-organism. While not limited thereto, the expression vector may be a cold shock vector and the recombinant protein may be expressed in the microorganism (e.g. *E. coli*) at temperatures below 37° C., and in certain embodiments at temperatures of about 15-23° C. The resulting expression product is then isolated, purified, and processed to result in aggregate formation, which may be used as one or more of the biomaterials provided herein. One of ordinary skill in the art will appreciate, however, that the methods of producing the instant invention are not limited to the foregoing and that a range of other microbial expression systems could also be used including both bacterial and yeast expression systems otherwise known in the art or taught herein.

BRIEF DESCRIPTION OF THE FIGURES

FIG. 6A provides a schematic of the design of the bacterial collagen Scl2.28 chimeric construct, showing the $V_{Sp}$-$CL_{Sp}$ and $V_{Sp}$-$CL_{Sp}$-$CL_{Sp}$ constructed with a His6 tag at the N-terminal end and a thrombin/trypsin cleavage sequence (LVPRGSP) between the $V_{Sp}$ domain and collagen-like domain ($CL_{Sp}$).

FIG. 6B provides an SDS-PAGE of cell extracted after expression wherein $V_{Sp}$-$CL_{Sp}$ and $V_{Sp}$-$CL_{Sp}$-$CL_{Sp}$ were expressed in E. coli BL21 strain.

DETAILED DESCRIPTION OF THE INVENTION

Figure 1:
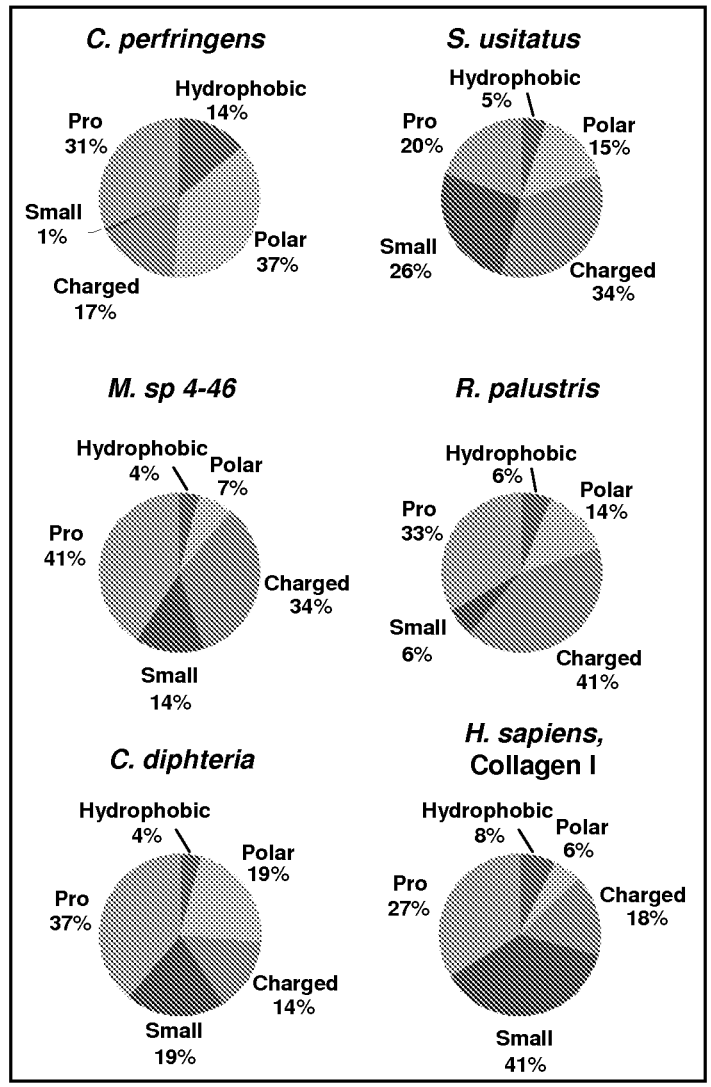
FIG. 1 provides a pie chart representation of the non-Gly residue composition of the bacterial collagen-like domains identified.

The present invention relates to modular collagen-like sequences that are heat stable at mammalian bodily temperatures and are useful as a biomaterial. The collagen-like protein of the instant invention is comprised of two or more triple helical domains each optionally separated by a non-collagen-like insert region. The insert regions may be adapted to mimic natural breaks in the triple helical structure that are found within many human collagens or may provide a desired biological functionality (e.g. cell/tissue binding or protease cleave site) to the biomaterial. To ensure proper folding of triple helical region both post-translationality and post-denaturation, the recombinant collagen-like protein of the present invention is optionally expressed with a globular folding domain at either or both its N-terminus or C-terminus. The resulting chimeric protein is then able to naturally form higher-order fibril-like or aggregate structures, which may be processed for use in a wide multitude of applications.

The recombinant collagen-like structure of the instant may be represented by the following formula I:

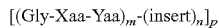

$$[(Gly\text{-}Xaa\text{-}Yaa)_m\text{-}(insert)_n]_p$$

where p is any number from about 1 to about 10, and is in certain embodiments at least 2. $(Gly\text{-}Xaa\text{-}Yaa)_m$ represents the collagen triple helical domain where Gly is a glycine, and Xaa and Yaa are independently comprised of any imino or amino acid, which are unique at each repeat along the length of the triple helical motif. M is comprised of any number from about 1 to about 200 and is, in certain embodiments, between 35 and 200. As illustrated in the Examples below, the triple helical motifs of the instant invention are heat stable at mammalian bodily temperatures (e.g. 35-40° C.), either in its native state or after stabilization by chemical cross-linking, and do not require secondary posttranslational modification of any amino or imino acids for stability. To this end, in certain non-limiting embodiments, Hyp residues are not provided in the instant structures.

In one embodiment, heat stable triple helical domains may be identified from pathogenic or non-pathogenic bacterial organisms based upon proline and charged amino acid concentrations of the targeted moieties. Specifically, the triple helical structure is preferably proline rich having a total percentage of proline of all residues in the Xaa and Yaa positions of greater than 19% and optimally, though not exclusively, between 19.5-40%. Alternatively, however, the triple helical motif may be comprised of charged residues (e.g. Asp, Glu, Lys, Arg, His) in a concentration of greater than 14% and optimally, though not exclusively, between 14-35%. Examples of such heat stable triple helical domains include the sequences, fragments, homologues or combinations obtained from the organisms Streptococcus pyogenes, Clostridium perfringens, Methylobacterium sp. 4-46, Solibacter usitatus Ellin6076 or *Rhodopseudomonos palustris* tie-1, which have the following peptide sequences:

| Organism | Sequence |
|---|---|
| *Streptococcus pyogenes* | GSPGLPGPRGEQGPTGPTGPAGPRGLQGLQGLQGERGEQGPTGPAGPRGLQ GERGEQGPTGLAGKAGEAGAKGETGPAGPQGPRGEQGPQGLPGKDGEAG AQGPAGPMGPAGERGEKGEPGTQGAKGDRGETGPVGPRGERGEAGPAGK DGERGPVGPAGKDGQNGQDGLPGKDGKDGQNGKDGLPGKDGKDGQNGK DGLPGKDGKDGQDGKDGLPGKDGKDGLPGKDGKDGQPGKPGKY (SEQ ID NO: 7) |
| *Clostridium perfringens* | GPRGPRGPQGEQGPQGERGFTGPQGPVGPQGEQGPQGERGFTGPQGPIGLQ GEQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQGAT GPQGPQGPVGPQGNQGPIGPQGPVGPQGPQGQPGVN (SEQ ID NO: 8) |
| *Methylobacterium* sp. 4-46 | GLPGPKGDPGPQGPAGPKGEPGPKGEPGPKGEPGPKGEPGPKGEPGPKGEP GPKGEPGPKGEPGPRGEAGPQGALGPKGEAGSRGEPGPRGEPGPKGEAGL AGAPGPKGEAGPRGPQGERGPPGAPGAA (SEQ ID NO: 9) |
| *Solibacter usitatus* Ellin6076 | GPAGPAGPQGPAGPAGAQGPAGPAGPQGPAGPQGSAGAQGPKGDTGAAG PAGEAGPKGETGAAGPKGDTGAAGPAGPKGDTGAAGPAGPKGDTGAAGA TGPKGEKGETGAAGPKGDKGETGAAGPKGDKGETGAAGPKGEKGETGAV GPKGDKGETGAAGPKGDRGETGAVGPKGDKGETGAVGPKGDKGETGAIG PKGDKGDKGDKGDAGVAGPQGIQGVKGDTGLQGPKGDAGPQGAPGTPG GG (SEQ ID NO: 10) |
| *Rhodopseudomonos palustris* tie-1 | GRPGPQGPRGRPGEPGRPGPQGHPGRPGPEGPRGKQGPVGKPGPQGKAGP QGKPGIAGKPGPDGKPGPIGPQGKAGPQGPRGEQGLRGEQGPRGEQGPQGP RGEQGPRGEPGPAGAL (SEQ ID NO: 11) |

These sequences, however, are not limiting to the invention and alternative sequences may be identified from any organism using the criteria provided herein. Organisms from which such sequences could be derived include, but are not to, *Streptococcus pyogenes*, *Clostridium perfringens*, *Methylobacterium* sp. 4-46, *Solibacter usitatus* Ellin6076, *Rhodopseudomonos palustris* tie-1, *Corynebacterium diphtheria*, Actinobacteria (e.g., *Mycobacterium gilvum*, *Mycobacterium tuberculosis*, *Mycobacterium vanbaalenii*, *Nocardioides* species, *Rubrobacter xylanophilus*, *Salinispora arenicola*, *Salinispora tropica*, and *Streptomyces* species), Alphaproteobacteria (e.g., *Anaplasma* species, *Methylobacterium radiotolerans*, *Nitrobacter winogradskyi*, *Paracoccus denitrificans*, *Rhizobium leguminosarum*, *Rhodobacter sphaeroides*, *Rhodopseudomonas palustris*, *Sphingomonas wittichii*, and *Wolbachia* species), Bacteroidetes (e.g., *Bacteroides thetaiotaomicron*), Betaproteobacteria (e.g., *Azoarcus* species, *Burkholderia ambifaria*, *Burkholderia cenocepacia*, *Burkholderia phymatum*, *Burkholderia vietnamiensis*, *Dechloromonas aromatica*, *Polaromonas naphthalenivorans*, *Ralstonia eutropha*, *Ralstonia metallidurans*, *Ralstonia pickettii*, and *Rhodoferax ferrireducens*), Cyanobacteria (e.g., *Cyanothece* species, *Synechocystis* species, *Trichodesmium erythraeum*), Deinococcus (e.g., *Deinococcus radiodurans*), Deltaproteobacteria (e.g., *Anaeromyxobacter dehalogenans*), Epsilonproteobacteria (e.g., *Campylobacter curvus*), Firmicutes (e.g., *Bacillus clausii*, *Bacillus halodurans*, *Bacillus pumilus*, *Bacillus subtilis*, *Clostridium botulinum*, *Clostridium phytofermentans*, *Enterococcus faecalis*, *Geobacillus kaustophilus*, *Lactobacillus casei*, *Lactobacillus plantarum*, *Lactococcus lactis*, *Lysinibacillus sphaericus*, *Staphylococcus haemolyticus*, *Streptococcus agalactiae*, and *Streptococcus pneumoniae*), and Gammaproteobacteria (e.g., *Citrobacter koseri*, *Enterobacter* species, *Escherichia coli*, *Klebsiella pneumoniae*, *Legionella pneumophila*, *Photorhabdus luminescens*, *Pseudomonas aeruginosa*, *Pseudomonas entomophila*, *Pseudomonas putida*, *Psychrobacter cryohalolentis*, *Saccharophagus degradans*, *Salmonella enterica*, *Salmonella typhimurium*, *Serratia proteamaculans*, *Shewanella amazonensis*, *Shewanella baltica*, *Shewanella frigidimarina*, *Shewanella halifaxensis*, *Shewanella loihica*, *Shewanella oneidensis*, *Shewanella pealeana*, *Shewanella putrefaciens*, *Shewanella sediminis*, *Shewanella woodyi*, *Shigella boydii*, *Shigella dysenteriae*, *Shigella flexneri*, *Shigella sonnei*, and *Vibrio harveyi*).

The insert sequences separating each triple helical domain are comprised of a non-collagen peptide sequence of about 1 to 50 imino acid or amino acids. While n is provided as 0 or 1 in formula I, at least one insert is provided in the collagen-like protein. Preferably, although not limited thereto, these sequences improve the bendability or elasticity of the protein and also may provide some biological functionality that is useful for the resulting biomaterial. Bendability may be achieved by providing an insert sequence that mimics natural breaks or interruption sequences often found in non-fibrillar human collagens, e.g. human type IV basement membrane collagens. Such sequences are typically provided as 1 to 50 amino acids spaced between two glycine residues, e.g. Gly-peptide sequence-Gly. While the instant invention is not so limited, examples of such sequences include the following, which are found the alpha domains of form IV, and VII human collagens:

| Break | Sequence |
|---|---|
| G1G | GFG from α5 (IV) |
| G4G | GAAVMG from α5 (IV) (SEQ ID NO: 12) |
| G6G | GDSAVILG from α1 (VII) (SEQ ID NO: 13) |
| G8G | GDMVVSRVKG from α4 (IV) (SEQ ID NO: 14) |
| G9G | GPOGEFYFDLRLKGPOG from α1 (IV) (SEQ ID NO: 50) |

| Break | Sequence |
|---|---|
| G12G | GRLVDTGPGAREKG from α1 (VII) (SEQ ID NO: 16) |
| G15G | GQISEQKRPIDVEFQKG from α5 (IV) (SEQ ID NO.: 65) |
| G41G | GSVPNVDRLLETAGIKASALREIVETWDESSGSFLPVPERRRG from α1 (VII) (SEQ ID NO: 17) |

The desired biological functionality may be derived from sequences that facilitate binding the biomaterial to the targeted cell type or otherwise providing a natural cleavage site for degradation in the body. Binding sequences, for example, may include integrin binding domains such as those identified for α2β1 integrin (e.g. -GFPGER- (SEQ ID NO: 18)) or an α3β1 (e.g. GEFYFDLRLK (SEQ ID NO: 15)). Other sequences include the known type II collagen binding site for DDR2, namely GPRGQPGVMGFP (SEQ ID NO.: 78). In even further embodiments, both the integrin and DDR2 sites are incorporated into the insert region.

Cleavage sequences may include, but are not limited to, one or more sequences within the family of Matrix Metalloproteinase (MMP)s domains, e.g. MMP-1, MMP-2, MMP-8, MMP-13 and MMP-18, which cleave type I, II and III collagens, and MMP-2 and MMP-9, which cleave denatured collagens. Peptide sequences known for achieving such effects include, but are not limited to the following domains:

| | |
|---|---|
| -GPQGIA- | (SEQ ID NO: 19) |
| -GPQGIL- | (SEQ ID NO: 20) |
| -GPQGLA- | (SEQ ID NO: 21) |
| -GPQGLL- | (SEQ ID NO: 22) |
| -GPLGIA- | (SEQ ID NO: 23) |
| -GPLGIL- | (SEQ ID NO: 24) |
| -GPLGLA- | (SEQ ID NO: 25) |
| -GPLGLL- | (SEQ ID NO: 26) |
| -GPRGLQ- | (SEQ ID NO: 27) |
| -GPTGLA- | (SEQ ID NO: 28) |

The present invention, however, is not limited to the foregoing and may include similar sequences otherwise known to achieve such functionality. Such sequences may be provided in tripeptide repeat units of 4, 5, 6, or 8, with optimal cleavage being possible, but not limited to, 5 or 6 tripeptide sequences. Additional examples of such repeat tripeptide sequences include, but are not limited to, the following:

| | |
|---|---|
| GPQGIAGQRGVVGLP | (SEQ ID NO: 62) |
| GPQGLLGAPGILGLP | (SEQ ID NO: 67) |
| GEQGPQGLP | (SEQ ID NO.: 68) |
| GPQGLAGQRGIV | (SEQ ID NO: 69) |
| GAQGPPGAPGPLGIAGITGARGLAGPPGMPGPRGS | (SEQ ID NO: 70) |
| GPLGIAGITGAR | (SEQ ID NO: 71) |
| GAQGPPGAPGPLGIAGITGARGLA- | (SEQ ID NO: 72) |
| GPSGAEGPPGPQGLAGQRGIVGLPGQRGERGFP- | (SEQ ID NO: 73) |
| GPQGLAGQRGIV- | (SEQ ID NO: 74) |
| GPSGAEGPPGPQGLAGQRGIVGLP- | (SEQ ID NO: 75) |

Also important to the stabilizing structure of the collagen-like products of the instant invention is the proper formation of the triple helical structure. While some triple helical domains are able to be formed using the native mechanisms of the expression vehicle, proper folding of the recombinant bacterial collagen-like structure represented by formula I may also be assisted using globular or variable (V) domains. Such globular domains may be expressed directly or indirectly to the N-terminus and/or the C-terminus of the triple helical domain and can facilitate both post-translational folding and refolding following heat denaturation. One non-limiting example of an N-terminus domain is the entirety of or a portion of a variable (V) domain the Scl2 sequence found in *Streptococcus pyogenes*, which may be provided as the following peptide sequence:

(SEQ ID NO: 47)
EENEKVREQEKLIQQLSEKLVEINDLQTLNGDKESIQSLVDYLTRRGK

LEEEWMEYLNSGIQRKLFV

A non-limiting example of a C-terminus variable domain or V domain may be isolated from the organism *Rhodopseudomonos* palustris tie-1, which may be provided as the following peptide sequence:

(SEQ ID NO: 51)
PSIEQVMPWLHLIFDAYEDYKAQRAREARELEERLAAEALEQAAREAA

EREVAAAIEAANAEAEIMLDDETHAEGGKKKKKRKHKD

The present invention, however, is not limited to these embodiments and may also include similar or otherwise homologous globular proteins, coiled-coil forming sequences, or foldons found in the microorganisms discussed herein or otherwise known in the art to assist with helical folding. As used herein, a "coiled-coil forming sequence" is a peptide domain having a gently twisted, rope-like bundles, such as that disclosed by K. Reid et al. (1994) FEBS Lett. May 16; 344(2-3):191-5 and as reviewed in Muller et al., (2000) Meth. Enzymol. 328: 261-283, the contents of which are each incorporated herein by reference. Coiled-coil sequences are comprised of a seven-residue repeat with positions 1-4 commonly being occupied by one or more hydrophobic amino acids and the remaining three amino acids being comprised of, generally, polar amino acids. While not limited thereto, the coiled-coil structures of the present invention may be trimeric structures. Examples of such coiled-coil domains include, but are not limited to, coiled-coil neck domains of collectin family proteins, a triple alpha-helical coiled-coil domain from human mannose-binding lectin, or coiled coil domains from other collagens types, including bacterial collagens. The following are two examples of the coiled coil containing domains from bacterial collagens:

Bacillus cereus ATCC 10987:
(SEQ ID NO: 48)
MNNKNKGKVFYGNDCCEVRACSHINISKSELTEFVRLLQALGQAIQAV

FQNPSQNNIDNLIAALNNLQKFLNCLDLSPAQRQIGNSIIANLLTILR

TTPFSCGALYVELQSLLNYLLYIAKLFKVDCCTTDKLVKLITEIQAIL

VQY

Rhodopseudomonas palustris:
(SEQ ID NO: 49)
PSIEQVMPWLHLIFDAYEDYKAQRAREARELEERLAAEALEQAAREAA

EREVAAAIEAANAEAEIMLDDETHAEGGKKKKKRKHKD

As also used herein, the term "foldon" refers to an amino acid sequence that is also sufficient to drive the multimerization and/or the correct folding of a collagen domain, see S. Frank et al., 2001, J. Mol. Biol., 308: 1081-1089; S. Boudko et al., 2002, J. Mol. Biol., 317: 459-470; J. Stetefeld et al., 2003, Structure, 11: 339-346, the contents of which are incorporated by reference herein. Examples of such foldon domains include, but are not limited to, a bacteriophage T4 fibritin foldon domain.

While it desirable that the variable or globular domain be provided in the final product to assist with refolding should the triple helical structure be denatured, it is not required. Rather, these domains may be provided during expression and enzymatically cleaved after formation of the triple helical structure. Enzymatic cleavage sequences may, thereby, be provided between the globular domain and the triple helical sequences and may include any sequence that is capable of being digested with an enzyme (e.g. protease). Such sequences include, but are not limited to, lysine or arginine residues suitable for tryptic digestion. Alternatively, enzymatic cleavage sequences may include phenylalanine, tyrosine, or tryptophan residues for chymotrypsin digestion. In even further embodiments, the enzymatic cleavage sequence may contain greater specificity for digestion and include a processing site that can be cleaved by a specific protease, e.g. factor Xa protease, thrombin, or enterokinase, Tomato Etch Virus (TEV) protease, or the like. While not limited thereto, such specific processing sites include but are not limited to the following:

Thrombin/Trypsin:
Leu-Val-Pro-Arg-Gly-Ser-Pro           (SEQ ID NO: 1)

Enterokinase:
Asp-Asp-Asp-Asp-Lys                   (SEQ ID NO: 2)

Factor Xa protease:
Ile-Glu-Gly-Arg                       (SEQ ID NO: 3)
or

Ile-Asp-Gly-Arg                       (SEQ ID NO: 4)

TEV protease:
Glu-Asn-Leu-Phe-Gln-Gly               (SEQ ID NO: 5)

PreScission™ protease:
Leu-Glu-Val-Leu-Phe-Gln-Gly-Pro.      (SEQ ID NO: 6)

The present invention, however, is not limited to the foregoing and may include similar enzymatic cleavage site or combination of cleavage sites that are known in the art.

Chimeric proteins including a globular domain, triple helical domain(s), and insert region(s) may be provided in any combination to optimize biomaterial and achieve the effects provided herein. Non-limiting examples of such proteins include the following sequences, repeats, fragments, homologues and combinations thereof:

| Chimeric Structure | Sequence |
|---|---|
| $V_{Sp}$-$CL_{Sp}$—with Thrombin/ Trypsin cleavage site | MNHKVHM<u>HHHHHH</u>DEQEEKAKVRTELIQELAQGLGGFEKKNFPTLGDE<br>DLDHTYMTKLLTYLQEREQAENSWRKRLLKGIQDHALD<u>LVPR↓GSPGPR</u><br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGL<br>PGKDGKDGQDGKDGLPGKDGKDGLPGKDGKDGQPGKPGKY<br>(SEQ ID NO: 29) |
| $V_{Sp}$-$CL_{Sp}$-$CL_{Sp}$—with Thombin/ Trypsin cleavage site | MNHKVHM<u>HHHHHH</u>DEQEEKAKVRTELIQELAQGLGGFEKKNFPTLGDE<br>DLDHTYMTKLLTYLQEREQAENSWRKRLLKGIQDHALD<u>LVPR↓GSPGPR</u><br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKP<u>GAAGVMGPRG</u><br>EQGPTGPTGPAGPRGLQGLQGLQGERGEQGPTGPAGPRGLQGERGEQGP<br>TGLAGKAGEAGAKGETGPAGPQGPRGEQGPQGLPGKDGEAGAQGPAGP<br>MGPAGERGEKGEPGTQGAKGDRGETGPVGPRGERGEAGPAGKDGERGP<br>VGPAGKDGQNGQDGLPGKDGKDGQNGKDGLPGKDGKDGQNGKDGLP<br>GKDGKDGQDGKDGLPGKDGKDGLPGKDGKDGQPGKPGKY<br>(SEQ ID NO: 30) |
| $V_{Sp}$-$CL_{Sp}$-(GFPGER)-$CL_{Sp}$—with Thrombin/Trypsin cleavage site and integrin binding site | MNHKVHM<u>HHHHHH</u>DEQEEKAKVRTELIQELAQGLGGFEKKNFPTLGDE<br>DLDHTYMTKLLTYLQEREQAENSWRKRLLKGIQDHALD<u>LVPR↓GSPGPR</u><br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKP<u>GFPGERGPRGE</u><br>QGPTGPTGPAGPRGLQGLQGLQGERGEQGPTGPAGPRGLQGERGEQGPT<br>GLAGKAGEAGAKGETGPAGPQGPRGEQGPQGLPGKDGEAGAQGPAGP<br>MGPAGERGEKGEPGTQGAKGDRGETGPVGPRGERGEAGPAGKDGERGP<br>VGPAGKDGQNGQDGLPGKDGKDGQNGKDGLPGKDGKDGQNGKDGLP<br>GKDGKDGQDGKDGLPGKDGKDGLPGKDGKDGQPGKPGKY<br>(SEQ ID NO: 31) |

| Chimeric Structure | Sequence |
|---|---|
| $V_{Sp}$-$CL_{Sp}$-$CL_{Sp}$—with Thrombin/Trypsin cleavage site and 4-aa short MMP cleavage site from human type III collagen | MNHKVHMHHHHHHDEQEEKAKVRTELIQELAQGLGGFEKKNFPTLGDE<br>DLDHTYMTKLLTYLQEREQAENSWRKRLLKGIQDHALDLVPR↓GSPGPR<br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKPGPLGIAGITGAR<br>GPRGEQGPTGPTGPAGPRGLQGLQGLQGERGEQGPTGPAGPRGLQGERG<br>EQGPTGLAGKAGEAGAKGETGPAGPQGPRGEQGPQGLPGKDGEAGAQG<br>PAGPMGPAGERGEKGEPGTQGAKGDRGETGPVGPRGERGEAGPAGKDG<br>ERGPVGPAGKDGQNGQDGLPGKDGKDGQNGKDGLPGKDGKDGQNGK<br>DGLPGKDGKDGQDGKDGLPGKDGKDGLPGKDGKDGQPGKPGKY<br>(SEQ ID NO: 32) |
| $V_{Sp}$$CL_{Sp}$-$CL_{Sp}$—with Thrombin/Trypsin cleavage site and 8-aa long MMP cleavage site from human type III collagen | MNHKVHMHHHHHHDEQEEKAKVRTELIQELAQGLGGFEKKNFPTLGDE<br>DLDHTYMTKLLTYLQEREQAENSWRKRLLKGIQDHALDLVPR↓GSPGPR<br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKPGAQGPPGAPGP<br>LGIAGITGARGLAGPRGEQGPTGPTGPAGPRGLQGLQGLQGERGEQGPTG<br>PAGPRGLQGERGEQGPTGLAGKAGEAGAKGETGPAGPQGPRGEQGPQG<br>LPGKDGEAGAQGPAGPMGPAGERGEKGEPGTQGAKGDRGETGPVGPRG<br>ERGEAGPAGKDGERGPVGPAGKDGQNGQDGLPGKDGKDGQNGKDGLP<br>GKDGKDGQNGKDGLPGKDGKDGQDGKDGLPGKDGKDGLPGKDGKDG<br>QPGKPGKY<br>(SEQ ID NO: 33) |
| $V_{Sp}$-$CL_{Sp}$-$CL_{Sp}$—with Thrombin/Trypsin cleavage site and 4-aa short MMP cleavage site from human type II collagen | MNHKVHMHHHHHHDEQEEKAKVRTELIQELAQGLGGFEKKNFPTLGDE<br>DLDHTYMTKLLTYLQEREQAENSWRKRLLKGIQDHALDLVPR↓GSPGPR<br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKPGPQGLAGQRGI<br>VGPRGEQGPTGPTGPAGPRGLQGLQGLQGERGEQGPTGPAGPRGLQGER<br>GEQGPTGLAGKAGEAGAKGETGPAGPQGPRGEQGPQGLPGKDGEAGAQ<br>GPAGPMGPAGERGEKGEPGTQGAKGDRGETGPVGPRGERGEAGPAGKD<br>GERGPVGPAGKDGQNGQDGLPGKDGKDGQNGKDGLPGKDGKDGQNG<br>KDGLPGKDGKDGQDGKDGLPGKDGKDGLPGKDGKDGQPGKPGKY<br>(SEQ ID NO: 34) |
| $V_{Sp}$-$CL_{Sp}$-$CL_{Sp}$—with Thrombin/Trypsin cleavage site and 8-aa long MMP cleavage site from human type II collagen | MNHKVHMHHHHHHDEQEEKAKVRTELIQELAQGLGGFEKKNFPTLGDE<br>DLDHTYMTKLLTYLQEREQAENSWRKRLLKGIQDHALDLVPR↓GSPGPR<br>GEQGPTGPTGPAGPRGLQGLQGLQGERGEQGPTGPAGPRGLQGERGEQG<br>PTGLAGKAGEAGAKGETGPAGPQGPRGEQGPQGLPGKDGEAGAQGPAG<br>PMGPAGERGEKGEPGTQGAKGDRGETGPVGPRGERGEAGPAGKDGERG<br>PVGPAGKDGQNGQDGLPGKDGKDGQNGKDGLPGKDGKDGQNGKDGLP<br>GKDGKDGQDGKDGLPGKDGKDGLPGKDGKDGQPGKPGPSGAEGPPGP<br>QGLAGQRGIVGLPGPRGEQGPTGPTGPAGPRGLQGLQGLQGERGEQGPT<br>GPAGPRGLQGERGEQGPTGLAGKAGEAGAKGETGPAGPQGPRGEQGPQ<br>GLPGKDGEAGAQGPAGPMGPAGERGEKGEPGTQGAKGDRGETGPVGPR<br>GERGEQGPAGKDGERGPVGPAGKDGQNGQDGLPGKDGKDGQNGKDGL<br>PGKDGKDGQNGKDGLPGKDGKDGQDGKDGLPGKDGKDGLPGKDGKD<br>GQPGKPGKY<br>(SEQ ID NO: 35) |
| $V_{Sp}$-$CL_{Sp}$—with Thrombin/Trypsin cleavage site | MNHKVHMHHHHHHDEQEEKAKVRTELIQELAQGLGGFEKKNFPTLGDE<br>DLDHTYMTKLLTYLQEREQAENSWRKRLLKGIQDHALDLVPR↓GSPGPR<br>GPRGPQGEQGPQGERGFTGPQGPVGPQGEQGPQGERGFTGPQGPIGLQG<br>EQGPQGERGFTGPQGPVGPQGEQGPQGERGFTGPQGPVGPQGEQGPQGE<br>RGFTGPQGPIGPQGEQGPQGERGFTGPQGPIGPQGNQGPIGPQGEQGPQG<br>ATFPQFPQGPVGPQNQGPIGPQGPVGPQGPQGQPGVN<br>(SEQ ID NO: 36) |
| $CL_{Cp}$-$V_{Rp}$ | MHHHHHHGPRGPRGPQGEQGPQGERGFTGPQGPVGPQGEQGPQGERGF<br>TGPQGPIGLQGEQGPQGERGFTGPQGPVGPQGEQGPQGERGFTGPQGPV<br>GPQGEQGPQGERGFTGPQGPIGPQGEQGPQGERGFTGPQGPIGPQGNQGP<br>IGPQGEQGPQGATGPQGPQGPVGPQGNQGPIGPQGPVGPQGPQGQPGVN<br>GPRPSIEQVMPWLHLIFDAYEDYKAQRAREARELEERLAAEALEQAARE<br>AAEREVAAAIEAANAEAEIMLDDETHAEGKKKKKRKHKD<br>(SEQ ID NO: 37) |

| Chimeric Structure | Sequence |
|---|---|
| V$_{Sp}$-CL$_{Cp}$-CL$_{Cp}$—with Thrombin/Trypsin cleavage site and natural break | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPQGPVN<u>GAAGVM</u>GPRG PRGPQGEQGPQGERGFTGPQGPVGPQGEQGPQGERGFTGPQGPIGLQGE QGPQGERGFTGPQGPVGPQGEQGPQGERGFTGPQGPVGPQGEQGPQGER GFTGPQGPIGPQGEQGPQGERGFTGPQGPIGPQGNQGPIGPQGEQGPQGA TGPQGPQGPVGPQGNQGPIGPQGPVGPQGPQGPGVN (SEQ ID NO: 38) |
| V$_{Sp}$-CL$_{Cp}$-CL$_{Cp}$—with Thrombin/Trypsin cleavage site and integrin site | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPGVN<u>GFPGERGPRGP</u> RGPQGEQGPQGERGFTGPQGPVGPQGEQGPQGERGFTGPQGPIGLQGEQ GPQGERGFTGPQGPVGPQGEQGPQGERGFTGPQGPVGPQGEQGPQGERG FTGPQGPIGPQGEQGPQGERGFTGPQGPIGPQGNQGPIGPQGEQGPQGAT GPQGPQGPVGPQGNQGPIGPQGPVGPQGPQGPGVN (SEQ ID NO: 39) |
| V$_{Sp}$-CL$_{Cp}$-CL$_{Cp}$—with Thrombin/Trypsin cleavage site and 4-aa short MMP cleavage site from human type III collagen | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPGVN<u>GPLGIAGITGAR</u> GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPGVN (SEQ ID NO: 40) |
| V$_{Sp}$-CL$_{Cp}$-CL$_{Cp}$—with Thrombin/Trypsin cleavage site and 8-aa long MMP cleavage site from human type III collagen | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPQGPVN<u>GAQGPPGAPGP LGIAGITGARGLA</u>GPRGPQGEQGPQGERGFTGPQGPVGPQGEQGPQGER GFTGPQGPIGLQGEQGPQGERGFTGPQGPVGPQGEQGPQGERGFTGPQGP VGPQGEQGPQGERGFTGPQGPIGPQGEQGPQGERGFTGPQGPIGPQGNQG PIGPQGEQGPGFATGPQGPQGPVGPQGNQGPIGPQGPVGPQGPQGPGVN (SEQ ID NO: 41) |
| V$_{Sp}$-CL$_{Cp}$-CL$_{Cp}$—with Thrombin/Trypsin cleavage site and 4-aa short MMP cleavage site from human type II collagen | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPVGPQGPQGPGVN<u>GPQGLAGQRGI V</u>GPRGPQGEQGPQGERGFTGPQGPVGPQGEQGPQGERGFTGPQGPIGLQ GEQGPQGERGFTGPQGPVGPQGEQGPQGERGFTGPQGPVGPQGEQGPQG ERGFTGPTGPIGPQGEQGPQGERGFTGPQGPIGPQGNQGPIGPQGEQGPQ GATGPQGPQGPVGPQGNQGPIGPQGPVGPQGPQGPGVN (SEQ ID NO: 42) |
| V$_{Sp}$-CL$_{Cp}$-CL$_{Cp}$—with Thrombin/Trypsin cleavage site and 8-aa long MMP cleavage site from human type II collagen | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPR GPRGPQGEQGPQGERGFTGPQGPVGPQGEQGPQGERGFTGPQGPIGLQG EQGPQGERGFTGPQGPVGPQGEQGPQGERGFTGPQGPVGPQGEQGPQGE RGFTGPQGPIGPQGEQGPQGERGFTGPQGPIGPQGNQGPIGPQGEQGPQG ATGPQGPQGPVGPQGNQGPIGPQGPPVGPQGPQGPQGPVN<u>GPSGAEGPPGP QGLAGQRGIVGLP</u>GPRGPQGEQGPQGERGFTGPQGPVGPQGEQGPQGER GFTGPQGPIGLQGEQGPQGERGFTGPQGPVGPQGEQGPQGERGFTGPQGP VGPQGEQGPQGERGFTGPQGPIGFPGEQGPQGERGFTGPQGPIGPQGNQG PIGPQGEQGPQGATGPQGPQGPVGPQGNQGPIGPQGPVGPQGPQGPGVN (SEQ ID NO: 43) |
| V$_{Sp}$-CL$_{SE}$ | MNHKVHMHHHHHHDEQEEKAKVRTELIQELAQGLGGFEKKNFPTLGDE DLDHTYMTKLLTYLQEREQAENSWRKRLLKGIQDHALDLVPR↓GSPGPA GPAGPQGPAGPAGAQGPAGPAGPQGPAGPQGSAGAPGPKGDTGAAGPA GEAGPKGETGAAGPKGDTGAAGPAGPKGDTGAAGPAGPKGDTGAAGA |

| Chimeric Structure | Sequence |
|---|---|
| | TGPKGEKGETGAAGPKGDKGETGAAGPKGDKGETGAAGPKGEKGETGA<br>VGPKGDKGETGAAGPKGDRGETGAVGPKGDKGETGAVGPKGDKGETG<br>AIGPKGDKGDKGDKGDAGVAGPQGIQGVKGDTGLQGPKGDAGPQGAP<br>GTPGGG<br>(SEQ ID NO: 44) |
| CL$_{Rp}$-V$_{Rp}$ | MHHHHHHGRPGPQGPRGRPGEPGRPGPQGHPGRPGPEGPRGKQGPVGK<br>PGPQGKAGPQGKPGIAGKPGPDGKPGPIGPQGKAGPQGPRGEQGLRGEQ<br>GPRGEQGPQGPRGEQGPRGEPGPAGALPSIEQVMPWLHLIFDAYEDYKA<br>QRAREARELEERLAAEALEQAAREAAEREVAAAIEAANAEAEIMLDDET<br>HAEGGKKKKKRKHKD<br>(SEQ ID NO: 45) |
| CL$_{Mb}$ | MHHHHHHGLPGPKGDPGPQGPAGPKGEPGPKGEPGPKGEPGPKGEPGPK<br>GEPGPKGEPGPKGEPGPKGEPGPKGEPGPRGEAGPQGALGPKGEAGSRGEPGPRGE<br>PGPKGEAGLAGAPGPKGEAGPRGPQGERGPPGAPGAA<br>(SEQ ID NO: 46) |

V$_{Sp}$—Refers to the variable or globular domain isolated from the organism Streptococcus pyogenes.
CL$_{Sp}$—Refers to the triple helical region isolated from the organism Streptococcus pyogenes.
CL$_{Cp}$—Refers to the triple helical region isolated from the organism Clostridium perfringens.
V$_{Rp}$—Refers to the variable or globular domain isolated from the organism Rhodopseudomonos palustris tie-1.
CL$_{SE}$—Refers to the triple helical region isolated from the organism Solibacter usitatus Ellin6076.
CL$_{Mb}$—Refers to the triple helical region isolated from the organism Methylobacterium sp. 4-46.

Methods of expressing the recombinant collagen-like proteins of the instant invention include standard expression methods that are generally known in the art, such as those discussed in Molecular Cloning (Sambrook and Russell, (2001)), the contents of which are incorporated herein by reference. In one non-limiting example, the recombinant collagen-like structures of the present invention may be expressed by cloning into cold-shock vectors. As used herein, a "cold-shock vector" relates to a expression cassette providing specific induction of the expression of a target gene at or about 15° C. or room temperature, resulting in a high yield of protein. One such vector system was developed by taking advantage of the E. coli cspA cold-shock adaptation mechanism. When an E. coli culture is shifted from 37° C. to 15° C. (i.e. cold shock), cell growth is significantly reduced while CspA, the major cold-shock protein, is dramatically induced. Utilizing this, key expression elements from the cspA gene may be incorporated into an expression cassette to facilitate expression of a target protein upon incubation at 15° C. or 25° C. Such key elements include a promoter region (e.g. cspA promotor) with, optionally, a downstream regulator region (e.g. a lac operator) to strictly control expression. A series of expression vectors, termed pCold vectors (commercially produced by TaKaRa Bio) are available, which utilize such key elements to drive the high expression of a target gene upon induction by shifting a culture temperature from 37° C. to 15° C.

In accordance with the foregoing, a nucleic acid sequence encoding the recombinant collagen-like structure of the present invention may be isolated and inserted into a cold-shock expression cassette and transfected into a bacterial organism. As used herein, a nucleic acid sequence is a DNA sequence but may also include any other type of sequence known in the art for use in expression cassettes and bacterial cloning. The introduction of the nucleic acid into the cold-shock expression vector follows well-established techniques of molecular biology, as provided below or otherwise described in manuals such as Molecular Cloning (Sambrook and Russell, (2001)), the contents of which are incorporated herein by reference. In one embodiment a nucleic acid sequence encoding the entire sequence of the recombinant bacterial collagen-like structure of the present invention may be isolated, using standard molecular techniques, and inserted into a pCold, or other similar, expression cassette.

The expression constructs of the present invention may be cloned into a bacterial host using methods known in the art and as described in manuals such as Molecular Cloning (Sambrook and Russel, (2001)). More specifically, the high yield expression system of the present invention may be comprised of cloning the expression construct of the present invention into a cold-shock protein competent E. coli. These cells may be transformed using any transfection, transformation, or other similar technique known in the art for inserting an expression cassette into a micro-organism. Post-transformation, cells may be initially grown on suitable culture media (e.g. M9-casamino acid) at 37° C. until they reached A600 of about 0.8-1.2. Cultures may then be shifted to 15° C. to induce protein expression of the targeted protein, and incubated overnight, to produce the targeted protein. One of ordinary skill in the art will appreciate that the incubation times and temperatures may be varied and still achieve similar results. Accordingly, the foregoing method of culturing cells expressing the proteins of the present invention are not necessarily limiting to the present invention. While the recombinant proteins of the present invention could be produced using conventional cloning/expression methods, as provided below, the use of cold-shock vectors is particularly advantageous to the present invention because of high yield production of the desired protein.

Post-incubation, cells may be harvested, disrupted and the targeted protein isolated. Purification of the polypeptide may be conducted using a combination of known protein purification techniques such as ammonium sulfate fractionation, PEG precipitation, ultrafiltration and various chromatographies. For example, the purification techniques can be facilitated by binding of a ligand (i.e. a tag sequence, biological active sequence, etc.) to a carrier through one of the binding mechanisms discussed herein. The triple-helix domain may then be enzymatically cleaved from the expressed bacterial collagen product by treating with the enzyme corresponding with the enzymatic digestion domain discussed herein. The resulting proteins may be purified and characterized using standard methods known in the art. As used herein, ligand or "tag" sequences include polypeptide sequences that are used to localize the target protein (e.g. the collagen polymer), to purify it from a cell extract, to immobilize it for use in binding assays, or to otherwise study its biological properties and/or function. Examples include, but are not limited to, polyhistidine tracts (e.g. His$_6$), histidine-tryptophan sequences FLAG peptide fragment, hemagglutinin (HA) tag sequence, a myc tag sequence, a glutathione-S-transferase tag sequence, a maltose binding protein (MBP) tag sequence, a green fluorescent protein tag sequence, an myc-pyruvate kinase tag sequence, an influenza virus hemagglutinin tag sequence, and various Ig tag sequences, or other similar tag sequences otherwise known in the art. Again, while the present invention exemplifies cold-expression vector expressed in E. coli., the present invention is not limited thereto. Rather the expression vector may be any other similar type of expression vector or other standard expression vector that is generally known in the art to express a targeted protein. To this end, the microorganism is not limited to an E. coli and may be comprised of any bacterial host or yeast (e.g. Pichia) expression system known in the art. The instant invention may, thereby, be adapted for expression in such organisms using standard protocols known in the art.

The recombinant bacterial collagen-like structure of the invention is particularly advantageous because it provides an easily producable triple-helical constructs that is stable at temperatures close to human body temperature, either in its native state or after stabilization by chemical cross-linking. This design will lead to the production of collagen-based products of varying lengths. Variation in length should lead to the properties suitable for a wide range of biomaterials, biomedical applications, and cosmetic applications.

Comparison of the properties of the collagenous CL domain with the CL-CL domain which is twice as long indicated that the length of the bacterial triple-helix domain did not affect the molecular thermal stability but did affect the morphology of the fibrils formed at neutral pH in the cold, producing larger diameters and longer fibrils. Increasing the length of the construct to CL-CL-CL and CL-CL-CL-CL further increase the propensity for fibril or aggregate formation and improve the fibril morphology.

Bacterial collagen-like proteins retain the versatility of the collagen triple-helix motif, while allowing high yield expression systems and easy manipulation with no requirement for post-translational modifications. The formation of fibrils by the bacterial collagen-like proteins, as reported here, indicates that these fibrils are useful for biomaterials and tissue engineering applications.

The larger diameters and longer fibrils formed by CL-CL domains compared with CL suggests that increasing the length of the triple-helix further, e.g. CL-CL-CL, should lead to fibrils more closely resembling those found in animal tissues. The importance of collagen length in fibril formation is supported by studies on collagen model peptides. The properties of fibrils formed by bacterial collagen may also be modulated by changes in amino acid sequence, the introduction of cross-linking, and the presence of other matrix molecules, e.g. proteoglycans.

Thus the recombinant collagen of the present invention may be used, for example, as a biomaterial for medical use replacing human collagen, as a cosmetic ingredient (e.g., as a moisturizer since it has a high calorimetric enthalpy suggesting an excellent water-holding capacity), and as new biodegradable biomaterials, which can be used in the food industry as well as pharmacological industry. The constructs of the present invention also have the potential for high-yield production of bacterial gelatin. The constructs of this invention are ideal for manipulations and applications as scaffolds or aggregates in tissue engineering.

In one embodiment, for example, such aggregates or scaffolds could be formed by chemical crosslinking in the presence of glutaraldehyde vapour. More specifically, purified CL protein is prepared in 20 mM acetic acid and freeze dried. Dry collagen is then held at 20° C. over vapour from 20% w/v glutaraldehyde (GA) for 18 h in a closed vessel. Samples are then held covered in air and stored at room temperature until analysis. Alternatively, high concentrations of the recombinant structures at low temperature naturally promotes formation of aggregate or fibrillar structures in S. pyogenes and several of the other bacterial collagens defined here, e.g. methylbacterium, have an even greater tendency towards aggregation.

Non-limiting examples of biomedical products that can be produced from aggregation of the instant recombinant proteins and their possible applications include, but are not limited to, the following: soluble recombinant collagens, such as for use in dermal implants, drug carriers, plastic coatings for medical devices, implant coatings (orthopedic and vascular), shape-formation materials, viscosurgery, vascular sealants, cosmetics, and regulators of enzymes activity (e.g., metalloproteinases); sponge-like materials, such as for use in three-dimensional cell cultures, tissue and organ engineering, hemostatic agents, and wound therapy (artificial skin and wound dressings); fibers, such as for use in surgical sutures and hemostatic agents; gel-like materials, such as for use in tissue implants, corneal shields, contact lens, and matrices for cell culture; and membrane-like materials, such as for use in anti-adhesion membranes, drug delivery systems, artificial skin, and the like.

Additionally, the recombinant collagen of the present invention may be used outside of the biomedical arena with industrial applications including, but not limited to, the following: leather industry applications, stabilizers, thickeners in glue manufacture, emulsifiers, foaming agents suitable for paper or textile manufacture, photographic films, manufacture of rubber substitutes, food industry applications, and the like.

The triple-helix protein motif confers the structural advantages found in collagen and allows incorporation of conformation-dependent interaction sites. The bacterial origin of the collagen-like sequence ensures compatibility in a bacterial expression system in terms of codon usage and other factors. This allows use of a highly efficient bacterial expression system, and flexible modifications of sequence. Important interaction sites, cleavage sites, and self-association can be successfully incorporated in this bacterial triple-helix protein in the absence of hydroxyproline. The development of a bacterial, hydroxyproline-free, triple-helix protein system provides great benefits for the development of collagen-based biomaterials and tissue engineering and offers a new system for studying basic principles of collagen function.

Although this invention exemplifies triple helical constructs that are stable near human body temperature, constructs that form stable triple-helical entities at lower temperatures are not excluded from the present invention, particularly constructs that may be cross-linked for further stabilization or suitable for production of gelatin-like systems or other applications.

EXAMPLES

Materials and Methods

Analysis of bacterial genomes The NCBI microbial genome database was searched for annotated known and predicted collagen-like proteins with a relatively long (Gly-Xaa-Yaa)$_n$ domain containing at least 35 repeats and lacking repetitive stretches of a single amino acid motif. For further selection, thermal stability of the collagen-like domains of selected proteins were predicted using the collagen stability calculator (jupiter.umdnj.edu/collagen_calculator/) and sequences showing regions of very low stability were excluded. ProtParam tool was used for evaluation of the AA content and physicochemical parameters.

DNA Amplification and Cloning. Full length genes for the collagen-like proteins were amplified using genomic DNA and corresponding primers (Table 1). Genomic DNA of *Clostridium perfringens* (*C. perfringens*), SM101 was provided by Hirofumi Nariya (Kagawa University, Japan), DNA of *Solibacter usitatus* (*S. usitatus*) was a gift from Cheryl R. Kuske (Los Alamos National Laboratory, N. Mex.), DNA of *Methylobacteria* sp 4-46 (*M. sp* 4-46) was a gift from Christopher Marx (Harvard University, Mass.), DNA of *Rhodosudomonas palustris* (*R. palustris*) and *Corynebacterium diphtheria* (*C. diphtheria*) were purchased from ATCC. Amplification conditions were optimized for each pair of primers. Genes were cloned in pCR 2.1-TOPO vector and verified by DNA sequencing.

Each collagen domain CL, is denoted by the bacterial source, e.g. $CL_{Rp}$ is the (Gly-Xaa-Yaa)$_n$ region from *R. palustris*. The non-collagenous domains are denoted as (N)V for the N-terminal non-collagenous domain. For example, (N)$V_{Sp}$ is N-terminal non-collagenous V domain from *S. pyogenes*. For obtaining of the full length *C. perfringens* construct (N)$V_{Cp}$-$CL_{Cp}$-(C)$V_{Cp}$, and partial *C. perfringens* constructs (N)$V_{Cp}$-$CL_{Cp}$($AA_{1-242}$), $CL_{Cp}$($AA_{54-242}$) protein and $CL_{Cp}$-(C)$V_{Cp}$ ($AA_{54-403}$), corresponding fragments were amplified by PCR and re-cloned into the *E. coli* expression pColdII vector via NdeI/BamHI sites (the numbers in parenthesis correspond to the amino acids of the full size protein and are presented for the fragments the first time they are used). To obtain (N)$V_{Sp}$($AA_{1-74}$)-$CL_{Cp}$ and $CL_{Cp}$-(C)$V_{Rp}$ ($AA_{127-212}$) recombinant proteins, fragments after amplification and assembly were cloned into the pColdIII via ApaI/BamHI and Nde/BamHI sites, correspondingly. To construct full length *S. usitatus* constructs (N)$V_{Su}$-$CL_{Su}$-(C)$V_{Su}$, and partial constructs (N)$V_{Su}$($AA_{1-74}$)-$CL_{Su}$($AA_{1-288}$), $CL_{Su}$ ($AA_{43-288}$), $CL_{Su}$-(C)$V_{Su}$($AA_{30-434}$), amplified fragments were cloned into the pColdII vector via NdeI/Hind III sites. pCold III vector already containing N-terminal domain of Scl2 *S. pyogenes* and SmaI/ApaI sites was used for obtaining (N)$V_{Sp}$($AA_{1-74}$)-$CL_{Su}$($AA_{43-288}$) protein. Full length (N)$V_{Ms}$-$CL_{Ms}$-(C)$V_{Ms}$, (N)$V_{Ms}$-$CL_{Ms}$($AA_{23-271}$), $CL_{Ms}$ ($AA_{23-271}$) *M. sp* 4-46 recombinant proteins were constructed by amplification of the fragments and inserting them into pCold II vector using NdeI/BamHI sites. Full length and $CL_{Rp}$($AA_{10-126}$)-(C)$V_{Rp}$($AA_{127-212}$) *R. palustris* recombinant proteins were constructed by assembly of the corresponding fragments in pCold II vector using NdeI/BamHI sites. Fragments for the full length and N-terminal domain of Scl2 (N)$V_{Sp}$($AA_{1-74}$)-$CL_{Cd}$($AA_{1-222}$) fusion protein from *C. diphtheria* were cloned into pCold II and pCold III vectors already containing N-terminal domain via NdeI/BamHI and ApaI/BamHI sites, correspondingly. All recombinant proteins contained N-terminal His-Tag sequence for purification by affinity chromatography and thrombin cleavage site sequences were inserted between the N-terminal globular domain and collagen-like domain sequences by PCR.

For expression of the collagen-like domain from several bacterial species using heterologous registration domain from another bacterial species, we inserted collagen-like domains from *Clostridium perfringens* (ABG86771.1) and *Corynebacterium diphtheria* (CAE50366) into the pColdIII-VCL vector for the expression of the Scl 2.28 of *Streptococus pyogenes* by replacing collagen-like sequence of the Scl 2.28.

Protein expression and purification. Recombinant proteins were expressed in *E. coli* BL21 strain. For small scale purification and fractionation studies, bacterial cultures were grown in 10 ml of M9-casamino acid medium at 37° C. until A600 reached 0.9-1.0, then expression of the proteins was induced by 1 mM isopropyl-D-thiogalactopyranoside and cultures were incubated on a shaker overnight at 20° C. To test protein solubility, cultures were centrifuged and pellets dissolved in 20 mM Na-phosphate, pH 7.4, 500 mM NaCl, sonicated and centrifuged.

Supernatant was considered as a soluble fraction, whereas pellet undergoes additional cycle of resuspension, sonication and centrifugation. The final pellet was called the insoluble fraction. Proteins were analyzed by 12% SDS-PAGE. Proteins were purified from one liter cultures, grown and induced as described for small scale production. Overnight cultures were centrifuged and resuspended in 20 mM Na-Phosphate, pH 7.4, 500 mM NaCl buffer with 10 mM β-mercaptoethanol, sonicated by 4-5xone minute bursts in Ultrasonic processor XL sonicator (Misonix). Extracts were centrifuged for 10 min at 12,000 g, and after additional extraction of the pellets, supernatants were combined and centrifuged one hour at 45,000 rpm (rotor 50Ti, Beckman L7-55). Twenty five mM of imidazole was added to the extracts and it was loaded on 12.5 ml Ni-NTA agarose (QIAGEN) column. Column was washed sequentially with 50 ml of the binding buffer (Na-phosphate saline with 25 mM imidazole and 10 mM β-mercaptoethanol), 120 ml of the buffer with 58 mM of the imidazole and 50 ml of the buffer with 96 mM imidazole. Proteins were eluted with 30 ml of buffer containing 400 mM of imidazole. Proteins were dialyzed against Na-phosphate buffer, pH 8.6 with 50 mM glycine. Protein purity was checked by SDS-PAGE and MALDI-TOF mass spectrometry. The following final yields from one liter of liquid culture were obtained for purified soluble proteins: (N)$V_{Sp}$-$CL_{Cp}$-22.5 mg/l; $CL_{Cp}$-(C)$V_{Rp}$-6.3 mg/l; $CL_{Cp}$-9.8 mg/l; (N)$V_{Ms}$-$CL_{Ms}$-22.3 mg/l; $CL_{Ms}$-4.3/mg/l; (N)$V_{Sp}$-$CL_{Su}$-15.3 mg/l; $CL_{Su}$-4.3 mg/l; $CL_{Rp}$-(C)$V_{Rp}$-4.3 mg/l; $CL_{Rp}$-1 mg/l. We optimized further the growth conditions for two proteins, (N)$V_{Sp}$-$CL_{Cp}$ and (N)$V_{Sp}$-$CL_{Su}$ and corresponding CL domains. The use of rich 2xLB medium and induction of protein expression at $A_{600}$ reaching 5-6 lead to increased yields for $CL_{Cp}$ and $CL_{Su}$ up to 30-40 mg/l.

Trypsin Digestion. To test the recombinant proteins for sensitivity to trypsin digestion and to isolate the collagenous fragments, proteins were digested at room temperature with trypsin at a ratio 1:1000 (protein:enzyme) for different periods of time, and efficiency of the digestion was checked by electrophoresis. The reaction was terminated by addition of PMSF, followed by centrifugation and the supernatants were loaded onto a Superdex™ 200 gel filtration column (GE Healthcare). The purity of the fractions was checked by mass spectrometry.

Circular Dichroism Spectroscopy. AVIV Model 62DS spectropolarimeter (Aviv Associates Inc., Lakewood, N.J.) was used for the recording of the CD spectra. Proteins were equilibrated in 1 mm cuvettes for at least 24 hrs at 4° C. Each scan was repeated three times and CD spectra were recorded from 195 to 260 nm with an average time of 5 s at 5 nm interval. Protein melting was monitored at 220 nm by increasing temperature in 0.33° C. increments from 0 to 70° C. Proteins were maintained for 2 min at each temperature point and the average rate of temperature increase was 0.1° C./min. $T_m$ is defined as the temperature at which the fraction folded is 50% in the curve fitted to the thermal transition. Proteins were refolded by decreasing the temperature from 70 to 0° C. and process was recorded at 220 nm. The percentage of the refolding was determined as the ratio of the CD signal regained at 0° C. after refolding to the initial signal before melting.

Example 1

Selection of Collagen-Like Protein Candidates

To choose candidate proteins with collagen-like domains, a search was initiated in bacterial genomic databases of pathogenic and non-pathogenic bacteria for relatively long (Gly-Xaa-Yaa)$_n$ domains (n>35), since the stability of the collagen triple helix is known to depend upon length of the protein up to a certain size after which $T_m$ is length independent. Candidates were further analyzed in terms of predicted thermal stability of their CL domains using the collagen stability calculator (jupiter.umdnj.edu/collagen_calculator/), eliminating proteins predicted to have regions of low relative stability. The final protein candidates were grouped according to amino acid composition, and representative candidates with high percentage of charged residues, prolines, or predominantly polar residues were chosen for experimental investigations. It was also desirable to include proteins from non-pathogenic bacteria since none had been studied previously. Using these criteria, a set of putative proteins with collagen domains were selected from five bacteria (Table 1): *C. perfringens*, a pathogenic gram-positive bacteria which is the causative agent of gas gangrene; *C. diphtheria*, a pathogenic rod-shaped grampositive actinobacteria responsible for diphtheria; non-pathogenic gram-negative *M. sp* 4-46 found mostly in soils or in plants which can utilize methanol emitted by the plants and stimulate plant development; non-pathogenic Gram-negative Acidobacteria (*S. usitatus*) which are abundant in soils; and non-pathogenic gram-negative *Rhodopseudomonas* (*R. palustris*), a phototrophic organism inhabiting marine environments and soil.

FIG. 1 provides an overview of the collagen domains in these 5 bacteria. Specifically, these bacteria contain distinctive amino acid compositions, with widely varying percentages of Proline, hydrophobic residues (Val, Ile, Leu, Met, Phe, Trp, Cys), charged residues (Asp, Glu, Lys, Arg, His), and polar residues (Ser, Thr, Cys, Asn, Gln). All of the proteins have a high proportion of Pro, varying from 19.5-40% of all residues in the Xaa and Yaa positions. It is interesting to note that the proteins with the lower Pro contents have very high contents of acidic residues. The CL domain from *C. perfringens* ($CL_{Cp}$) has the lowest charge content (17% of all residues in the Xaa and Yaa positions) and a high content of Gln residues (29%) exclusively in the Yaa position, with a total of 37% polar residues, and 31% Pro. This contrasts with 35% charged residues, 37% Pro and 15% polar residues in the CL domain of *R. palustris*. Two proteins selected for the expression have acidic pI values (4.7 for *C. perfringens* and 5.4 for *S. usitatus*) whereas the rest of them are highly basic (pI 8.6, 9.3 and 8.85 for *M. sp* 4-46, *R. palustris* and *C. diphtheria*, respectively).

Repeating sequence patterns are notable in most of these proteins. For example, $CL_{Cp}$ has 6 full and 3 partial repeats of the Gln rich sequence GP[RQ]GP[VIR]G[PL]QGEQG-PQGERGF (SEQ ID NOS.: 79-90) while eight full repeating charge sequences of the form GPKGEP (SEQ ID NO.: 63) are present in $CL_{Ms}$. Peptide models of these repeats suggest they promote self-association into fibrillar structures. The CL region from *S. usitatus* ($CL_{Su}$) has 2 large Ala-rich repeats at the N-terminus GPAGPAGPQGPAGP (SEQ ID NO.: 64) as well as numerous imperfect repeats. Other repeating sequences are seen in the CL domains of *C. diphtheria* ($CL_{Cd}$) and *R. palustris* ($CL_{Rp}$). This contrasts with the absence of repeating sequences in animal collagens, although there are periodicities of charged and hydrophobic residues. There are different numbers of these repeats in different strains, and it is not clear at this stage if any of the bacterial collagen repeats are important for the function and stability of the proteins or if they are related to the evolution of these collagen-like sequences.

TABLE 1

Predicted bacterial collagen-like proteins

| Bacteria | Protein | MW (Kd)/PI | Primers, forward/reverse |
|---|---|---|---|
| Closridium perfringens, SM 101 | ABG86771.1 | 42.1/4.7 | 5' AGAAGCTCCAATGGCAAAGGAAGATGA 3' (SEQ ID NO: 52)<br>5' ACTCATTCAACTGGAGGCGTATGCATTTC 3' (SEQ ID NO: 53) |
| Solibacter usitatus | YP_822627.1 | 40.8/5.4 | 5' TCCCGATTGAGGCGAAGCAAA CTT 3' (SEQ ID NO: 54)<br>5' TACGCGATGACGCATTGAGGGAAA 3' (SEQ ID NO: 55) |
| Methylobacterium sp 4-46 | ACA18713.1 | 33.5/8.6 | 5' AATCTCGACCGCAAGGACCTCTAC 3' (SEQ ID NO: 56)<br>5' ACATCCGCAAGGCGAAGCAAT 3' (SEQ ID NO: 57) |
| Rhodopseudomonas palustris | YP_0019930 | 22.1/9.3 | 5' AATTGAAGCCGTCACGCAAGCTCT 3' (SEQ ID NO: 58)<br>5' TGACGGAACATCAAGACGCTGTTCAA 3' (SEQ ID NO: 59) |
| Corynebacterium diphtheriae | CAE50366.1 | 25.8/8.85 | 5' AACTTTCCCGCCGTGTTGTCCAAT 3' (SEQ ID NO: 60)<br>5' TGCAAGAATTGTTGGGCCATGCGA 3' (SEQ ID NO: 61) |

These proteins from 5 different bacteria were selected on the basis of the characteristics of their (Gly-Xaa-Yaa)$_n$ domains. But all animal collagens and the few bacterial collagen-like proteins characterized so far have non-triple-helix regions surrounding the triple-helix domain which are necessary for trimerization, nucleation and registration of the triple-helix. The full length protein in the open reading frame containing the (Gly-Xaa-Yaa)$_n$ sequence was included for expression in all cases (Table 1).

Example 2

Expression of Bacterial Collagen-Like Proteins in *E. coli*

Genes for these candidate proteins (Table 1) were cloned from genomic DNA and expressed in *E. coli* BL21 strain using cold-shock expression vectors, as provided above. Initial expression plasmids were constructed using full length proteins including N or C-terminal non-collagenous domains. Such sequences are identified in FIG. 2 where the numbers indicate the length of each domain in AA; black filled boxes indicate the CL domains of corresponding proteins; the empty boxes indicate N- and C-terminal domains; vertical empty boxes indicate collagen-like sequence interruptions; and boxes with line dashed patterns indicate V domain from Scl2 of *S. pyogenesis* ($V_{Sp}$) and C-terminal V domain from *R. palustris* ($V_{Rp}$). Predicted signal peptide coding regions were not included in the constructs when they could be identified.

Figure 2:
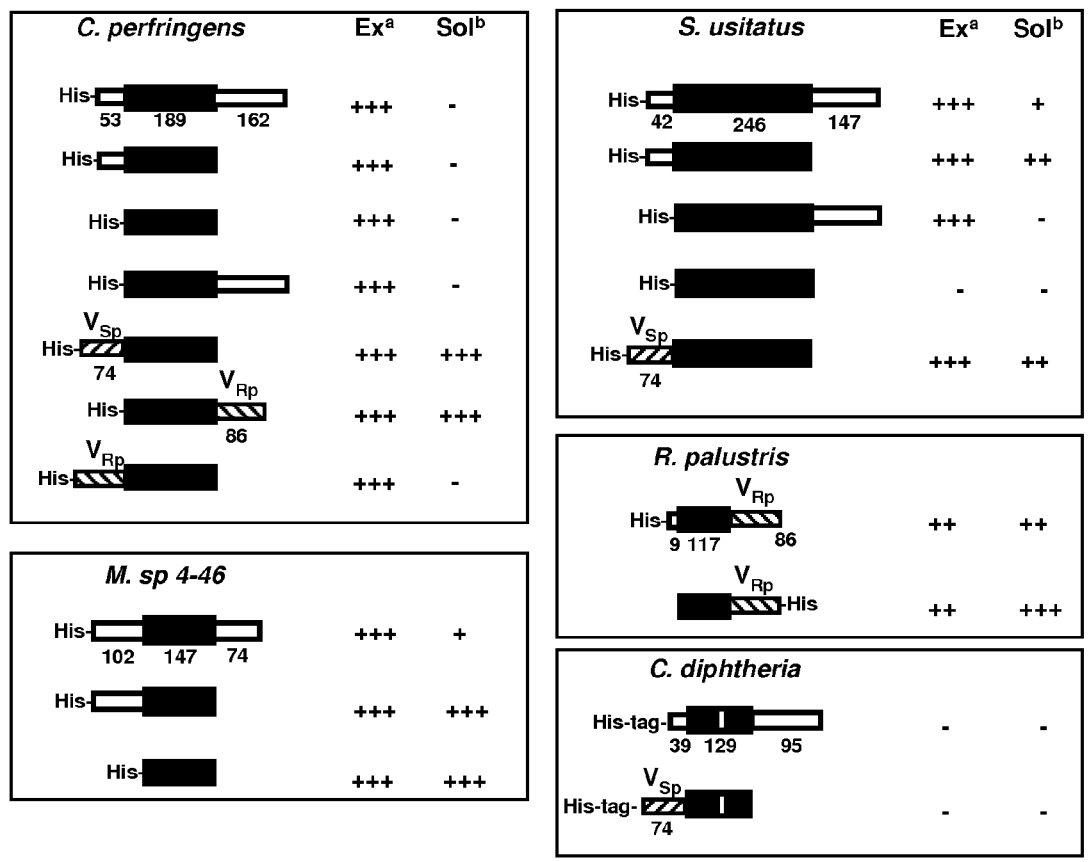
FIG. 2 illustrates a schematic diagram of recombinant proteins with bacterial collagen-like domains, constructed for expression in E. coli.

No inducible expression was observed for the *C. diphtheria* recombinants and this bacterial protein was not further characterized (FIG. 2). The problematic expression could be due to a 9 residue interruption in the (Gly-Xaa-Yaa)$_n$ sequence of the CL$_{Cd}$ region, since such breaks in the repeating triplet pattern have been shown to lead to the disturbance and destabilization of the triple helix and possibly to the protein instability. Good expression was observed for the recombinant collagen-like proteins of the other four bacteria, and their purification and characterization were carried out.

Figure 3:
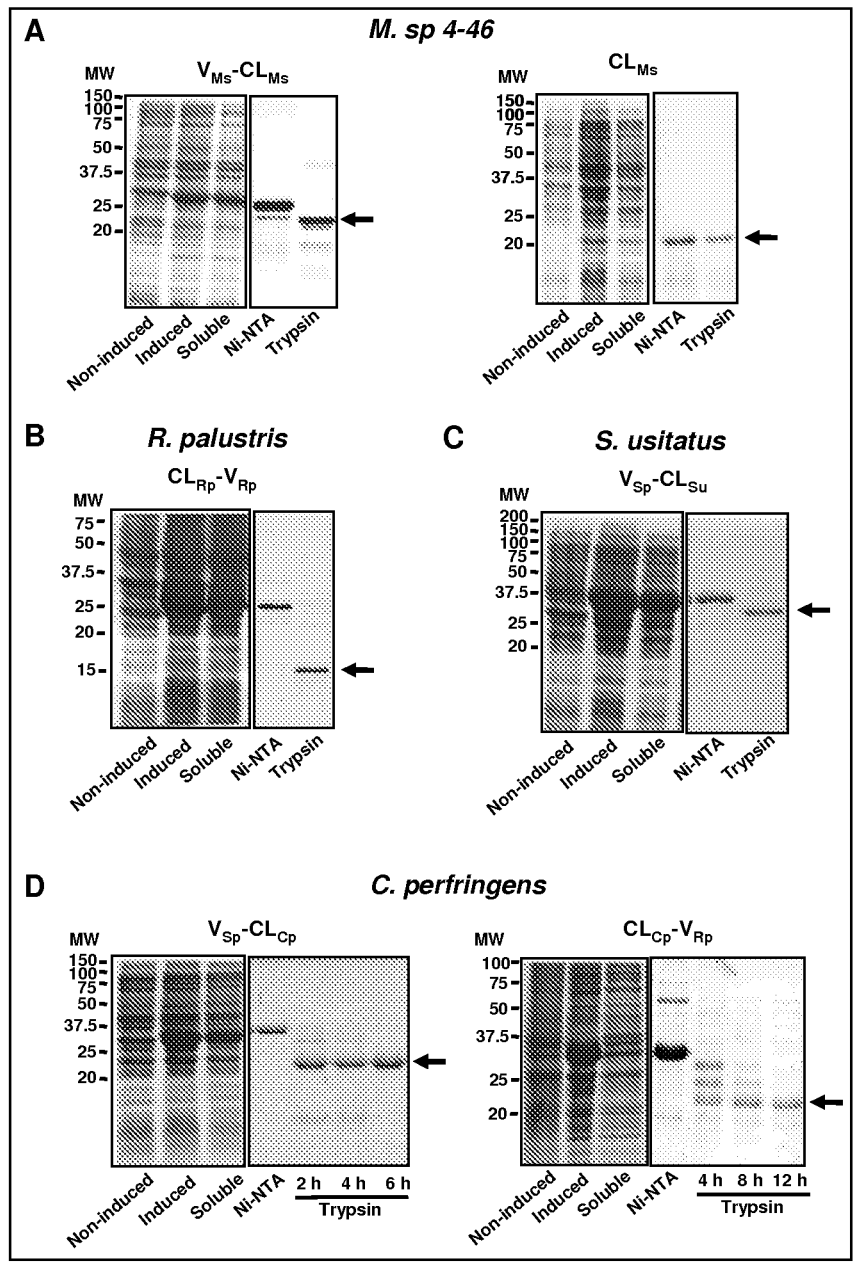
FIG. 3 illustrates expression of recombinant proteins in E. coli and resistance to trypsin digestion.

Cell fractionation indicated that the full-length proteins from three bacteria (*M. sp* 4-46, *S. usitatus* and *R. palustris*) were present in the soluble fraction (FIGS. 2 and 3). All recombinant protein constructs from *M. sp* 4-46 were soluble including the collagen domain alone. The recombinant protein from *R. palustris* was almost fully soluble as a full length construct or as CL$_{Rp}$ with the C-terminus (C)V$_{Rp}$, whereas protein from *S. usitatus* become more soluble after the deletion of the C-terminal domain. Partial solubility was seen for the other recombinant proteins constructs of *S. usitatus*. The protein from the *C. perfringens* was found in inclusion bodies (FIG. 2). Neither the CL$_{Cp}$ domain alone nor CL$_{Cp}$ with one or both of its terminal domains, were soluble.

Example 3

Formation of Chimeric Proteins to Promote Folding

Since insoluble proteins in inclusion bodies have been linked to misfolding, the insoluble CL$_{Cp}$ collagen domain was fused with two potential folding domains from the collagen proteins of other bacteria. In one construct, an additional C-terminal domain of *R. palustris*, $(C)V_{Rp}$ was attached to the $CL_{Cp}$ domain, in another, it was fused with a preceding N-terminal globular $(N)V_{Sp}$ domain of the Scl2 collagen-like protein from *S. pyogenes* (FIG. 2). Constructs containing $CL_{Cp}$ domain were now expressed in the soluble fraction, suggesting these additional chimeric domains were effective in facilitation of the correct assembly of the collagen-like domain from *C. perfringens*. There appears to be specificity in the location of the folding domains since the V domain of *R. palustris* promoted folding when on the C-terminal but not the N-terminal side of $CL_{Cp}$. Attachment of the $(N)V_{Sp}$ domain to the $CL_{Su}$ domain of *S. usitatus* also led to efficient production in the soluble fraction, suggesting proper protein assembly. No *C. diphtheria* protein induction was observed even after fusion of its CL domain with $(N)V_{Sp}$. Analysis of the protein samples by SDS PAGE is shown in FIG. 3.

Example 4

Trypsin Resistance of the Collagenous Domains

The collagen triple-helix confers resistance to digestion by trypsin as well as by other proteinases, and such enzyme digestion can be used to verify the presence of the triple-helix as well as to purify collagen domains. To probe the conformation of the expressed bacterial collagen constructs, recombinant proteins were purified from soluble fractions by affinity chromatography on Ni-NTA agarose and then digested with trypsin for different period of times at room temperature. The trypsin-digested products had mobilities expected for the isolated collagen triple-helix domains of the 4 bacterial proteins (FIG. 3), except for the mobility of the CL domain from *R. palustris* which was slightly slower than predicted. Mass spectroscopy confirmed the purity and molecular weight of the $(Gly-Xaa-Yaa)_n$ collagen domains of the proteins: 18,870.19 Da for $CL_{Cp}$; 21,667.53 Da for $CL_{Su}$; and 14,967.28 Da for $CL_{Ms}$. The size of the $CL_{Rp}$ was 13,335.87 Da, larger than the 11,275.48 Da theoretical value of the collagen domain alone, due to cleavage at an Arg site 24 amino acids into the N-terminal domain. Insertion of an Arg at the end of the CL domain is planned to obtain only the triple-helical fragment.

These results strongly suggest that soluble collagen-like proteins from four bacteria expressed in *E. coli* contain CL domains which are in a trypsin resistant triple-helical conformation. The conformation of the CL domains in non-soluble protein fractions was also approached using trypsin digestion. A significant portion of the inclusion bodies of the $(N)V_{Cp}$-$CL_{Cp}$ was digested by trypsin and no protease-resistant fragment corresponding by SDS-PAGE mobility to the CL domain was observed. These data support the conclusion that non-soluble recombinant proteins with collagen-like domains are likely to represent aggregates of misfolded protein.

Example 5

Circular Dichroism Spectroscopy: Conformation, Thermal Stability, and Refolding

CD spectra of purified $CL_{Su}$, $CL_{Rp}$ and $CL_{Cp}$ collagen domains obtained by trypsin digestion, as well as $CL_{Ms}$ expressed as only the collagenous domain gave typical collagen-like features at 4° C., with a maximum at 220 nm and a minimum near 198 nm (FIG. 4). It is difficult to obtain precise concentrations and mean residue ellipticity value for collagen domains which have no aromatic residues. The Rpn value (ratio of positive to negative peak) was used to estimate their triple-helix content. Values suggesting a fully triple-helical molecule (Rpn~0.11) were seen for the $CL_{Cp}$ and $CL_{Su}$. The lower Rpn value recorded for $CL_{Ms}$ and the negative value of the 220 nm peak for $CL_{Rp}$ suggest some perturbation to the triple helix or partial degradation (Table 2).

TABLE 2

Properties of the bacterial collagen-like recombinant proteins expressed in E. coli

| Bacteria | Recombinant Protein[a] | Trypsin Resistance[b] | $T_m$, ° C. | CD, Rpn[c] |
|---|---|---|---|---|
| C. perfringens | $V_{Sp}$-$CL_{Cp}$ | + | 39.6 | 0.13 |
| | $CL_{Cp}$-$V_{Rp}$ | + | 40.2 | |
| | $CL_{Cp}$[d] | + | 38.8 | |
| | $CL_{Cp}$, pH 2.2 | Nt[e] | 37.2 | |
| S. usitatus | $V_{Sp}$-$CL_{Su}$ | + | 39.4 | 0.11 |
| | $CL_{Su}$[d] | + | 38.5 | |
| | $CL_{Su}$, pH 2.2[d] | Nt | 27.0 | |
| M. sp 4-46 | $V_{Ms}$-$CL_{Ms}$ | + | 40.3 | 0.06 |
| | $CL_{Ms}$ | + | 35.0 | |
| | $CL_{Ms}$, pH 2.2 | Nt | 28.3 | |
| R. palustris | $CL_{Rp}$-$V_{Rp}$ | + | 37.5 | N/a[g] |
| | $CL_{Rp}$[d] | + | 37.0 | |
| | $CL_{Rp}$, pH 2.2[d] | Nt | 32.0 | |
| S. pyogenes[f] (Scl2) | $V_{Sp}$-$CL_{Sp}$ | + | 35.6 | 0.11 |
| | $CL_{Sp}$[d] | + | 35.9 | |
| | $CL_{Sp}$, pH 2.2[d] | Nt | 25.7 | |

Figure 4:
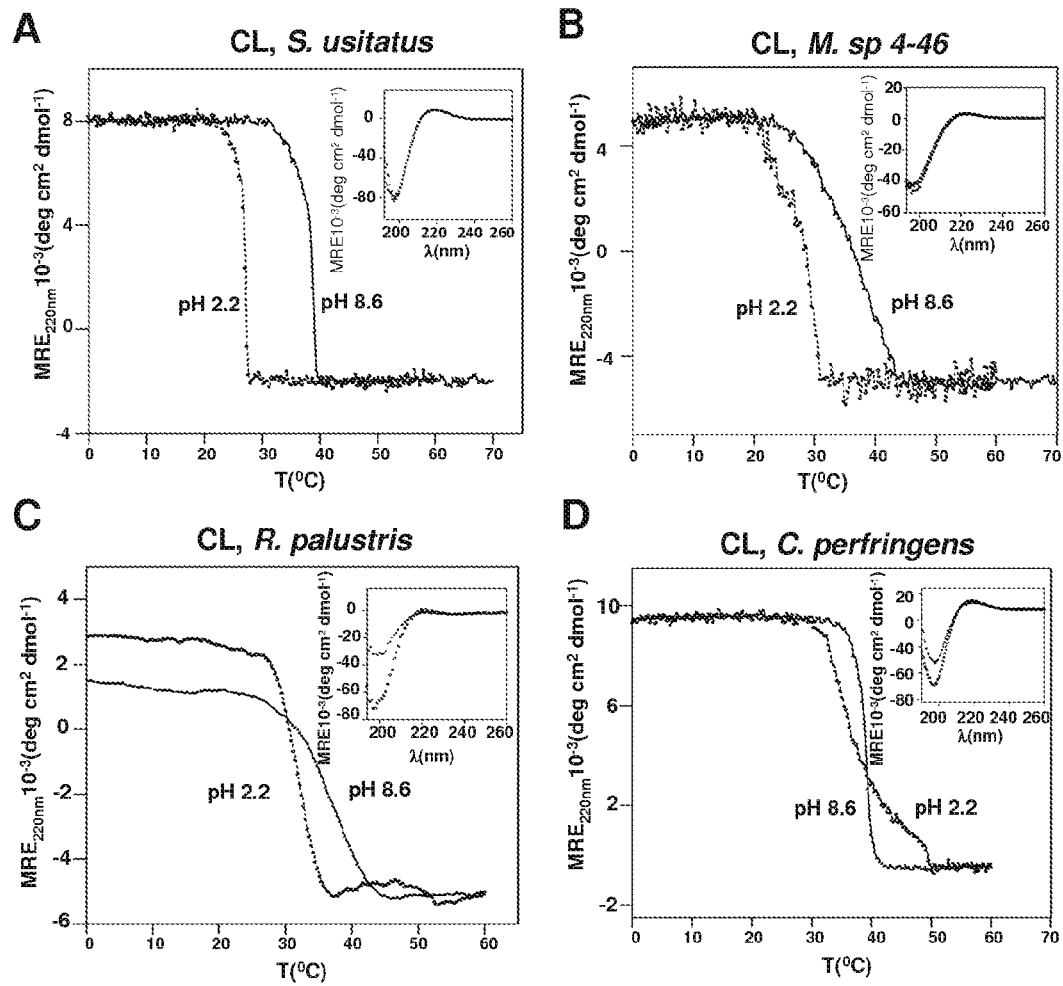
FIG. 4 provides thermal stability of the recombinant bacterial collagen-like domains.
Figure 5:
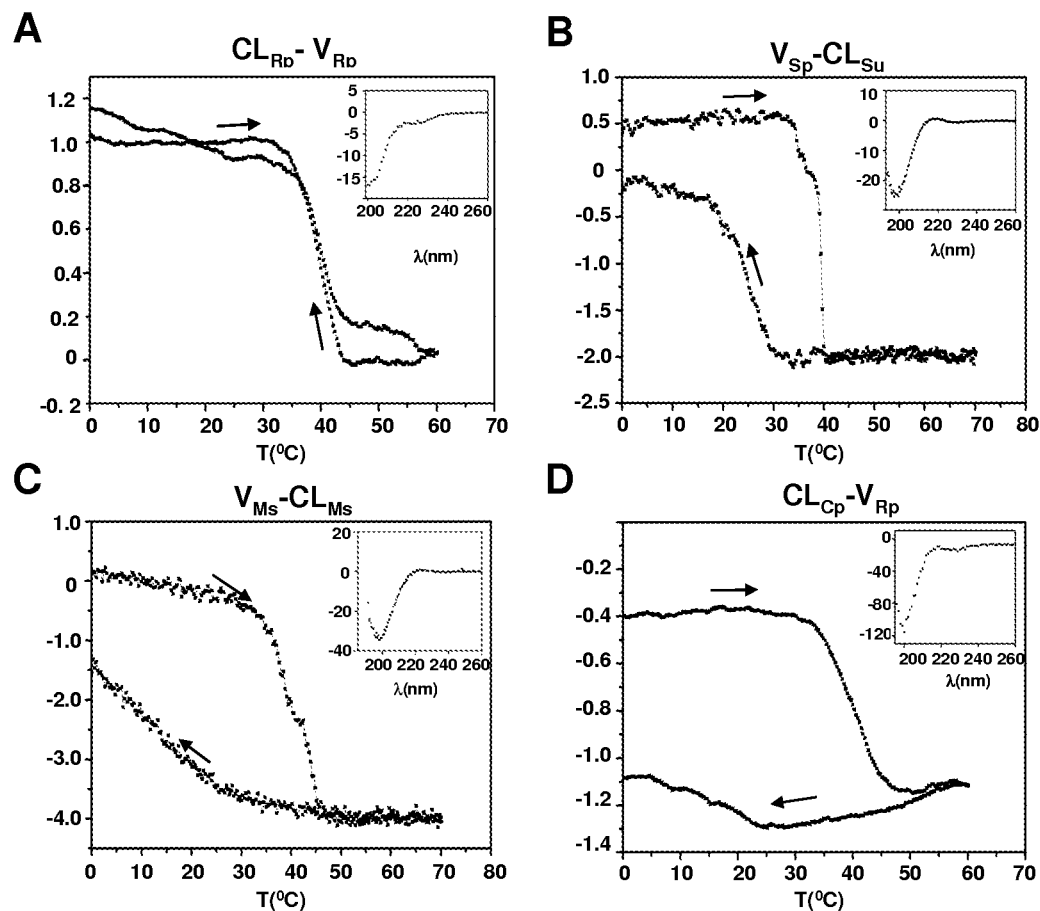
FIG. 5 provides thermal transitions of the recombinant proteins determined by the monitoring CD signal at 220 nm.

[a] $V_{Sp}$, N-terminal globular domain from S. pyogenes Scl2 protein; V, N-terminal domain from M. sp 4-46 protein; $V_{Rp}$, C-terminal domain from R. palustris protein; CL, collagen-like domain
[b] CL domain of the recombinant V-CL or CL-V proteins were resistant to the trypsin digestion
[c] Rpn is the ratio of the positive at 220 nm to the negative peak at 198 nm
[d] CL domains were purified by trypsin digestion
[e] not tested
[f] data for S. pyogenes Scl2 protein and its CL domain presented for comparison 12
[g] not available due to the negative value of the peak at 220 nm The CD spectra of proteins from single bacterial species, M. sp 4-46 (N)$V_{Ms}$-$CL_{Ms}$ and R. palustris $CL_{Rp}$-(C)$V_{Rp}$ as well as several chimeric proteins containing a CL domain from one bacteria together with a folding domain from another bacteria, $CL_{Cp}$-(C)$V_{Rp}$ and (N)$V_{Sp}$-$CL_{Su}$, have been studied. CD spectroscopy of all chimeric proteins and (N)$V_{Ms}$-$CL_{Ms}$ showed collagen-like features with a maximum at 220 nm and a minimum near 198 nm but with much lower magnitude than seen for isolated CL domains (FIGS. 4 and 5). The non-collagenous domains contribute to the spectrum and are likely cancel out some of the collagen-like signal. The R. palustris construct $CL_{Rp}$-(C)$V_{Rp}$ shows only a shoulder at 220 nm (FIG. 5), which is consistent with it having the shortest CL domain and the prediction of a helical coiled coil structure in the (C)$V_{rp}$ domain (85 residues) (FIG. 4).

Thermal unfolding of recombinant proteins was followed by monitoring the CD signal at 220 nm with increasing temperature (pH 8.6). Very sharp thermal transitions were observed for CL domains of S. usitatus and C. perfringens. Broader transitions were detected for the CL domains of the M. sp 4-46 and R. palustris (FIG. 4), which together with low Rpn values may suggest partial unfolding or heterogeneity of the material. $T_m$ values were in 35 to 39° C. range (Table 2). Slightly higher $T_m$ values were observed when collagenous domains were covalently attached to the folding domains compared with CL domains alone, indicating a relatively small stabilizing effect of the non-collagenous domains (FIG. 5). The only exception was M. sp 4-46, for which CL domain alone has almost 5° C. lower $T_m$ than the same protein with its own N-terminal folding domain (35.0° C. versus 40.3° C.).

CD spectra and melting curves were also obtained at pH 2.2, to compare with corresponding measurements at pH 8.6. CD spectra were similar at different pH values, but a significant decrease in thermal stability was observed at low pH for the $CL_{Su}$ ($T_m$=38.5 to 27° C.), $CL_{Ms}$ ($T_m$=40.3 to 28.3° C.) and $CL_{Rp}$ ($T_m$=37 to 32° C.) (FIG. 4, Table 2). It is also interesting to note that melting curves of the $CL_{Ms}$ and $CL_{Rp}$ were sharper upon melting at pH 2.2 than at pH 8.6. The three CL proteins which show a strong dependence of the stability from pH have a very high proportion of charged residues, constituting 34%, 34% and 35% of all Xaa, Yaa residues in (Gly-Xaa-Yaa) for $CL_{Ms}$, $CL_{Su}$ and $CL_{Rp}$, respectively. In contrast to the high pH dependent decrease in $T_m$ for the CL domains from the other three bacteria, only a slight decrease in the $T_m$ value (1.6° C.) was observed for CL from C. perfringens, which has the lowest charge content. Among three CL domains with high percentage of the charged residues, $CL_{Ms}$ and $CL_{Su}$ have almost equal quantity of negatively and positively charged residues, whereas $CL_{Rp}$ has 2.4 times more positively charged than negatively charged residues.

The ability of purified constructs to refold in vitro was investigated by monitoring the CD signal at 220 nm upon cooling of the samples from 70° C. to 0° C. at the same rate as heating (~0.1° C./min) (FIG. 5). CL domains isolated from all bacteria by trypsin digestion or by expression of the CL domain alone ($CL_{Ms}$) were not able to refold (data not shown). Most of the constructs with non-triple-helical domains adjacent to the CL domain showed recovery of some of the CD signal (FIG. 5A-D). The efficiency of refolding varied among the different constructs, with complete refolding in the case of the $CL_{Rp}$-$V_{Rp}$ and minimal refolding in the case $CL_{Cp}$-$V_{Rp}$ (See FIG. 5 wherein the → arrow indicates the direction of temperature change for the unfolding curve with increasing temperature and ← for the refolding curve with decreasing temperature). It is interesting that (C)$V_{Rp}$ domain was extremely effective in refolding its own CL domain but not in the refolding of the heterogeneous CL from C. perfringens.

Example 6

Chimeric Repeating Modules of the Collagen-Like Domain

A. Incorporating a Natural Break Between Repeat Collagen Residues

The expressed Scl2 protein as well as its isolated triple-helix domain form a stable triple-helix with $T_m$=36-37° C., close to the stability found in human collagens. A duplicate of the (Gly-X-Y)$_{79}$ was introduced into the cold shock vector, and a natural break found within non-fibrillar collagen was inserted between the tandem triple-helix modules to study the effect of the break on structure, stability, folding, flexibility and shape.

FIG. 6A provides a schematic of the design of the bacterial collagen Scl2.28 construct, showing the original $V_{Sp}$-$CL_{Sp}$ and duplicate $V_{Sp}$-$CL_{Sp}$-$CL_{Sp}$ constructed within a pColdIII-163 encoding p163 polypeptide based on Scl 2.28 with a His6 tag at the N-terminal end. A LVPRGSP (SEQ ID NO.: 1) sequence was inserted between the N-terminal globular domain (V) and collagen-like domain (CL) to act as a potential cleavage site for thrombin or trypsin. pColdIII-V-CL-CL was constructed based on an N-terminal V domain followed by a dimer of the (Gly-X-Y)$_{79}$ unit with two additional triplets between two CL domains. First, the globular domain of Scl2 (residues from Ala34 to Asp107) containing N-terminus His$_6$-tag and thrombin cleavage site, -LVPR↓GS-, is cloned into pColdV vector using NdeI and BamHI sites including three restriction sites, SmaI, ApaI, and BamHI. Using SmaI and ApaI sites from this cloned vector, PCR fragment having a blunt end and ApaI site is inserted. Note that Pro from SmaI will complete one triplet, GSP, after thrombin cleavage. This resultant construct has a His$_6$-tagged V domain and one bacterial (Gly-X-Y)$_{79}$ triple-helix domain followed by G1G break (GF) and one triplet, GPL (GP, from ApaI site). Importantly, the codon for Gly was changed from ggg for SmaI site to ggt in the PCR fragment. Therefore, this original SmaI site will be destroyed while the new SmaI site in the PCR product can be used. Next, using ApaI and BamHI sites, we will insert another PCR fragment having ApaI and BamHI sites. This resultant construct has a His$_6$-tagged V domain and two bacterial (Gly-X-Y)$_{79}$ triple-helix domains connected by a G1G break (GF). Various lengths and sequence of type IV breaks can be exchanged by using SmaI and ApaI sites in this construct.

Figure 11:
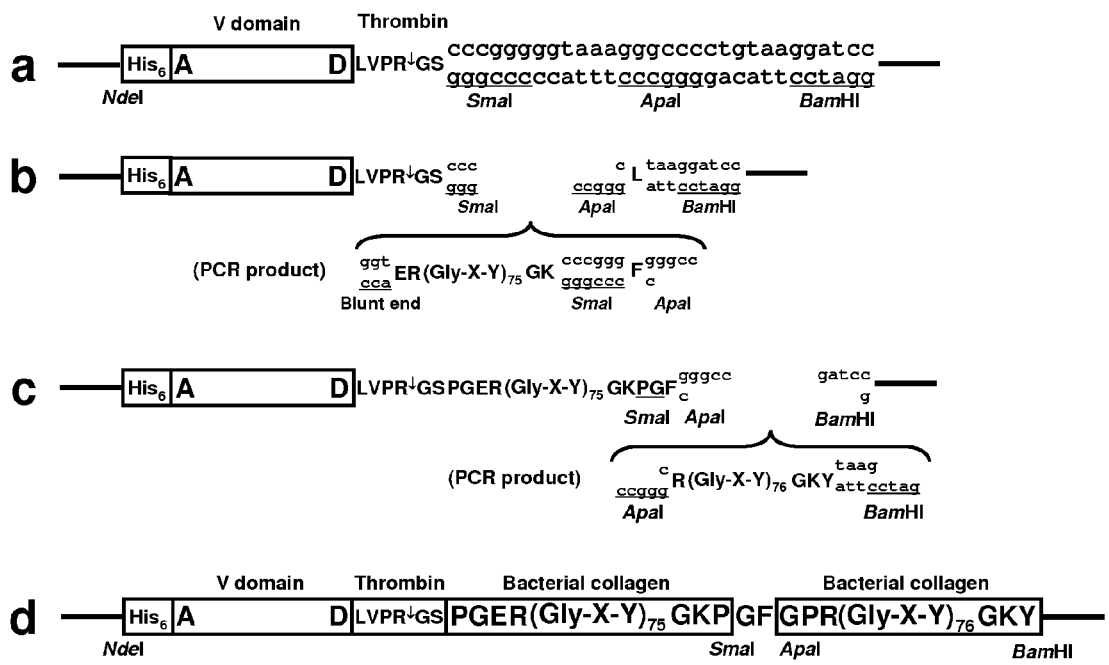
FIG. 11 provides a schematic of strategy for expression of bacterial collagen Scl2 globular V domain together with two triple-helix modules interrupted by a natural GFG break with (a) the vector including thrombin cleavage site and restriction enzyme sites, (b) the insertion of one collagen module into the vector; (c) the insertion of the second module into the vector; and (d) the final construct where the GF sequence can be replaced by other breaks using SmaI and ApaI sites.

The foregoing strategy for expression of bacterial collagen Scl2 globular V domain together with two triple-helix modules interrupted by a natural GFG break is schematically illustrated in FIG. 11 wherein section a illustrates a vector including thrombin cleavage site and restriction enzyme sites; section b illustrates the insertion of one collagen module into the vector; section c illustrates insertion of the second module into the vector; and section d illustrates the final construct where the GF sequence can be replaced by other breaks using SmaI and ApaI sites.

Referring to Table 3, below, different lengths and sequences of breaks also can be inserted instead of the GFG break. The oligonucleotides for each type IV break can be synthesized and inserted as a DNA fragment after annealing and digesting with SmaI and ApaI restriction enzymes. Other breaks can be taken from type VII collagen, because it is a homotrimer. A control triple-helix without any breaks was also expressed, inserting the integrin binding site GFOGER instead of a break sequence. This served as a control for all biophysical studies and can also be checked for integrin binding to confirm the biological effectiveness of the control triple-helix with two triple-helix modules. The expressed His-Tag bacterial constructs can be purified using a nickel column.

TABLE 3

Homotrimeric breaks to be introduced between two Scl2 bacterial collagen modules.

| Break | Sequence |
|---|---|
| No Break | (GXY)$_{79}$-(GXY)$_{79}$ |
| G1G | GFG from α5 (IV) |
| G4G | GAAVMG from α5 (IV) (SEQ ID NO.: 12) |
| G6G | GDSAVILG from α1 (VII) (SEQ ID NO.: 13) |
| G8G | GDMVVSRVKG from α4 (IV) (SEQ ID NO.: 14) |
| G9G | GPOGEFYFDLRLKGPOG from α1 (IV) (SEQ ID NO.: 50) |
| G12G | GRLVDTGPGAREKG from α1 (VII) (SEQ ID NO.: 16) |
| G15G | GQISEQKRPIDVEFQKG from α5 (IV) (SEQ ID NO.: 65) |
| G41G | GSVPNVDRLLETAGIKASALREIVETWDESSGSFLPVPERRRG from α1 (VII) (SEQ ID NO.: 17) |

B. Incorporation of Integrin Binding Domain

The 9-residue interruption GEFYFDLRLK (SEQ ID NO.: 15) may also be incorporated within the bacterial construct between the repetitive triple-helix modules, followed by expression of the polypeptide. This 9-residues sequence found within the triple-helix domain of alpha 1 chain of type IV collagen has been reported to bind to the alpha3 beta1 integrin on melanoma and ovarian carcinoma cells. Incorporation of this sequence within a triple-helix confers a high propensity towards molecular association and aggregation to form fibril structures. Constructs with this sequence may be useful for promoting fibril formation and for specific cell binding.

Figure 12:
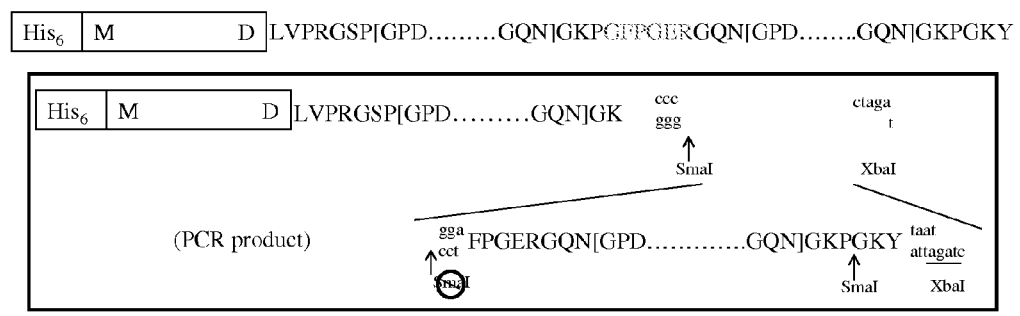
FIG. 12 provides a construct design for the introduction of the α2β1 integrin binding site, GFPGER, between triple helix modules.

Alternatively, the human type I collagen binding to site to α2β1 integrin, GFPGER (SEQ ID NO: 18), may be introduced between the repetitive Scl2 triple-helix modules, followed by expression of the polypeptide. The sequence coding for the four triplets in between the Scl2 triple-helix modules is modified to include GFPGER. FIG. 12 provides a construct design for the introduction of the α2β1 integrin binding site, GFPGER, between triple helix modules.

Expression of a polymer of the structure (Scl2)-GFPGER-(Scl2)-GFPGER-(Scl2)-GFPGER-(Scl2) provides proof of principle for introduction of other interaction sites. It is known that the integrin site does not require Hyp, and the sequences of the other sites do not contain Hyp. The cell binding properties of these polyScl constructs with multiple integrin binding sites can be characterized, in addition to their structural and tissue engineering features. The presence of multiple binding sites is important for individually weak binding sequences.

Expression of the polymer (Scl2)-GPRGQPGVMGFP-(Scl2) further confers binding to DDR2 receptors.

Example 7

Expression of Chimeric Repeating Modules of the Collagen-Like Domain in Cold-Shock System, Purification and Large-Scale Production A high-yield expression system was used to obtain the collagen-like proteins and its individual triple-helical domains of Example 6. Specifically, pColdIII-V$_{Sp}$-CL$_{Sp}$ and V$_{Sp}$-CL$_{Sp}$-CL$_{Sp}$ were expressed in the E. coli BL21 strain. Cells were grown in M9-casamino acid with ampicillin (50 µg ml$^{-1}$) medium at 37° C. until they reached A$_{600}$=0.8. The cultures were shifted at 15° C., room temperature and 37° C., respectively, and 1 mM isopropyl beta-D-thiogalactopyranoside was added to induce protein expression. After overnight incubation, cells were harvested by centrifugation. The distilled water and the SDS-PAGE buffer were added to the cells and they were boiled for one minute. The expression level at each temperature was analyzed by SDS-PAGE. SDS-PAGE was used to monitor the expression at different temperatures and indicated an expression level at room temperature much higher than at 15° C. or 37° C. (FIG. 6B). All further expression was carried out at room temperature (25° C.), using the advantage of the cold shock system.

For large-scale production of recombinant proteins E. coli BL21 cells harboring corresponding plasmids were inoculated into 5 mL of M9-casamino acid medium with Ampicillin (50 µg ml$^{-1}$) respectively and grown at 37° C. for 12 hours. The cultures were transferred to 1000 mL of M9-casamino acid medium and incubated until they reached A$_{600}$=1.2. Cells were harvested by centrifugation and dissolved by the two times concentrated L broth with Ampicillin (50 µg mL$^{-1}$). The each culture was shifted to a room temperature and 1 mM isopropyl beta-D-thiogalactopyranoside was added to induce protein expression. After overnight expression, cells were harvested by centrifugation and disrupted by a French press. Cellular debris was removed by centrifugation at 4° C. Each expressed protein was found in the supernatant as a soluble protein. The supernatant was loaded onto a Ni-sepharose resin column (25 mL bed volume) (GE Healthcare) equilibrated with the binding buffer (20 mM phosphate buffer (pH 7.4) containing 500 mM NaCL and 25 mM imidazole) at room temperature. After being washed with the binding buffer, the proteins were eluted using the eluting buffer (the binding buffer with 58 mM, 96 mM, 115 mM, and 400 mM imidazole) by stepwise eluting. The VCLs and VCL-CL were eluted with 96 mM and 115 mM imidazole. The protein purity was checked by SDS-PAGE. The yields of purified protein were in the range of 400 mg/L of 2×L broth and the bands of His-VCLs were observed at expected for each protein position.

Example 8

Cleavage and Purification of Collagen (Gly-Xaa-Yaa)$_n$ Domain with Trypsin

The collagen-like triple-helix domains of $V_{Sp}$-$CL_{Sp}$ and $V_{Sp}$-$CL_{Sp}$-$CL_{Sp}$ were isolated from the expressed bacterial collagen product by treating with trypsin since triple-helix domains are known to be resistant in their native state. 10 mg of purified VCLs were dialysed against 50 mM glycine buffer (pH 8.6) then digested with 1/1000 (w/w) trypsin at room temperature. The digested products were loaded onto a DEAE Sephadex anion exchange column at room temperature. The fractions containing collagen-like sequences were further purified using a Superdex™ 200 gel filtration column (GE Healthcare). Protein purity was checked by SDS-PAGE and MALDI-TOF mass spectrometry. To test whether the purified molecules were still a triple-helix or denatured into three single helices, trypsin digestion was carried out. After incubation for 1 hour at 25° C. and 37° C. (above Tm), respectively, proteins were digested with 1/100 (w/w) trypsin at 25° C. The result showed that all recombinant proteins were still triple-helical.

Figure 6C:
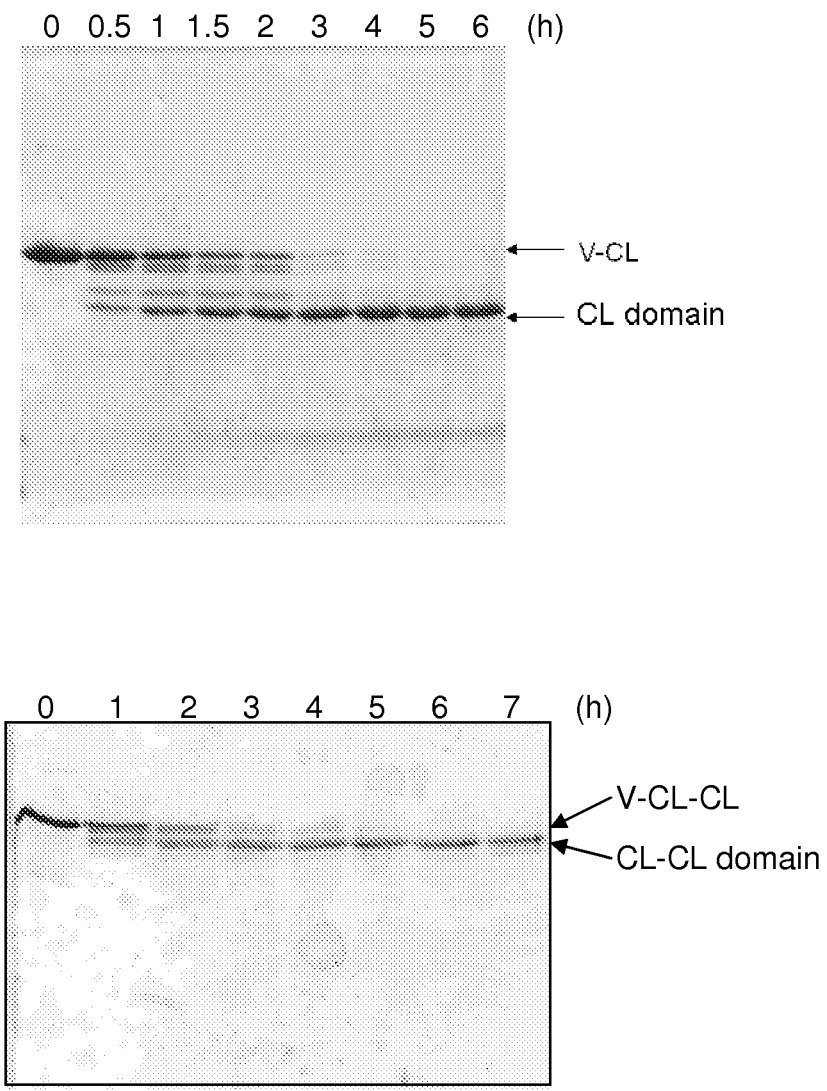
FIG. 6C provides time course of the digestion of $V_{Sp}$-$CL_{Sp}$ and $V_{Sp}$-$CL_{Sp}$-$CL_{Sp}$ by trypsin at room temperature for different length of time in hours, with products applied to SDS-PAGE.

FIG. 6C provides time course of the digestion of $V_{Sp}$-$CL_{Sp}$ and $V_{Sp}$-$CL_{Sp}$-$CL_{Sp}$ by trypsin at room temperature for different length of time in hours, with products applied to SDS-PAGE.

Figure 6D:
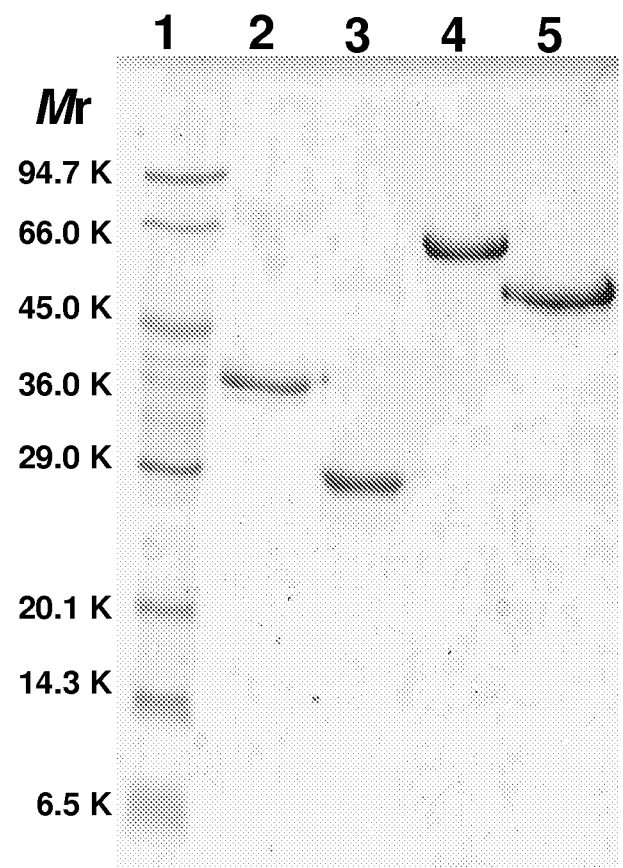
FIG. 6D provides SDS-PAGE of purified proteins $V_{Sp}$-$CL_{Sp}$, $CL_{Sp}$, $V_{Sp}$-$CL_{Sp}$-$CL_{Sp}$ and $CL_{Sp}$-$CL_{Sp}$ with column 1 providing a Molecular weight marker, column 2 providing $V_{Sp}$-$CL_{Sp}$, column 3 providing $CL_{Sp}$, column 4 providing $V_{Sp}$-$CL_{Sp}$-$CL_{Sp}$ and column 5 providing $CL_{Sp}$-$CL_{Sp}$.
Figure 7:
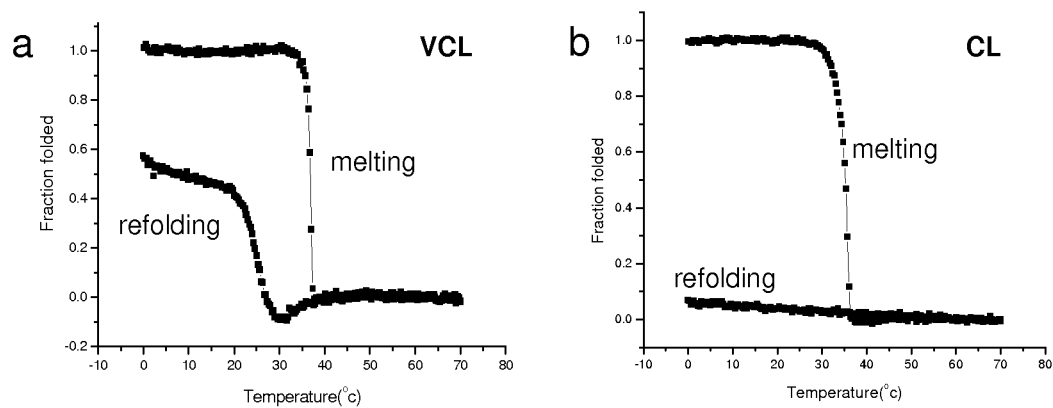
FIGS. 7A-D provide the thermal transition of the $V_{Sp}$-$CL_{Sp}$, $CL_{Sp}$, $V_{Sp}$-$CL_{Sp}$-$CL_{Sp}$ and $CL_{Sp}$-$CL_{Sp}$ constructs determined by monitoring CD signal at 220 nm.
Figure 7:
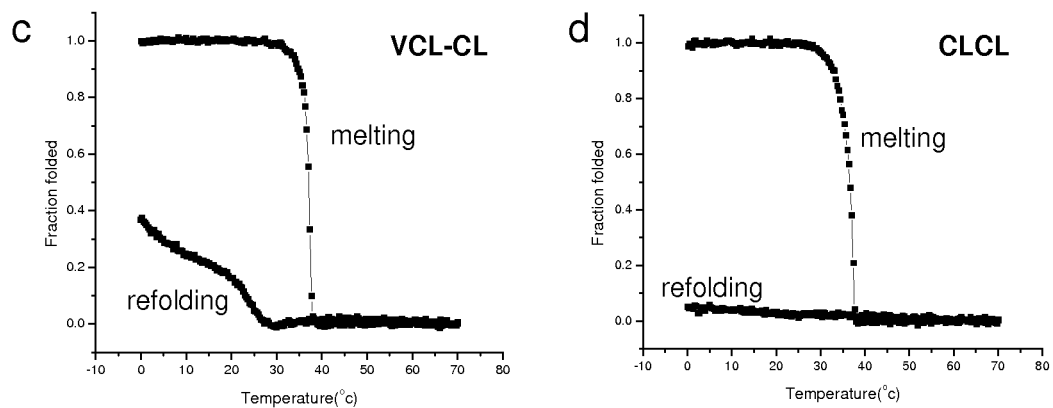

FIG. 6D provides SDS-PAGE of purified proteins $V_{Sp}$-$CL_{Sp}$, $CL_{Sp}$, $V_{Sp}$-$CL_{Sp}$-$CL_{Sp}$ and $CL_{Sp}$-$CL_{Sp}$ with column 1 providing a Molecular weight marker, column 2 providing $V_{Sp}$-$CL_{Sp}$, column 3 providing $CL_{Sp}$, column 4 providing $V_{Sp}$-$CL_{Sp}$-$CL_{Sp}$ and column 5 providing $CL_{Sp}$-$CL_{Sp}$. $V_{Sp}$-$CL_{Sp}$-$CL_{Sp}$ showed an SDS-PAGE band around 56 kDa as expected, and mass spectroscopy gave a mass of 55800, which is comparable to the theoretical value, 55701. Mass spectrometry analysis of the purified $CL_{Sp}$ protein was 22850, in good agreement with the predicted molecular mass of 22840. On SDS PAGE, the $CL_{Sp}$ band was higher than expected, which is common for rod-like triple-helix proteins (FIG. 6d). The dimer collagen domain, $CL_{Sp}$-$CL_{Sp}$, was also isolated using trypsin and purified as described above. Mass spectrometry of $CL_{Sp}$-$CL_{Sp}$ showed 44938, which is in good agreement with the expected value of 44998. These result were furthered demonstrated by circular dichroism (CD) spectroscopy, discussed below.

Example 9

Characterization of Conformation, Stability, and Other Biophysical Properties of Expressed Constructs of Example 6

A. Circular Dichroism (CD) Spectroscopy

To investigate conformational features, circular dichroism spectroscopy (CD) was carried out on the intact $CL_{Sp}$ duplicate protein and its isolated collagenous domain. The CD spectrum of $V_{Sp}$-$CL_{Sp}$ in PBS buffer at pH 7 shows typical collagen features, with a maximum at 220 nm and a minimum at 198 nm (Table 4). This pattern is typical for collagen but the absolute peak intensities at both 220 nm and 198 nm are less than pure collagen triple-helix because of the presence of a globular V-domain, which gives a negative value at 220 nm and a positive value at 198 nm.

When the purified $CL_{Sp}$ domain is examined, the CD peaks are at similar locations but with much higher intensities. Accurate concentration values could not be determined for the CL domain which has no aromatic residues, but concentration estimates by weight lead to an estimated MRE220 ~8000 deg·cm2·dmol-1 (Table 4), a value even higher than seen for animal collagens. The parameter Rpn, which is the ratio of the intensity of the positive peak near 220 nm over the intensity of the negative peak near 198 nm, has been shown to be a useful measure of the collagen triple-helix conformation. The Rpn for the isolated $CL_{Sp}$ domain is 0.128, which is very close to the 0.13 Rpn value observed for animal collagens, indicating the collagenous $CL_{Sp}$ domain forms a fully folded triple-helix.

The CD spectrum of only the globular domain showed two negative peaks at about 208 nm and 225 nm ($MRE_{208}$=−17400 deg·cm$^2$·dmol$^{-1}$; $MRE_{225}$=−16800 deg·cm$^2$·dmol$^{-1}$), which are characteristic of alpha helix. And it also shows a positive value at 198 nm ($MRE_{198}$=17000 deg·cm$^2$·dmol$^{-1}$). This pattern suggests that the globular domain is largely alpha-helical, consistent with the prediction of high coiled-coil possibility for residues 10-30 and 55-70 in this globular domain. Subtraction of the CD signals of globular domain from total $V_{Sp}$-$CL_{Sp}$ CD signals gives an estimate that $CL_{Sp}$ domain has a higher MRE at 220 nm ($MRE_{220}$=7800 deg·cm$^2$·dmol$^{-1}$) than mammalian collagen.

The $V_{Sp}$-$CL_{Sp}$-$CL_{Sp}$ protein has a positive peak at 220 nm and a negative peak at 198 nm, with an estimated MRE 222 of ~8000 deg·cm2·dmol-1 (Table 3), and the purified $CL_{Sp}$-$CL_{Sp}$ dimer has an Rpn around 0.114, again indicating a fully triple-helical molecule. FIG. 7A-D provides the thermal stability of $V_{Sp}$-$CL_{Sp}$, $V_{Sp}$-$CL_{Sp}$-$CL_{Sp}$ and the isolated $CL_{Sp}$ and $CL_{Sp}$-$CL_{Sp}$ domains were examined by monitoring the change in the CD peak at 220 nm with increasing temperature. Very sharp thermal transitions are observed for all samples, with values of Tm=36.8° C. for $V_{Sp}$-$CL_{Sp}$, Tm=37.1° C. for $V_{Sp}$-$CL_{Sp}$-$CL_{Sp}$, Tm=35.2° C. for $CL_{Sp}$ and Tm=36.5° C. for $CL_{Sp}$-$CL_{Sp}$. The increased length of the collagenous domain appears to cause only a slight increase in thermal stability. The presence of a single sharp transition for $V_{Sp}$-$CL_{Sp}$ and $V_{Sp}$-$CL_{Sp}$-$CL_{Sp}$ at the same $T_m$ values as $CL_{Sp}$ and $CL_{Sp}$-$CL_{Sp}$ indicates the $V_{Sp}$ domain unfolds simultaneously with the collagenous domain under these conditions. The ability of the proteins to refold after heat denaturation was also examined (see reverse arrows in FIG. 7), by monitoring the CD signal at 220 nm as the sample is cooled at same rate as the heating rate. A substantial amount of their original CD signal is regained by $V_{Sp}$-$CL_{Sp}$ (60%) and $V_{Sp}$-$CL_{Sp}$-$CL_{Sp}$ (40%) upon cooling from 70° C. to 0° C., and the initial drop in the 220 nm signal could represent the refolding of the $V_{Sp}$ globular domain prior to triple-helix folding. In contrast, no signal is regained upon cooling of the $CL_{Sp}$ and $CL_{Sp}$-$CL_{Sp}$ proteins. These results indicate that the globular $V_{Sp}$ domain is important for refolding and is likely to act as a trimerization domain necessary for triple-helix formation.

TABLE 4

Physical properties of bacterial collagen

|  | Rh(nm) | CD Tm (° C.) | MRE$_{198}$ (deg · cm$^2$ · dmol$^{-1}$) | MRE$_{220}$ | Rpn | DSC Tm(° C.) | ΔH$_{cal}$ (kJ/mol) |
|---|---|---|---|---|---|---|---|
| V$_{Sp}$-CL$_{Sp}$ | 10.2 ± 1.1 | 36.8 | −38400 | 1500 | 0.04 | 37.9 | 2730 |
| CL$_{Sp}$ | 8.0 ± 1.6 | 35.2 | −62500 | 8000 | 0.13 | 37.0 | 2820 |
| V$_{Sp}$-CL$_{Sp}$-CL$_{Sp}$ | 49.6 ± 22.4 | 37.1 | −54500 | 5400 | 0.10 | 37.5 | 4290 |
| CL$_{Sp}$-CL$_{Sp}$ | 17.0 ± 1.1 | 36.5 | −53500 | 6100 | 0.11 | 37.9 | 5300 |

B. Differential Scanning Calorimetry (DSC)

Figure 8:
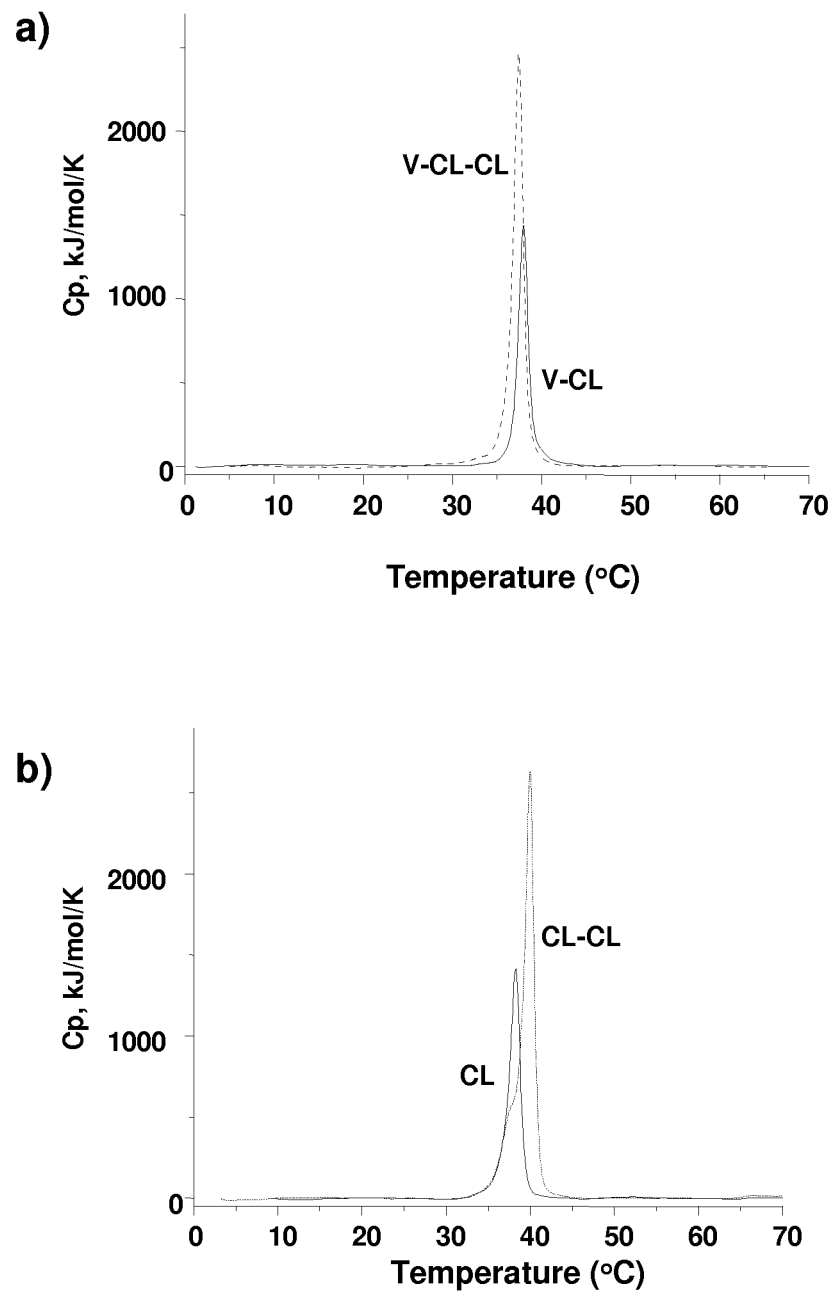
FIGS. 8A-B provides the DSC of $V_{Sp}$-$CL_{Sp}$, $CL_{Sp}$, $V_{Sp}$-$CL_{Sp}$-$CL_{Sp}$ and $CL_{Sp}$-$CL_{Sp}$.

DSC experiments were recorded on a NANO DSC II Model 6100 (Calorimetry Sciences Corp). DSC was used to determine the thermal stability and calorimetric enthalpy of bacterial collagen. The samples were dialyzed against phosphate-buffered saline (pH 7.0). Sample solutions were loaded at 0° C. into the cells and heated at a rate of 1° C./min. Enthalpy was calculated from first scan because the scans were not reversible upon cooling. FIG. 8 A-B provides the thermal transitions seen by DSC for the V$_{Sp}$-CL$_{Sp}$, V$_{Sp}$-CL$_{Sp}$-CL$_{Sp}$, CL$_{Sp}$ and CL$_{Sp}$-CL$_{Sp}$ proteins. DSC experiments were recorded on a NANO DSC II Model 6100 (Calorimetry Sciences Corp). Each sample was dialyzed against phosphate-buffered saline (pH 7.0). Sample solutions were loaded at 0° C. into the cell and heated at a rate of 1° C./min. The enthalpy was calculated from the first scan because the scans were not reversible upon cooling. DSC for the V$_{Sp}$-CL$_{Sp}$, V$_{Sp}$-CL$_{Sp}$-CL$_{Sp}$, CL$_{Sp}$ and CL$_{Sp}$-CL$_{Sp}$ proteins at 37.5-37.9° C. are very similar to those seen by CD spectroscopy. DSC showed very similar thermal transition values for monomer, with and without globular domain. The scan of V$_{Sp}$Cl$_{Sp}$ showed single transition at 37.9° C. with a calorimetric enthalpy of ΔH$_{cal}$=2727 kJ/mol. The T$_m$ of DSC is almost 1° C. higher than the 36.8° C. of the CD, due to the faster heating rate under non-equilibrium conditions. The CL$_{Sp}$ showed single transition at 37.0° C. with a calorimetric enthalpy of ΔH$_{cal}$=2820 kJ/mol. The transition value is also higher than the 35.2° C. of the CD. The CL$_{Sp}$-CL$_{Sp}$ peak shows a small shoulder that is likely due to some heterogeneity in the digestion products. The high calorimetric enthalpy values support an extensive hydration network for the bacterial collagen products, similar to that seen for animal collagens and model peptides.

All samples were dialyzed against phosphate-buffered saline (pH 7.0) and then centrifuged and filtered through 0.1 μm Whatman Anotop filters before measurements. To obtain the hydrodynamic radius (R$_h$), the intensity autocorrelation functions were analyzed by Dynamic software (Wyatt Technologh Corp).

Example 10

Characterization of Solubility/Precipitation of Expressed Proteins and the Example 6 Higher Order Structures Formed by them (Fibers)

A. Solubility Study

The purified V$_{Sp}$-CL$_{Sp}$, CL$_{Sp}$, V$_{Sp}$-CL$_{Sp}$-CL$_{Sp}$ preparations, and bovine skin collagen were dialyzed at 4° C. for 24 h against four different buffers: 0.1M acetic acid (pH 2.9) at 4° C.; 50 mM sodium acetate buffer (pH 5.0), phosphate-buffered saline (pH 7.0) and 50 mM glycine buffer (pH 8.6). These samples were also dialyzed at 24° C. against all buffers except for acetic acid, where the V$_{Sp}$-CL$_{Sp}$ and CL$_{Sp}$ proteins were shown to denature at this temperature. The CL$_{Sp}$-CL$_{Sp}$ protein was dialyzed against PBS at 4° C., 24° C., and 30° C. for 24 h, and also against 0.1M acetic acid at 4° C. After dialysis, each sample was centrifuged at 14000 rpm for 10 min to remove insoluble materials. Solubility was determined by measuring the concentration in the supernatant, using the Tyr extinction coefficient of ε275=9635 M-1 cm-1 for V$_{Sp}$-CL$_{Sp}$ and V$_{Sp}$-CL$_{Sp}$-CL$_{Sp}$ and using the CD spectrum for CL$_{Sp}$, CL$_{Sp}$-CL$_{Sp}$ and bovine skin collagen assuming a mean residue ellipticity of MRE 220=6000 deg cm2 dmol-1. Lyophilyzed pepsin—treated bovine skin collagen was dissolved in 0.1 M acetic acid and stirred for 12 h at 4° C. After spinning down at 14,000 rpm for 10 min to remove the cross-linked collagen, the sample was used for solubility studies.

TABLE 5

Solubility of bovine skin collagen and bacterial collagen (1 mg/ml) in different buffers and pH

|  | 0.1M acetic acid pH 2.9 | | 50 mM sodium acetate pH 5.0 | | PBS pH 7.0 | | | 50 mM glycine NaOH pH 8.6 | |
|---|---|---|---|---|---|---|---|---|---|
| Protein | 4° C. % | 24° C. | 4° C. % | 24° C. | 4° C. | 24° C. % | 30° C. | 4° C. % | 24° C. |
| Bovine skin collagen | 100 | NDa) | 65.9 | 67.5 | 98.1 | 93.7 | 54.0 | 0 | 0 |
| V$_{Sp}$-CL$_{Sp}$ | 98.1 | NDa) | 76.5 | 70.6 | 66.0 | 69.6 | ND | 100 | 100 |
| CL$_V$ | 100 | NDa) | 83.6 | 84.9 | 100 | 80.0 | ND | 100 | 87.5 |
| V$_{Sp}$-CL$_{Sp}$-CL$_{Sp}$ | 100 | NDa) | 79.4 | 84.4 | 80.0 | 92.7 | ND | 75.0 | 82.3 |
| CL$_{Sp}$-CL$_{Sp}$ | 100 | NDa) | ND | ND | 100 | 63.6 | 65.6 | ND | ND |

Figure 9:
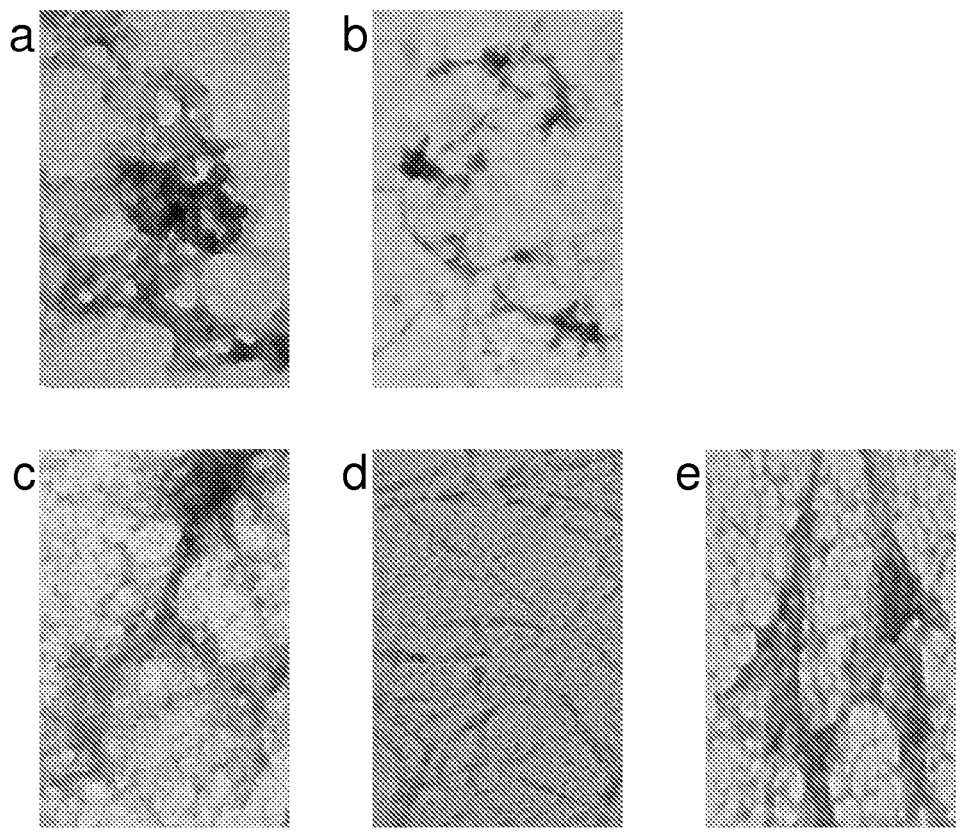
FIG. 9 provides electronic microscopy of the precipitates in PBS with negative staining for $V_{Sp}$-$CL_{Sp}$, $CL_{Sp}$ domain, $V_{Sp}$-$CL_{Sp}$-$CL_{Sp}$ and $CL_{Sp}$-$CL_{Sp}$ domains at 4° C. and positive staining for $CL_{Sp}$-$CL_{Sp}$ domains at 25° C.

At high enough concentrations (>2 mg/ml) bacterial collagen products showed some precipitates in PBS at 4° C. which were examined by transmission electron microscopy. FIG. 9 provides electronic microscopy of the precipitates in PBS (a-d) negative staining for V$_{Sp}$-CL$_{Sp}$, CL$_{Sp}$ domain, V$_{Sp}$-CL$_{Sp}$-CL$_{Sp}$ and CL$_{Sp}$-CL$_{Sp}$ domains at 4° C. positive staining for CL$_{Sp}$-CL$_{Sp}$ domains at 25° C. Precipitates of V$_{Sp}$-CL$_{Sp}$, CL$_{Sp}$, V$_{Sp}$-CL$_{Sp}$-CL$_{Sp}$ and CL$_{Sp}$-CL$_{Sp}$ were analyzed under an electron microscope after negative staining. V$_{Sp}$-CL$_{Sp}$ precipitates appeared as poorly ordered clusters with some indication of underlying fibrous nature, while the $CL_{Sp}$ precipitate showed fibrillar structures with a diameter of 9.0 nm±6.3 nm. The precipitates of $V_{Sp}$-$CL_{Sp}$-$CL_{Sp}$ appear to have a fibrous nature, with branching and irregularities, while the precipitates of $CL_{Sp}$-$CL_{Sp}$ form more regular and longer fibrils with a diameter of 21.0 nm±6.7 nm. Some of the $CL_{Sp}$-$CL_{Sp}$ fibrous structures show some suggestion of periodic nodes at about 100 nm intervals.

B. Segment Long Spacing Crystallites

To form SLS aggregates, 0.2 mg/mL of $V_{Sp}$-$CL_{Sp}$ and 0.1 mg/mL of $CL_{Sp}$, $V_{Sp}$-$CL_{Sp}$, and $CL_{Sp}$ were dialyzed at 4° C. first against 0.5 M acetic acid and then against 0.2% ATP in 0.01 M acetic acid for two days. Samples were taken on carbon-coated grids, positively stained with 0.4% phosphotungstic acid, and examined with JEOL 1200EX electron microscope (Broek, Daniel L. and Brodsky, B., JBC 1985).

Figure 10:
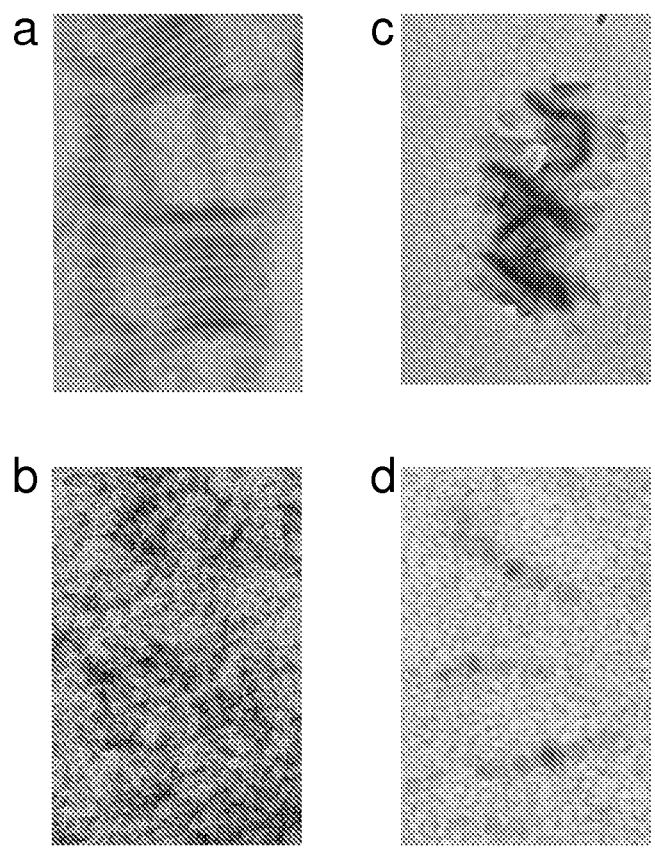
FIG. 10 provides the electron micrographs of samples prepared to form Segment Long Spacing (SLS) crystallites of collagen (dialysis against ATP, pH 3), with FIG. 10a providing Bovine skin collagen type I, FIG. 10b providing $V_{Sp}$-$CL_{Sp}$, FIG. 10c providing $CL_{Sp}$ domain and FIG. 10d providing $V_{Sp}$-$CL_{Sp}$-$CL_{Sp}$.

FIG. 10 provides the electron micrographs of samples prepared to form Segment Long Spacing (SLS) crystallites of collagen (dialysis against ATP, pH 3), with FIG. 10a providing Bovine skin collagen type I, FIG. 10b providing $V_{Sp}$-$CL_{Sp}$, FIG. 10c providing $CL_{Sp}$ domain and FIG. 10d providing $V_{Sp}$-$CL_{Sp}$-$CL_{Sp}$. Samples were taken on carbon-coated grids, positively stained with 0.4% phosphotungstic acid, and examined with a Philips CM12 electron microscope. In contrast to the 300 nm length crystallites with clear banding seen for bovine collagen, the $V_{Sp}$-$CL_{Sp}$ protein forms small narrow fibrous aggregates with an average length of 132±27 nm. Since this length represents almost twice the length expected for the collagenous domain (67.8 nm), and the globular domain was previously shown to have a diameter of approximately 3.9 nm, it is possibly that the aggregates observed are formed by two antiparallel molecules combined through their globular domains lined up in parallel arrays. Dialysis of the isolated collagen domain $CL_{Sp}$ against ATP formed a network like structure with little indication of SLS-like parallel packing or banding. The SLS crystallite preparations of $V_{Sp}$-$CL_{Sp}$-$CL_{Sp}$ show discrete aggregates with 6-7 bands along their length. The length of the crystallites clusters around two sizes 182±5 and 363±11 nm. Given the expected dimensions of the $CL_{Sp}$-$CL_{Sp}$ domain as 140 nm and the V domain as 3.9 nm, it is possible that the 180 nm crystallites are formed by an array of parallel single molecules of $V_{Sp}$-$CL_{Sp}$-$CL_{Sp}$ while the 360 nm crystallites are formed by two antiparallel molecules of $V_{Sp}$-$CL_{Sp}$-$CL_{Sp}$ joined at their globular domains, which may represent the central dark band in the larger crystallites.

C. Analysis by Microscopy

The precipitates of $V_{Sp}$-$CL_{Sp}$, $CL_{Sp}$, $V_{Sp}Cl_{Sp}$-$CL_{Sp}$, and $CL_{Sp}$-$CL_{Sp}$ were analyzed by negative staining and electron microscopy. (FIG. 10a-b) The precipitates were obtained after dialyzing against PBS and centrifuged at 14,000 rpm for 10 minutes. After diluting the precipitates with the buffer, the 5 µl samples were adsorbed onto carbon-coated grids for 30 seconds and stained for 5 seconds on 1 drop of 0.5% uranyl acetate for analyzing electron microscopy. The grids were dried at room temperature. Specimens were observed in JEOL 1200EX electron microscope. Images were recorded with Philips CM12.

Segment long spacing crystallites arise by lateral aggregation of collagen molecules in register, and the staining of charged residues produces a positive banding pattern visible in the electron microscope. (FIG. 10a-c) The SLS crystallites obtained with of the bovine skin collagen gave the typical appearance, with is approximately 300 nm. The appearance of the bacterial is very different. The SLS aggregates from the $V_{Sp}CL_{Sp}$ have approximately 150 nm with the quite different banding pattern from the bovine skin collagen (FIG. 10a). The measured length of 150 nm showed almost twice of 71.7 nm, which is calculated value of the collagenous domain (67.8 nm) and globular domain (3.9 nm) (Yi Xu et al. JBC 2002). The width of dark band is much wider than that of the bovine and the total length and width (around 10 nm) is greater than the bovine. According to the length, it is possible that the $V_{Sp}Cl_{Sp}$-$CL_{Sp}$ crystallites were formed by the dimer that combines with each globular domain. The SLS crystallites from $CL_{Sp}$ did not show the banding pattern.

Example 11

Incorporation of Matrix Metalloproteinase Cleavage Site

Matrix metalloproteinases (MMPs) are zinc-dependent endopeptidases and they are capable of degrading all kinds of extracellular matrix proteins. MMPs are thought to play a major role on cell behaviors such as cell proliferation, migration, differentiation, angiogenesis, apoptosis and host defense. In the vertebrate MMP family, there are four collagenases, namely MMP-1, MMP-8, MMP-13 and MMP-18. These collagenases cleave type I, II and III collagens at a site one-fourth from C-terminus. And there are also two gelatinases, namely MMP-2 and MMP-9. They cleave the denatured collagens. And MMP-2 also cleaves type I, II and III collagens. The most frequent sequence of cleavage site is G-P-Q(L)-G-I(L)-A(L) (SEQ ID NOS: 19-26). The MMP cleaves after the Glycine underlined. The definition of the residue positions is as follows.

-G-P-Q(L)-G-I(L)-A(L)-        (SEQ ID NOS: 19-26)

A MMP Cleavage Model (Fields, 1991)

a) high imino acid (>33%)-containing region that is tightly triple-helical, consisting of four G-X-Y triplets preceding the cleavage site, but in subsite $P_2$ there cannot be an imino acid b) low imino acid (<17%)-containing, loosely triple-helical region consisting of four G-X-Y triplets following the cleavage site c) a maximum of one charged residue for the entire 25 residue cleavage site region, which is always an Arg in subsites $P_{5'}$ or $P_{8'}$.

d) a low side-chain molar volume e) at least 12 residues from subsites $P_4$-$P_{8'}$.]

V-CL Protein from *Streptococcus pyogenes* as a Background

Sequence of V-CL

V domain:
(SEQ ID NO: 66)
MNHKVHMHHHHHHDEQEEKAKVRTELIQELAQGLGGIEKKNFPTLGDE

DLDHTYMTKLLTYLQEREQAENSWRKRLLKGIQDHALDLVPR

CL domain:
(SEQ ID NO: 7)
GSPGLPGPRGEQGPTGPTGPAGPRGLQGLQGLQGERGEQGPTGPAGPR

GLQGERGEQGPTGLAGKAGEAGAKGETGPAGPQGPRGEQGPQGLPGKD

GEAGAQGPAGPMGPAGERGEKGEPGTQGAKGDRGETGPVGPRGERGEA

GPAGKDGERGPVGPAGKDGQNGQDGLPGKDGKDGQNGKDGLPGKDGKD

GQNGKDGLPGKDGKDGQDGKDGLPGKDGKDGLPGKDGKDGQPGKPGKY

There are four potential collagenase cleavage sites in this sequence as underlined. But none of them is strictly identical to the MMP cleavage site in types I, II, and III collagens, that is, G-P-Q(L)-G-I(L)-A(L) (SEQ ID NOS: 19-26). And the second and the third cleavage sites are too close to each other to serve as good sites for analysis.

Treatments with MMP1, MMP2 and MMP13 were carried out at 25° C. The results show that none of these MMPs cleaved V-CL protein efficiently at 25° C. But after denaturation, MMP2 and MMP13 cleaved V-CL protein efficiently. This observation is consistent with the fact that human fibroblast collagenase cleaves types I, II, and III denatured collagens (gelatins) at G-L(I)-Y-G (SEQ ID NO.: 91-92) loci. (Several loci which are sensitive to collagenases in denatured collagens are protected in the native triple-helical collagen.)

This means that under native condition, V-CL protein can serve as a good background for MMP specificity study.

b) Analysis of V-CL sequence in terms of Field's model

```
                                                 (SEQ ID NO: 7)
CL domain:
 1       11       21       31
GSPGLPGPRG EQGPTGPTGP AGPRGLQGLQ GLQGERGEQG 41       51       61       71
PTGPAGPRGL QGERGEQGPT GLAGKAGEAG AKGETGPAGP 81       91      101      111
QGPRGEQGPQ GLPGKDGEAG AQGPAGPMGP AGERGEKGEP 121      131      141      151
GTQGAKGDRG ETGPVGPRGE RGEAGPAGKD GERGPVGPAG 161      171      181      191
KDGQNGQDGL PGKDGKDGQN GKDGLPGKDG KDGQNGKDGL 201      211      221      231
PGKDGKDGQD GKDGLPGKDG KDGLPGKDGK DGQPGKPGKY
```

All the triplets containing an imino acid (high imino acid-containing region) are shaded. The only region with four consecutive triplets shaded is from G13 to R24, preceding a potential cleavage site G-L-Q. There are also three regions with three consecutive triplets shaded. One region is from G1 to R9, which is at the very beginning of the protein and not a good site for analysis. One region is from G40 to R48, preceding a potential cleavage site G-L-Q. And the last region is from G76 to R84, followed by GEQGPQGLP (SEQ ID NO.: 68). GEQ here may be mutagenized to GPQ, forming a region of five consecutive triplets containing high imino acid and preceding a potential cleavage site G-L-P.

The sequence unshaded is the region of low imino acid. Following the four potential cleavage site, the regions are all low imino acid (<17%)-containing.

V-CL sequence is highly charged with residues R, K, D and E. This is a characteristic of bacterial collagen but may affect MMP behaviors. For the first potential cleavage site, there are two charged residue in the entire 25 residue cleavage site region from G12 to G37. Similarly, there are five charged residues in the second cleavage site, seven in the third site, and five in the fourth site.

A. Design of Mutagenesis and Insertion:

a) Mutagenesis

All the four potential cleavage sites can be mutagenized to a more favorable site in type II collagen: GPQGLA (SEQ ID NO.: 21). But as stated above, the first potential cleavage site is the best one. In order to change GPRGLQ (SEQ ID NO.: 27) to GPQGLA (SEQ ID NO.: 21), 24R to Q and 27Q to A can simply be mutagenized. Previous study on sequence specificity also showed that for some substrates, at least 12 residues from subsites $P_4$-$P_{8'}$ are necessary for cleavage. So a 12-residue sequence from type II collagen GPQGLAGQRGIV (SEQ ID NO: 69) can be introduced into V-CL sequence, either by mutagenesis or by construction (mutagenesis may be a simpler method). If needed, the sequence to either the C-terminus or the N-terminus or both can be extended until it reaches 25 residues, which is considered to be enough for MMP recognition and cleavage. Similar design is also applied for the other three potential cleavage sites. And similar design is also applied for introducing type III collagen cleavage site.

b) Insertion

MMP cleavage site on type II and type III collagen is inserted into V-CL sequence. For each cleavage site, both a short ("a" sequence below, 12 residues) stretch and a long ("b" sequence below, 24 residues) stretch are inserted. MMP cleavage sites are underlined.

(1) MMP cleavage site and flanking sequence on type III collagen:

```
                                                 (SEQ ID NO: 70)
    -GAQGPPGAPGPLGIAGITGARGLAGPPGMPGPRGS-
```

Possible insertion sequence:

```
                                          (SEQ ID NO: 71)
 a. -GPLGIAGITGAR-                        4 triplets
                                          (SEQ ID NO: 72)
 b. -GAQGPPGAPGPLGIAGITGARGLA-            8 triplets
```

(2) MMP cleavage site and flanking sequence on type II collagen:

```
-GPSGAEGPPGPQGLAGQRGIVGLPGQRGERGFP-  (SEQ ID NO: 73)
```

Possible insertion sequence:

```
                                          (SEQ ID NO: 74)
 a. -GPQGLAGQRGIV-                        4 triplets
                                          (SEQ ID NO: 75)
 b. -GPSGAEGPPGPQGLAGQRGIVGLP-            8 triplets
```

At nucleotide level, it's much easier to insert the sequences between two bacterial collagen-like domains. So the insertion will be flanked by -GKDGKDGQPGKP (SEQ ID NO: 76)-Insert-GPRGEQGPTGPT- (SEQ ID NO: 77).

The complete constructs will be V domain-CL domain-Insert-CL domain.

Mutagenesis in the insertion sequence

The sequence of V domain-CL domain-Insert-CL domain itself can serve as a positive control. Different mutations can be introduced into the insertion sequence to obtain single or multiple mutations.

Example 12

Refolding of the Triple Helical Domain In Vitro and In Vivo

A. In Vitro Refolding of the *S. Pyogenes* Scl2 Protein.

Figure 13:
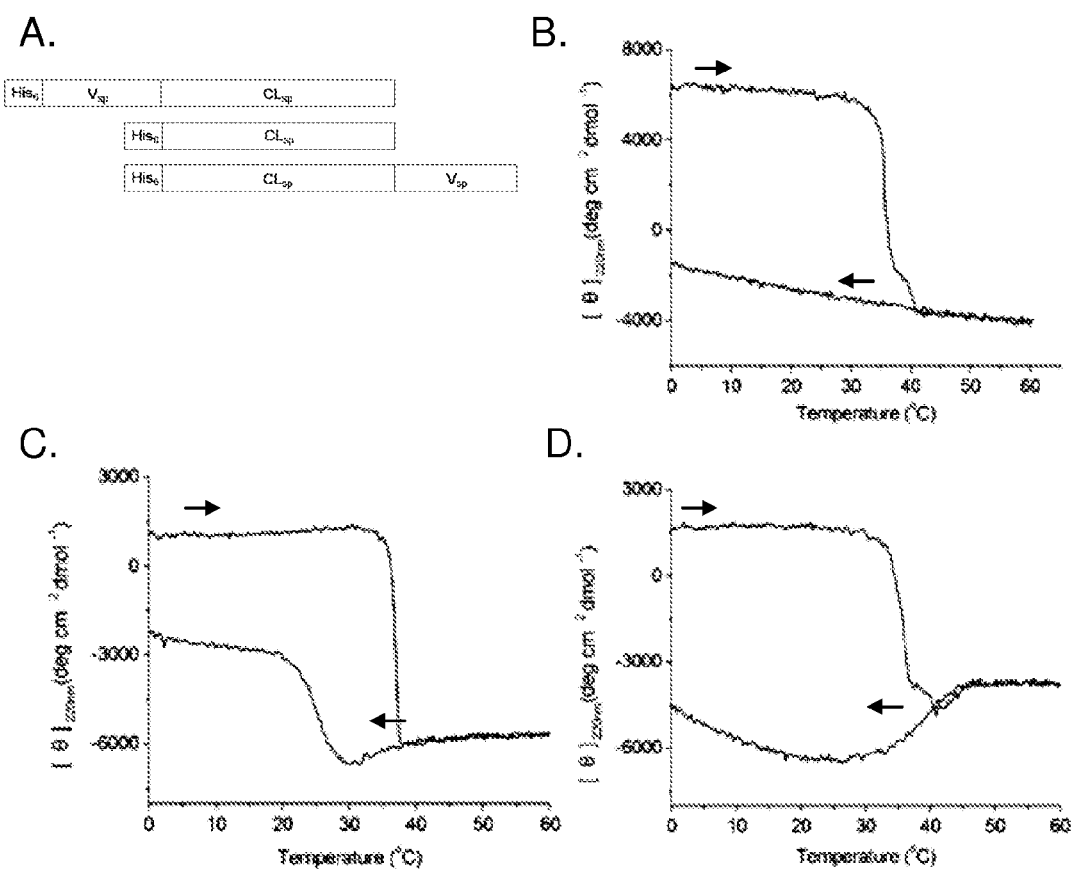
FIG. 13 provides the melting and refolding when the $V_{Sp}$ domain is located N-terminal v.s. C-terminal to the triple-helix domain.

The recombinant collagenous domain of the Scl1 protein was previously shown to fold into a stable triple-helix when expressed in *E. coli* without its N-terminal globular domain. Similar correct triple-helix folding is also observed for the recombinant (Gly-Xaa-Yaa)$_{79}$ CL$_{sp}$ domain from the Scl2 protein expressed as His-tagged CL$_{sp}$ in *E. coli* (FIG. 13A, top construct). The recombinant CL$_{sp}$ domain shows a characteristic collagen CD spectrum and a thermal stability of 36° C. (FIG. 13B, right arrow). The stability of this recombinant triple-helix domain is the same as seen for the triple-helix domain obtained after trypsin digestion of $V_{sp}$-$CL_{sp}$. But after heat denaturation, the collagenous domain of the Scl2 protein shows no ability to refold in vitro on this time scale (FIG. 13B, left arrow), consistent with results reported previously for the Scl1 triple-helix domain.

To investigate whether the position of $V_{sp}$ domain with respect to the triple-helix domain is important for folding in E. coli or refolding in vitro, a construct was designed to make His-tagged $CL_{sp}$-$V_{sp}$ protein, where the globular domain is now C-terminal to the triple-helix (FIG. 13A, bottom construct). Recombinant $CL_{sp}$-$V_{sp}$ forms a soluble triple-helix containing molecule with a CD spectrum (MRE220 ~1470 deg cm2 dmol-1) very similar to that of the original $V_{sp}$-$CL_{sp}$ construct. The thermal denaturation of $CL_{sp}$-$V_{sp}$ protein purified from E. coli is similar to that seen for the $V_{sp}$-$CL_{sp}$ protein and the $CL_{sp}$ domain alone (FIGS. 13B and C, right arrow). However, there is some indication of a second transition for $CL_{sp}$-$V_{sp}$, where the CD signal at 220 nm starts to increase after the temperature reaches ~40° C., which could reflect independent denaturation of the Vsp domain.

In vitro refolding experiments were carried out after heat denaturation on $CL_{sp}$, $V_{sp}$-$CL_{sp}$ and $CL_{sp}$-$V_{sp}$ proteins. No indication of refolding is seen for His-$CL_{sp}$ (FIG. 13B, left arrow), while $V_{sp}$-$CL_{sp}$ protein successfully achieves a substantial amount of refolding (FIG. 13C, left arrow) as reported previously. The inability of $V_{sp}$-$CL_{sp}$ protein to fully refold could be related to aggregation, which removes some of the protein from solution, or to the conditions of refolding. Experiments with other conditions have resulted in much higher percentages of refolding. In contrast to $V_{sp}$-$CL_{sp}$, $CL_{sp}$-$V_{sp}$ does not appear to be capable of significant in vitro refolding (FIG. 13D, left arrow). As the temperature drops below 45° C., the CD signal starts to decrease, suggesting the formation of triple helix and refolding of the $V_{sp}$ domain. When the temperature falls below 25° C., there is a small increase in MRE 220 nm but it never reaches a value expected for formation of a significant amount of triple-helix.

Figure 14:
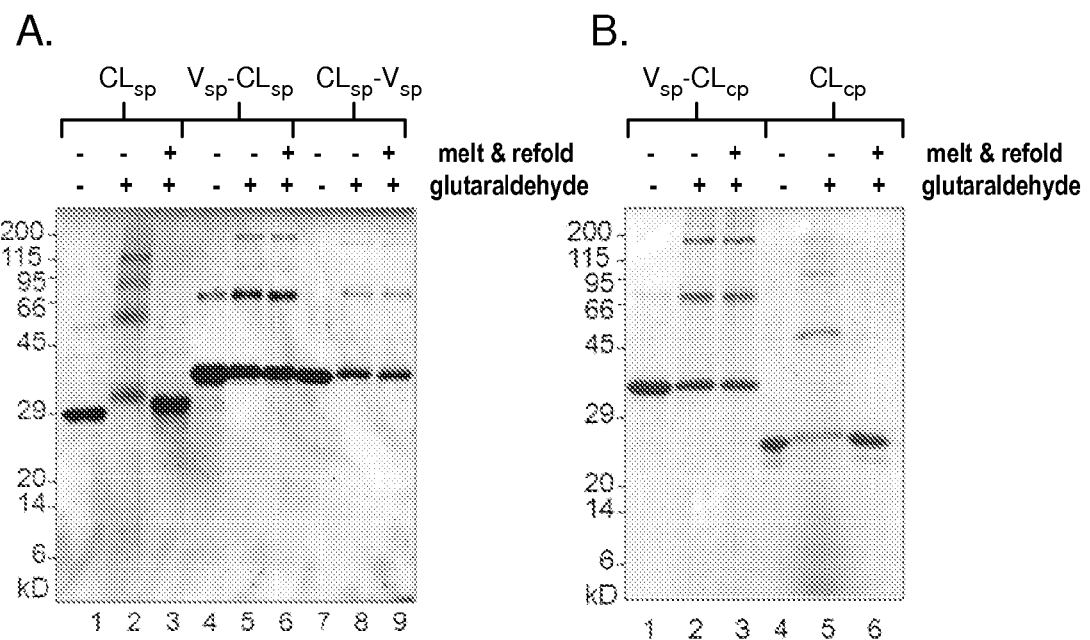
FIG. 14 illustrates the SDS-PAGE results of the cross-linking studies of the bacterial collagen-like proteins and their collagenous domains, to define the trimerization state of the proteins initially and after in vitro refolding.

To investigate the relationship between refolding of these proteins and trimerization, cross-link experiments were carried out to determine whether the $CL_{sp}$, $V_{sp}$-$CL_{sp}$ and $CL_{sp}$-$V_{sp}$ proteins reform trimers after cooling the denatured protein (FIG. 14A). The presence of cross-linked oligomeric species suggests that $V_{sp}$-$CL_{sp}$ and $CL_{sp}$-$V_{sp}$ proteins reform trimers while $CL_{sp}$ does not. The drop in MRE 220 upon refolding and the presence of cross-linked oligomers suggest the $V_{sp}$ domain of the $CL_{sp}$-$V_{sp}$ construct can refold to form trimers but this is not followed by effective folding of the adjacent $CL_{sp}$ domain. These experiments demonstrate that the $V_{sp}$ domain can trimerize on its own, whether it is N-terminal or C-terminal to the triple-helix but it can only promote efficient in vitro refolding when on the N-terminal side of the $CL_{sp}$ domain.

B. V Domain Facilitates the Folding and Refolding of a Heterologous Collagen-Like Protein.

Figure 15:
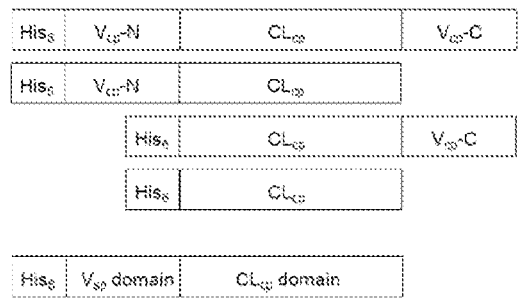
FIG. 15 illustrates that $V_{Sp}$ domain facilitates the folding and refolding of the heterologous $CL_{cp}$ domain.
Figure 15:
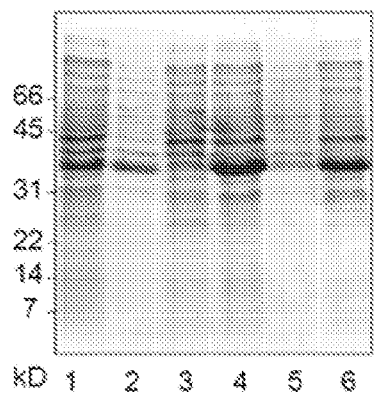
Figure 15:
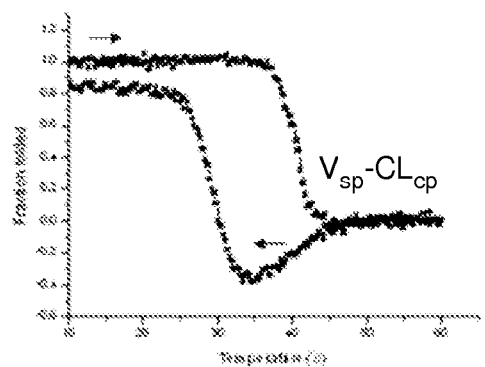
Figure 15:
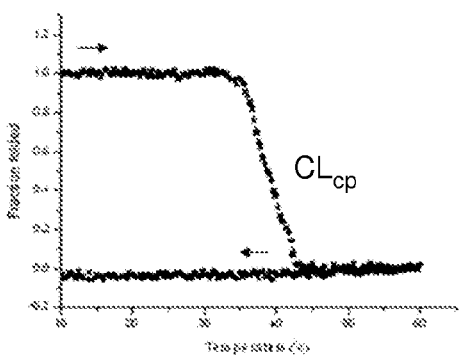

The ability of $V_{sp}$ to promote folding of a heterologous triple-helix, which cannot fold on its own, was examined. The bacterium Clostridium perfringens was found to contain a gene encoding a collagen-like protein, composed of a 53 residue N-terminal non-collagenous domain ($N_{cp}$), a collagen-like domain (Gly-Xaa-Yaa)63 (denoted as $CL_{cp}$) and a 161 residue C-terminal non-collagenous domain ($C_{cp}$) (FIG. 15A). Four constructs $N_{cp}$-$CL_{cp}$-$C_{cp}$, $N_{cp}$-$CL_{cp}$, $CL_{cp}$-$C_{cp}$ and $CL_{cp}$ (FIG. 15A) were previously expressed in E. coli using the cold shock vector system described above and all were found in inclusion bodies, suggesting an inability to correctly fold to form stable triple-helices. In an attempt to promote proper folding, the $V_{sp}$ domain from S. pyogenes was fused N-terminal to the $CL_{cp}$ domain, creating the chimeric protein $V_{sp}$-$CL_{cp}$ (FIG. 5A). The $V_{sp}$-$CL_{cp}$ protein was fully soluble (FIG. 15B), suggesting that the $V_{sp}$ domain facilitates the correct folding of this heterologous collagen-like domain as expressed in E. coli.

To further determine whether $V_{sp}$-$CL_{cp}$ forms a proper triple helix, the physicochemical properties of $V_{sp}$-$CL_{cp}$ and the $CL_{cp}$ domain, obtained by trypsin treatment of $V_{sp}$-$CL_{cp}$, were determined. The CD spectra of both $V_{sp}$-$CL_{cp}$ and the $CL_{cp}$ domain show characteristic features of the collagen triple-helix (data not shown). The magnitude of the CD peak at 220 nm is lower for $V_{sp}$-$CL_{cp}$ than for the $CL_{cp}$ domain, as expected when the $V_{sp}$ domain contributes a negative triple helical peak around 222 nm that partly cancels out the positive 220 nm peak of the collagen triple-helix signal. The thermal transitions of both $V_{sp}$-$CL_{cp}$ and $CL_{cp}$ domains are not as sharp as seen for $V_{sp}$-$CL_{sp}$ and $CL_{sp}$ domains, and showed some sign of multiple transitions (FIGS. 15C and D, right arrow). The melting temperatures were Tm=40.6° C. for $V_{sp}$-$CL_{cp}$ and Tm=38.8° C. for $CL_{cp}$, suggesting that the presence of the $V_{sp}$ domain provides a small degree of stabilization. The in vitro refolding of both proteins was also studied (FIGS. 15C and D, left arrow). For $V_{sp}$-$CL_{cp}$, cooling results in an initial drop in the MRE 220 nm CD signal, consistent with the formation of triple helical structure, followed by an increase in MRE 220 nm and the recovery of about 80% of the initial CD signal. This suggests refolding of the N-terminal $V_{sp}$ domain must occur before refolding of the triple-helix structure takes place. Cross-link experimental evidence indicates that $V_{sp}$-$CL_{cp}$ trimers are reformed (FIG. 14B). In contrast, after the isolated $CL_{cp}$ domain alone is heat denatured and then cooled down, no CD signal is recovered and no cross-linked trimers are formed (FIG. 14B and FIG. 15C), implying that $V_{sp}$ domain is required for efficient and proper refolding of the heterologous collagen-like $CL_{cp}$ domain.

Example 13

Cytotoxicity and Immungenocity

A. Preparation of Stabilized $CL_Q$ Protein Samples

For sponge preparation, purified CL protein was prepared in 20 mM acetic acid and freeze dried. Dry collagen was held at 20° C. over vapour from 20% w/v glutaraldehyde (GA) for 18 h in a closed vessel. Stabilised samples were then held covered in air and stored at room temperature until analysis. Prior to cell evaluations samples were washed with 3 changes of sterile PBS.

B. Thermal Stability of Stabilised $CL_{Sp}$ Protein Samples

The thermal stability of the GA stabilised samples was examined by differential scanning calorimetry (DSC) on a Mettler Toledo DSC 821e instrument using samples in PBS.

C. Cytotoxicity Evaluation of Soluble CL Protein

Cytotoxicity was assessed using human lung fibroblast WI-38 and human fibrosarcoma HT1080 cells in a Neutral Red assay. Bovine skin collagen (BSC), prepared by differential salt precipitation of a pepsin extract was used as a control. Samples containing CL protein or BSC (1, 10 and 50 mg/ml) were prepared using serum-free DMEM (for WI-38) or MEM (for HT1080) and sterilised using a 0.2 mm filter. WI-38 cells and HT1080 cells were seeded onto a 96-well plate at $1.5 \times 10^4$ cells/well in MEM or DMEM, respectively, with 10% foetal calf serum (FCS) and 1% penicillin/streptomycin. After 24 h, medium was replaced with 150 ml of the sample or medium control and incubated for an additional 24 h. Viability of the cells was then determined using a Neutral red assay at 37° C. in PBS.

Figure 16:
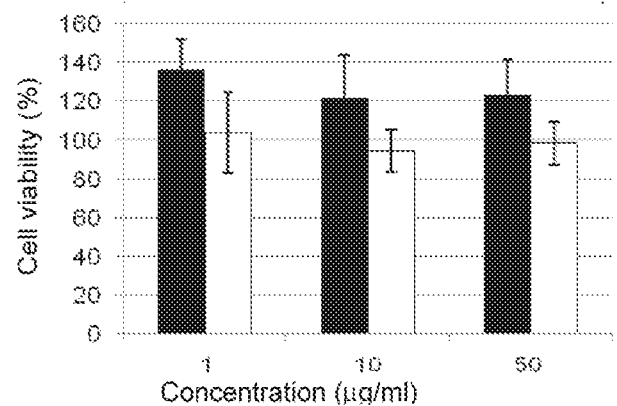
FIG. 16 illustrates cytotoxicity evaluation using a Neutral Red assay, showing cell viability after 24 h incubations with HT1080 and WI-38 cells.
Figure 16:
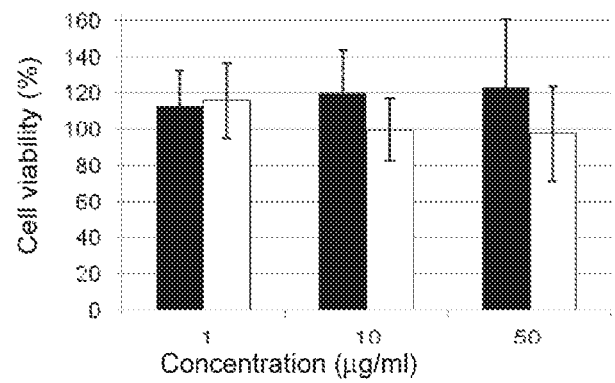

No significant changes were observed in the cell viability nor cell morphology after 24 h for WI-38 cells and HT1080 cells when compared to cells incubated in serum-free DMEM and MEM, which were taken as the 100% reference level (FIG. 16). The bovine skin collagen (BSC) controls showed 20-30% enhanced viability at 24 h compared to the medium only controls which is probably due to the better cell attachment by BSC in the serum free media. Thus, these results indicate that the collagen like CL domain is not cytotoxic when assessed using HT1080, WI-38 or L929 cells.

We claim:

1. A recombinant bacterial collagen-like protein structure comprising a formula:

[(Gly-Xaa-Yaa)$_m$-(insert)$_n$]$_p$ wherein m is between 1 to 200, n is 1, and p is between 2 to 10, wherein (Gly-Xaa-Yaa)$_m$ represents a tandem repeat triple helical domain wherein Xaa and Yaa are independently any natural or unnatural imino or amino acid with the proviso that neither Xaa nor Yaa is a hydroxyproline, wherein the insert is comprised of 1 to 50 of any imino or amino acids and wherein the insert is a non-triple helical forming peptide sequence, wherein the tandem repeat triple helical domains have a circular dichroism spectroscopy value of between 0.04 to 0.13 for the ratio of positive peak (about 220 nm) to negative peaks (about 198 nm), and wherein the collagen-like protein structure is stable at temperatures between 35° C. and 40° C.

2. The collagen-like protein structure of claim 1, wherein the tandem repeat triple helical domains have a proline content of greater than 19% of all residues in the Xaa and Yaa positions.

3. The collagen-like protein structure of claim 2, wherein the tandem repeat triple helical domains have a proline content of between 19.5% and 40% of all residues in the Xaa and Yaa positions.

4. The collagen-like protein structure of claim 1, wherein the tandem repeat triple helical domains have a concentration of charged amino acids of greater than 14% of all residues in the Xaa and Yaa positions.

5. The collagen-like protein structure of claim 1, wherein the tandem repeat triple helical domains have a concentration of charged amino acids of between 14-35% of all residues in the Xaa and Yaa positions.

6. The collagen-like protein structure of claim 1, further comprising a non-collagenous domain bound at either an amino terminus end or a carboxy terminus end of the collagen-like protein, which facilitates protein folding of the tandem repeat triple helical domains.

7. The collagen-like protein structure of claim 6, wherein the non-collagenous domain is SEQ ID NO: 47.

8. The collagen-like protein structure of claim 6, wherein the non-collagenous domain is SEQ ID NO: 47 and is bound to the protein at the amino terminus end of the collagen-like protein.

9. The recombinantly expressed protein of claim 6, wherein the non-collagenous domain is SEQ ID NO: 51 and is bound to the protein at the carboxy terminus end of the triple helical domain.

10. The recombinantly expressed protein of claim 6, wherein the non-collagenous domain is selected from the group consisting of a foldon, a coiled coil sequence, and a C-propeptide.

11. The recombinantly expressed protein of claim 1, wherein the insert sequence includes at least one non-collagen natural break having a peptide sequence spaced between two glycine residues.

12. The recombinantly expressed protein of claim 11, wherein the non-collagen natural break is selected from the group consisting of SEQ ID NOs: 12-14, SEQ ID NO: 16, SEQ ID NO: 17, SEQ ID NO: 50, SEQ ID NO: 65, and combinations thereof.

13. The collagen-like protein structure of claim 1, wherein the tandem repeat triple-helical domains aggregate at neutral pH.

14. A recombinant bacterial collagen-like protein structure comprising a formula:

[(Gly-Xaa-Yaa)$_m$-(insert)$_n$]$_p$ and at least one non-collagenous domain bound to the protein structure to at least one of an amino terminus end or a carboxy terminus end of the protein structure, wherein m is between 1 to 200, n is 1, and p is between 2 to 10, wherein (Gly-Xaa-Yaa)$_m$ represents a tandem repeat triple helical domain wherein Xaa and Yaa are independently any natural or unnatural imino or amino acid with the proviso that neither Xaa nor Yaa is a hydroxyproline, wherein the insert is comprised of 1 to 50 of any imino or amino acids and wherein the insert is a non-triple helical forming peptide sequence wherein the tandem repeat triple helical domains have a circular dichroism spectroscopy value of between 0.04 to 0.13 for the ratio of positive peak (about 220 nm) to negative peaks (about 198 nm), and wherein the non-collagenous domain facilitates protein folding of the tandem repeat triple helical domains, and wherein the collagen-like protein structure is stable at temperatures between 35° C. and 40° C.

15. The collagen-like protein structure of claim 14, wherein the tandem repeat triple helical domains have a Proline content of greater than 19% of all residues in the Xaa and Yaa positions.

16. The collagen-like protein structure of claim 15, wherein the tandem repeat triple helical domains have a Proline content of between 19.5% and 40% of all residues in the Xaa and Yaa positions.

17. The collagen-like protein structure of claim 14, wherein the tandem repeat triple helical domains have a concentration of charged amino acids of greater than 14% of all residues in the Xaa and Yaa positions.

18. The collagen-like protein structure of claim 14, wherein the tandem repeat triple helical domains have a concentration of charged amino acids of between 14-35% of all residues in the Xaa and Yaa positions.

19. The collagen-like protein structure of claim 18, wherein the tandem repeat triple helical domains are stable at temperatures between 35° C. and 40° C. in its native form.

20. The collagen-like protein structure of claim 14, wherein the non-collagenous domain is SEQ ID NO: 47.1.

21. The collagen-like protein structure of claim 14, wherein the non-collagenous domain is SEQ ID NO: 47 and is bound to the protein at the amino terminus end of the collagen-like protein.

22. The recombinantly expressed protein of claim 14, wherein the non-collagenous domain is SEQ ID NO: 51 and is bound to the protein at the carboxy terminus end of the triple helical domain.

23. The recombinantly expressed protein of claim 14, wherein the non-collagenous domain is selected from the group consisting of a foldon, a coiled coil sequence, and a C-propeptide.

24. The recombinantly expressed protein of claim 14, wherein the insert sequence includes at least one non-collagen natural break having a peptide sequence spaced between two glycine residues.

25. The recombinantly expressed protein of claim 24, wherein the non-collagen natural break is selected from the group consisting of SEQ ID NOs: 12-14, SEQ ID NO: 16, SEQ ID NO: 17, SEQ ID NO: 50, SEQ ID NO: 65, and combinations thereof.

26. The collagen-like protein structure of claim 14, wherein the triple-helical domain aggregates at neutral pH.

27. A method of producing a recombinant collagen-like protein comprising:
(a) inserting nucleic acid sequences encoding a bacterial collagen-like protein into a single nucleic acid vector, said recombinant bacterial collagen-like protein structure comprising a formula:

$$[(Gly\text{-}Xaa\text{-}Yaa)_m\text{-}(insert)_n]_p$$

wherein m is between 1 to 200 n is 1 and is between 2 to 10, wherein $(Gly\text{-}Xaa\text{-}Yaa)_m$ represents a tandem repeat triple helical domain wherein Xaa and Yaa are independently any natural or unnatural imino or amino acid with the proviso that neither Xaa nor Yaa is a hydroxyproline, wherein the insert is comprised of 1 to 50 of any imino or amino acids and wherein the insert is a non-triple helical forming peptide sequence;
(b) optionally inserting into said vector a nucleic acid encoding a non-collagenous domain nucleic acid sequence at either or both 5' or 3' end of the nucleic acid encoding the bacterial collagen-like protein, which facilitates protein folding of the triple helical domain upon expression;
(c) optionally inserting a sequence tag;
(d) expressing the vector within a micro-organism; and
(e) isolating the bacterial collagen-like protein.

28. The method of claim 27 wherein the nucleic acid vector is a cold-shock vector.

29. The method of claim 27 wherein the nucleic acid sequence is expressed within the micro-organism at temperatures below 37° C.

30. The method of claim 27 wherein the nucleic acid sequence is expressed within the micro-organism at a temperature of about 15° C.

* * * * *

SEQUENCE LISTING

```
<160> NUMBER OF SEQ ID NOS: 92

<210> SEQ ID NO 1
<211> LENGTH: 7
<212> TYPE: PRT
<213> ORGANISM: Artificial Sequence
<220> FEATURE:
<223> OTHER INFORMATION: Thrombin/Trypsin cleavage sequence

<400> SEQUENCE: 1

Leu Val Pro Arg Gly Ser Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Enterokinase cleavage sequence

<400> SEQUENCE: 2

Asp Asp Asp Asp Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Factor Xa protease cleavage sequence

<400> SEQUENCE: 3

Ile Glu Gly Arg
1

<210> SEQ ID NO 4
<211> LENGTH: 4
<212> TYPE: PRT
<213> ORGANISM: Artificial Sequence
<220> FEATURE:
<223> OTHER INFORMATION: Factor Xa protease cleavage sequence

<400> SEQUENCE: 4

Ile Asp Gly Arg
1

<210> SEQ ID NO 5
<211> LENGTH: 6
<212> TYPE: PRT
<213> ORGANISM: Artificial Sequence
<220> FEATURE:
<223> OTHER INFORMATION: Tomato protease etch virus cleavage sequence

<400> SEQUENCE: 5

Glu Asn Leu Phe Gln Gly
1               5

<210> SEQ ID NO 6
```

```
<211> LENGTH: 8
<212> TYPE: PRT
<213> ORGANISM: Artificial Sequence
<220> FEATURE:
<223> OTHER INFORMATION: PreScission protease cleavage sequence

<400> SEQUENCE: 6

Leu Glu Val Leu Phe Gln Gly Pro
1               5

<210> SEQ ID NO 7
<211> LENGTH: 240
<212> TYPE: PRT
<213> ORGANISM: Streptococcus pyogenes

<400> SEQUENCE: 7

Gly Ser Pro Gly Leu Pro Gly Pro Arg Gly Glu Gln Gly Pro Thr Gly
1               5                   10                  15

Pro Thr Gly Pro Ala Gly Pro Arg Gly Leu Gln Gly Leu Gln Gly Leu
            20                  25                  30

Gln Gly Glu Arg Gly Glu Gln Gly Pro Thr Gly Pro Ala Gly Pro Arg
        35                  40                  45

Gly Leu Gln Gly Glu Arg Gly Glu Gln Gly Pro Thr Gly Leu Ala Gly
    50                  55                  60

Lys Ala Gly Glu Ala Gly Ala Lys Gly Glu Thr Gly Pro Ala Gly Pro
65                  70                  75                  80

Gln Gly Pro Arg Gly Glu Gln Gly Pro Gln Gly Leu Pro Gly Lys Asp
                85                  90                  95

Gly Glu Ala Gly Ala Gln Gly Pro Ala Gly Pro Met Gly Pro Ala Gly
            100                 105                 110

Glu Arg Gly Glu Lys Gly Glu Pro Gly Thr Gln Gly Ala Lys Gly Asp
        115                 120                 125

Arg Gly Glu Thr Gly Pro Val Gly Pro Arg Gly Glu Arg Gly Glu Ala
    130                 135                 140

Gly Pro Ala Gly Lys Asp Gly Glu Arg Gly Pro Val Gly Pro Ala Gly
145                 150                 155                 160

Lys Asp Gly Gln Asn Gly Gln Asp Gly Leu Pro Gly Lys Asp Gly Lys
                165                 170                 175

Asp Gly Gln Asn Gly Lys Asp Gly Leu Pro Gly Lys Asp Gly Lys Asp
            180                 185                 190

Gly Gln Asn Gly Lys Asp Gly Leu Pro Gly Lys Asp Gly Lys Asp Gly
        195                 200                 205

Gln Asp Gly Lys Asp Gly Leu Pro Gly Lys Asp Gly Lys Asp Gly Leu
    210                 215                 220

Pro Gly Lys Asp Gly Lys Asp Gly Gln Pro Gly Lys Pro Gly Lys Tyr
225                 230                 235                 240

<210> SEQ ID NO 8
<211> LENGTH: 189
<212> TYPE: PRT
<213> ORGANISM: Clostridium perfringens

<400> SEQUENCE: 8

Gly Pro Arg Gly Pro Arg Gly Pro Gln Gly Glu Gln Gly Pro Gln Gly
1               5                   10                  15

Glu Arg Gly Phe Thr Gly Pro Gln Gly Pro Val Gly Pro Gln Gly Glu
            20                  25                  30

Gln Gly Pro Gln Gly Glu Arg Gly Phe Thr Gly Pro Gln Gly Pro Ile
```

```
                35                  40                  45
Gly Leu Gln Gly Glu Gln Gly Pro Gln Gly Glu Arg Gly Phe Thr Gly
     50                  55                  60

Pro Gln Gly Pro Val Gly Pro Gln Gly Glu Gln Gly Pro Gln Gly Glu
 65                  70                  75                  80

Arg Gly Phe Thr Gly Pro Gln Gly Pro Val Gly Pro Gln Gly Glu Gln
                 85                  90                  95

Gly Pro Gln Gly Glu Arg Gly Phe Thr Gly Pro Gln Gly Pro Ile Gly
            100                 105                 110

Pro Gln Gly Glu Gln Gly Pro Gln Gly Glu Arg Gly Phe Thr Gly Pro
        115                 120                 125

Gln Gly Pro Ile Gly Pro Gln Gly Asn Gln Gly Pro Ile Gly Pro Gln
    130                 135                 140

Gly Glu Gln Gly Pro Gln Gly Ala Thr Gly Pro Gln Gly Pro Gln Gly
145                 150                 155                 160

Pro Val Gly Pro Gln Gly Asn Gln Gly Pro Ile Gly Pro Gln Gly Pro
                165                 170                 175

Val Gly Pro Gln Gly Pro Gln Gly Gln Pro Gly Val Asn
            180                 185

<210> SEQ ID NO 9
<211> LENGTH: 129
<212> TYPE: PRT
<213> ORGANISM: Methylobacterium sp. 4-46

<400> SEQUENCE: 9

Gly Leu Pro Gly Pro Lys Gly Asp Pro Gly Pro Gln Gly Pro Ala Gly
 1               5                  10                  15

Pro Lys Gly Glu Pro Gly Pro Lys Gly Glu Pro Gly Pro Lys Gly Glu
             20                  25                  30

Pro Gly Pro Lys Gly Glu Pro Gly Pro Lys Gly Glu Pro Gly Pro Lys
         35                  40                  45

Gly Glu Pro Gly Pro Lys Gly Glu Pro Gly Pro Lys Gly Glu Pro Gly
     50                  55                  60

Pro Arg Gly Glu Ala Gly Pro Gln Gly Ala Leu Gly Pro Lys Gly Glu
 65                  70                  75                  80

Ala Gly Ser Arg Gly Glu Pro Gly Pro Arg Gly Glu Pro Gly Pro Lys
                 85                  90                  95

Gly Glu Ala Gly Leu Ala Gly Ala Pro Gly Pro Lys Gly Glu Ala Gly
            100                 105                 110

Pro Arg Gly Pro Gln Gly Glu Arg Gly Pro Pro Gly Ala Pro Gly Ala
        115                 120                 125

Ala

<210> SEQ ID NO 10
<211> LENGTH: 246
<212> TYPE: PRT
<213> ORGANISM: Solibacter Usitatus Ellin6076

<400> SEQUENCE: 10

Gly Pro Ala Gly Pro Ala Gly Pro Gln Gly Pro Ala Gly Pro Ala Gly
 1               5                  10                  15

Ala Gln Gly Pro Ala Gly Pro Ala Gly Pro Gln Gly Pro Ala Gly Pro
             20                  25                  30

Gln Gly Ser Ala Gly Ala Gln Gly Pro Lys Gly Asp Thr Gly Ala Ala
         35                  40                  45
```

```
Gly Pro Ala Gly Glu Ala Gly Pro Lys Gly Glu Thr Gly Ala Ala Gly
         50                  55                  60

Pro Lys Gly Asp Thr Gly Ala Ala Gly Pro Ala Gly Pro Lys Gly Asp
 65                  70                  75                  80

Thr Gly Ala Ala Gly Pro Ala Gly Pro Lys Gly Asp Thr Gly Ala Ala
                 85                  90                  95

Gly Ala Thr Gly Pro Lys Gly Glu Lys Gly Glu Thr Gly Ala Ala Gly
                100                 105                 110

Pro Lys Gly Asp Lys Gly Glu Thr Gly Ala Ala Gly Pro Lys Gly Asp
                115                 120                 125

Lys Gly Glu Thr Gly Ala Ala Gly Pro Lys Gly Glu Lys Gly Glu Thr
        130                 135                 140

Gly Ala Val Gly Pro Lys Gly Asp Lys Gly Glu Thr Gly Ala Ala Gly
145                 150                 155                 160

Pro Lys Gly Asp Arg Gly Glu Thr Gly Ala Val Gly Pro Lys Gly Asp
                165                 170                 175

Lys Gly Glu Thr Gly Ala Val Gly Pro Lys Gly Asp Lys Gly Glu Thr
                180                 185                 190

Gly Ala Ile Gly Pro Lys Gly Asp Lys Gly Asp Lys Gly Asp Lys Gly
                195                 200                 205

Asp Ala Gly Val Ala Gly Pro Gln Gly Ile Gln Gly Val Lys Gly Asp
        210                 215                 220

Thr Gly Leu Gln Gly Pro Lys Gly Asp Ala Gly Pro Gln Gly Ala Pro
225                 230                 235                 240

Gly Thr Pro Gly Gly Gly
                245

<210> SEQ ID NO 11
<211> LENGTH: 117
<212> TYPE: PRT
<213> ORGANISM: Rhodopseudomonas palustris tie-1

<400> SEQUENCE: 11

Gly Arg Pro Gly Pro Gln Gly Pro Arg Gly Arg Pro Gly Glu Pro Gly
 1               5                  10                  15

Arg Pro Gly Pro Gln Gly His Pro Gly Arg Pro Gly Pro Glu Gly Pro
                20                  25                  30

Arg Gly Lys Gln Gly Pro Val Gly Lys Pro Gly Pro Gln Gly Lys Ala
                35                  40                  45

Gly Pro Gln Gly Lys Pro Gly Ile Ala Gly Lys Pro Gly Pro Asp Gly
         50                  55                  60

Lys Pro Gly Pro Ile Gly Pro Gln Gly Lys Ala Gly Pro Gln Gly Pro
 65                  70                  75                  80

Arg Gly Glu Gln Gly Leu Arg Gly Glu Gln Gly Pro Arg Gly Glu Gln
                85                  90                  95

Gly Pro Gln Gly Pro Arg Gly Glu Gln Gly Pro Arg Gly Glu Pro Gly
                100                 105                 110

Pro Ala Gly Ala Leu
        115

<210> SEQ ID NO 12
<211> LENGTH: 6
<212> TYPE: PRT
<213> ORGANISM: Artificial Sequence
<220> FEATURE:
<223> OTHER INFORMATION: Non collagen natural break
```

```
<400> SEQUENCE: 12

Gly Ala Ala Val Met Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Non collagen natural break

<400> SEQUENCE: 13

Gly Asp Ser Ala Val Ile Leu Gly
1               5

<210> SEQ ID NO 14
<211> LENGTH: 10
<212> TYPE: PRT
<213> ORGANISM: Artificial Sequence
<220> FEATURE:
<223> OTHER INFORMATION: Non collagen natural break

<400> SEQUENCE: 14

Gly Asp Met Val Val Ser Arg Val Lys Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: alpha3 beta1 integrin binding site

<400> SEQUENCE: 15

Gly Glu Phe Tyr Phe Asp Leu Arg Leu Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Non collagen natural break

<400> SEQUENCE: 16

Gly Arg Leu Val Asp Thr Gly Pro Gly Ala Arg Glu Lys Gly
1               5                   10

<210> SEQ ID NO 17
<211> LENGTH: 43
<212> TYPE: PRT
<213> ORGANISM: Artificial Sequence
<220> FEATURE:
<223> OTHER INFORMATION: Non collagen natural break

<400> SEQUENCE: 17

Gly Ser Val Pro Asn Val Asp Arg Leu Leu Glu Thr Ala Gly Ile Lys
1               5                   10                  15

Ala Ser Ala Leu Arg Glu Ile Val Glu Thr Trp Asp Glu Ser Ser Gly
            20                  25                  30

Ser Phe Leu Pro Val Pro Glu Arg Arg Gly
        35                  40

<210> SEQ ID NO 18
```

```
<211> LENGTH: 6
<212> TYPE: PRT
<213> ORGANISM: Artificial Sequence
<220> FEATURE:
<223> OTHER INFORMATION: alpha2 beta1 integrin binding site

<400> SEQUENCE: 18

Gly Phe Pro Gly Glu Arg
1               5

<210> SEQ ID NO 19
<211> LENGTH: 6
<212> TYPE: PRT
<213> ORGANISM: Artificial Sequence
<220> FEATURE:
<223> OTHER INFORMATION: MMP cleavage site

<400> SEQUENCE: 19

Gly Pro Gln Gly Ile Ala
1               5

<210> SEQ ID NO 20
<211> LENGTH: 6
<212> TYPE: PRT
<213> ORGANISM: Artificial Sequence
<220> FEATURE:
<223> OTHER INFORMATION: MMP cleavage site

<400> SEQUENCE: 20

Gly Pro Gln Gly Ile Leu
1               5

<210> SEQ ID NO 21
<211> LENGTH: 6
<212> TYPE: PRT
<213> ORGANISM: Artificial Sequence
<220> FEATURE:
<223> OTHER INFORMATION: MMP cleavage site

<400> SEQUENCE: 21

Gly Pro Gln Gly Leu Ala
1               5

<210> SEQ ID NO 22
<211> LENGTH: 6
<212> TYPE: PRT
<213> ORGANISM: Artificial Sequence
<220> FEATURE:
<223> OTHER INFORMATION: MMP cleavage site

<400> SEQUENCE: 22

Gly Pro Gln Gly Leu Leu
1               5

<210> SEQ ID NO 23
<211> LENGTH: 6
<212> TYPE: PRT
<213> ORGANISM: Artificial Sequence
<220> FEATURE:
<223> OTHER INFORMATION: MMP cleavage site

<400> SEQUENCE: 23

Gly Pro Leu Gly Ile Ala
1               5

<210> SEQ ID NO 24
<211> LENGTH: 6
```

```
<212> TYPE: PRT
<213> ORGANISM: Artificial Sequence
<220> FEATURE:
<223> OTHER INFORMATION: MMP cleavage site

<400> SEQUENCE: 24

Gly Pro Leu Gly Ile Leu
1               5

<210> SEQ ID NO 25
<211> LENGTH: 6
<212> TYPE: PRT
<213> ORGANISM: Artificial Sequence
<220> FEATURE:
<223> OTHER INFORMATION: MMP cleavage site

<400> SEQUENCE: 25

Gly Pro Leu Gly Leu Ala
1               5

<210> SEQ ID NO 26
<211> LENGTH: 6
<212> TYPE: PRT
<213> ORGANISM: Artificial Sequence
<220> FEATURE:
<223> OTHER INFORMATION: MMP cleavage site

<400> SEQUENCE: 26

Gly Pro Leu Gly Leu Leu
1               5

<210> SEQ ID NO 27
<211> LENGTH: 6
<212> TYPE: PRT
<213> ORGANISM: Artificial Sequence
<220> FEATURE:
<223> OTHER INFORMATION: MMP cleavage site

<400> SEQUENCE: 27

Gly Pro Arg Gly Leu Gln
1               5

<210> SEQ ID NO 28
<211> LENGTH: 6
<212> TYPE: PRT
<213> ORGANISM: Artificial Sequence
<220> FEATURE:
<223> OTHER INFORMATION: MMP cleavage site

<400> SEQUENCE: 28

Gly Pro Thr Gly Leu Ala
1               5

<210> SEQ ID NO 29
<211> LENGTH: 327
<212> TYPE: PRT
<213> ORGANISM: Artificial Sequence
<220> FEATURE:
<223> OTHER INFORMATION: Chimeric collagen like proteins

<400> SEQUENCE: 29

Met Asn His Lys Val His Met His His His His His Asp Glu Gln
1               5                   10                  15

Glu Glu Lys Ala Lys Val Arg Thr Glu Leu Ile Gln Glu Leu Ala Gln
            20                  25                  30

Gly Leu Gly Gly Phe Glu Lys Lys Asn Phe Pro Thr Leu Gly Asp Glu
```

```
                  35                  40                  45
Asp Leu Asp His Thr Tyr Met Thr Lys Leu Leu Thr Tyr Leu Gln Glu
 50                  55                  60

Arg Glu Gln Ala Glu Asn Ser Trp Arg Lys Arg Leu Leu Lys Gly Ile
 65                  70                  75                  80

Gln Asp His Ala Leu Asp Leu Val Pro Arg Gly Ser Pro Gly Pro Arg
                 85                  90                  95

Gly Glu Gln Gly Pro Thr Gly Pro Thr Gly Pro Ala Gly Pro Arg Gly
                100                 105                 110

Leu Gln Gly Leu Gln Gly Leu Gln Gly Glu Arg Gly Glu Gln Gly Pro
                115                 120                 125

Thr Gly Pro Ala Gly Pro Arg Gly Leu Gln Gly Glu Arg Gly Glu Gln
                130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Lys Asp Gly Glu Ala Gly Ala Gln Gly Pro Ala
                180                 185                 190

Gly Pro Met Gly Pro Ala Gly Glu Arg Gly Lys Gly Glu Pro Gly
                195                 200                 205

Thr Gln Gly Ala Lys Gly Asp Arg Gly Glu Thr Gly Pro Val Gly Pro
210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
                245                 250                 255

Leu Pro Gly Lys Asp Gly Lys Asp Gly Gln Asn Gly Lys Asp Gly Leu
                260                 265                 270

Pro Gly Lys Asp Gly Lys Asp Gly Gln Asn Gly Lys Asp Gly Leu Pro
                275                 280                 285

Gly Lys Asp Gly Lys Asp Gly Gln Asp Gly Lys Asp Gly Leu Pro Gly
                290                 295                 300

Lys Asp Gly Lys Asp Gly Leu Pro Gly Lys Asp Gly Lys Asp Gly Gln
305                 310                 315                 320

Pro Gly Lys Pro Gly Lys Tyr
                325

<210> SEQ ID NO 30
<211> LENGTH: 564
<212> TYPE: PRT
<213> ORGANISM: Artificial Sequence
<220> FEATURE:
<223> OTHER INFORMATION: Chimeric collagen like proteins

<400> SEQUENCE: 30

Met Asn His Lys Val His Met His His His His Asp Glu Gln
 1                5                  10                  15

Glu Glu Lys Ala Lys Val Arg Thr Glu Leu Ile Gln Glu Leu Ala Gln
                 20                  25                  30

Gly Leu Gly Gly Phe Glu Lys Lys Asn Phe Pro Thr Leu Gly Asp Glu
                 35                  40                  45

Asp Leu Asp His Thr Tyr Met Thr Lys Leu Leu Thr Tyr Leu Gln Glu
 50                  55                  60

Arg Glu Gln Ala Glu Asn Ser Trp Arg Lys Arg Leu Leu Lys Gly Ile
```

-continued

```
                65                  70                  75                  80
        Gln Asp His Ala Leu Asp Leu Val Pro Arg Gly Ser Pro Gly Pro Arg
                        85                  90                  95

Gly Glu Gln Gly Pro Thr Gly Pro Thr Gly Pro Ala Gly Pro Arg Gly
                        100                 105                 110

Leu Gln Gly Leu Gln Gly Leu Gln Gly Glu Arg Gly Glu Gln Gly Pro
                        115                 120                 125

Thr Gly Pro Ala Gly Pro Arg Gly Leu Gln Gly Glu Arg Gly Glu Gln
                        130                 135                 140

Gly Pro Thr Gly Leu Ala Gly Lys Ala Gly Glu Ala Gly Ala Lys Gly
        145                 150                 155                 160

Glu Thr Gly Pro Ala Gly Pro Gln Gly Pro Arg Gly Glu Gln Gly Pro
                        165                 170                 175

Gln Gly Leu Pro Gly Lys Asp Gly Glu Ala Gly Ala Gln Gly Pro Ala
                        180                 185                 190

Gly Pro Met Gly Pro Ala Gly Glu Arg Gly Glu Lys Gly Glu Pro Gly
                        195                 200                 205

Thr Gln Gly Ala Lys Gly Asp Arg Gly Glu Thr Gly Pro Val Gly Pro
                        210                 215                 220

Arg Gly Glu Arg Gly Glu Ala Gly Pro Ala Gly Lys Asp Gly Glu Arg
        225                 230                 235                 240

Gly Pro Val Gly Pro Ala Gly Lys Asp Gly Gln Asn Gly Gln Asp Gly
                        245                 250                 255

Leu Pro Gly Lys Asp Gly Lys Asp Gly Gln Asn Gly Lys Asp Gly Leu
                        260                 265                 270

Pro Gly Lys Asp Gly Lys Asp Gly Gln Asn Gly Lys Asp Gly Leu Pro
                        275                 280                 285

Gly Lys Asp Gly Lys Asp Gly Gln Asp Gly Lys Asp Gly Leu Pro Gly
                        290                 295                 300

Lys Asp Gly Lys Asp Gly Leu Pro Gly Lys Asp Gly Lys Asp Gly Gln
        305                 310                 315                 320

Pro Gly Lys Pro Gly Ala Ala Gly Val Met Gly Pro Arg Gly Glu Gln
                        325                 330                 335

Gly Pro Thr Gly Pro Thr Gly Pro Ala Gly Pro Arg Gly Leu Gln Gly
                        340                 345                 350

Leu Gln Gly Leu Gln Gly Glu Arg Gly Glu Gln Gly Pro Thr Gly Pro
                        355                 360                 365

Ala Gly Pro Arg Gly Leu Gln Gly Glu Arg Gly Glu Gln Gly Pro Thr
                        370                 375                 380

Gly Leu Ala Gly Lys Ala Gly Glu Ala Gly Ala Lys Gly Glu Thr Gly
        385                 390                 395                 400

Pro Ala Gly Pro Gln Gly Pro Arg Gly Glu Gln Gly Pro Gln Gly Leu
                        405                 410                 415

Pro Gly Lys Asp Gly Glu Ala Gly Ala Gln Gly Pro Ala Gly Pro Met
                        420                 425                 430

Gly Pro Ala Gly Glu Arg Gly Glu Lys Gly Glu Pro Gly Thr Gln Gly
                        435                 440                 445

Ala Lys Gly Asp Arg Gly Glu Thr Gly Pro Val Gly Pro Arg Gly Glu
                        450                 455                 460

Arg Gly Glu Ala Gly Pro Ala Gly Lys Asp Gly Glu Arg Gly Pro Val
        465                 470                 475                 480

Gly Pro Ala Gly Lys Asp Gly Gln Asn Gly Gln Asp Gly Leu Pro Gly
                        485                 490                 495
```

```
Lys Asp Gly Lys Asp Gly Gln Asn Gly Lys Asp Gly Leu Pro Gly Lys
            500                 505                 510

Asp Gly Lys Asp Gly Gln Asn Gly Lys Asp Gly Leu Pro Gly Lys Asp
            515                 520                 525

Gly Lys Asp Gly Gln Asp Gly Lys Asp Gly Leu Pro Gly Lys Asp Gly
            530                 535                 540

Lys Asp Gly Leu Pro Gly Lys Asp Gly Lys Asp Gly Gln Pro Gly Lys
545                 550                 555                 560

Pro Gly Lys Tyr

<210> SEQ ID NO 31
<211> LENGTH: 564
<212> TYPE: PRT
<213> ORGANISM: Artificial Sequence
<220> FEATURE:
<223> OTHER INFORMATION: Chimeric collagen like proteins

<400> SEQUENCE: 31

Met Asn His Lys Val His Met His His His His His Asp Glu Gln
1               5                   10                  15

Glu Glu Lys Ala Lys Val Arg Thr Glu Leu Ile Gln Glu Leu Ala Gln
            20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
            50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
            85                  90                  95

Gly Glu Gln Gly Pro Thr Gly Pro Thr Gly Pro Ala Gly Pro Arg Gly
            100                 105                 110

Leu Gln Gly Leu Gln Gly Leu Gln Gly Glu Arg Gly Glu Gln Gly Pro
            115                 120                 125

Thr Gly Pro Ala Gly Pro Arg Gly Leu Gln Gly Glu Arg Gly Glu Gln
            130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
            165                 170                 175

Gln Gly Leu Pro Gly Lys Asp Gly Glu Ala Gly Ala Gln Gly Pro Ala
            180                 185                 190

Gly Pro Met Gly Pro Ala Gly Glu Arg Gly Glu Lys Gly Glu Pro Gly
            195                 200                 205

Thr Gln Gly Ala Lys Gly Asp Arg Gly Glu Thr Gly Pro Val Gly Pro
            210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
            245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
            275                 280                 285
```

```
Gly Lys Asp Gly Lys Asp Gly Gln Asp Gly Lys Asp Gly Leu Pro Gly
            290                 295                 300
Lys Asp Gly Lys Asp Gly Leu Pro Gly Lys Asp Gly Lys Asp Gly Gln
305                 310                 315                 320
Pro Gly Lys Pro Gly Phe Pro Gly Glu Arg Gly Pro Arg Gly Glu Gln
                325                 330                 335
Gly Pro Thr Gly Pro Thr Gly Ala Gly Pro Arg Gly Leu Gln Gly
            340                 345                 350
Leu Gln Gly Leu Gln Gly Glu Arg Gly Glu Gln Gly Thr Gly Pro
            355                 360                 365
Ala Gly Pro Arg Gly Leu Gln Gly Glu Arg Gly Glu Gln Gly Pro Thr
370                 375                 380
Gly Leu Ala Gly Lys Ala Gly Glu Ala Gly Ala Lys Gly Glu Thr Gly
385                 390                 395                 400
Pro Ala Gly Pro Gln Gly Pro Arg Gly Glu Gln Gly Pro Gln Gly Leu
                405                 410                 415
Pro Gly Lys Asp Gly Glu Ala Gly Ala Gln Gly Pro Ala Gly Pro Met
                420                 425                 430
Gly Pro Ala Gly Glu Arg Gly Glu Lys Gly Glu Pro Gly Thr Gln Gly
            435                 440                 445
Ala Lys Gly Asp Arg Gly Glu Thr Gly Pro Val Gly Pro Arg Gly Glu
450                 455                 460
Arg Gly Glu Ala Gly Pro Ala Gly Lys Asp Gly Glu Arg Gly Pro Val
465                 470                 475                 480
Gly Pro Ala Gly Lys Asp Gly Gln Asn Gly Gln Asp Gly Leu Pro Gly
                485                 490                 495
Lys Asp Gly Lys Asp Gly Gln Asn Gly Lys Asp Gly Leu Pro Gly Lys
                500                 505                 510
Asp Gly Lys Asp Gly Gln Asn Gly Lys Asp Gly Leu Pro Gly Lys Asp
            515                 520                 525
Gly Lys Asp Gly Gln Asp Gly Lys Asp Gly Leu Pro Gly Lys Asp Gly
            530                 535                 540
Lys Asp Gly Leu Pro Gly Lys Asp Gly Lys Asp Gly Gln Pro Gly Lys
545                 550                 555                 560
Pro Gly Lys Tyr

<210> SEQ ID NO 32
<211> LENGTH: 570
<212> TYPE: PRT
<213> ORGANISM: Artificial Sequence
<220> FEATURE:
<223> OTHER INFORMATION: Chimeric collagen like proteins

<400> SEQUENCE: 32

Met Asn His Lys Val His Met His His His His His Asp Glu Gln
1               5                   10                  15
Glu Glu Lys Ala Lys Val Arg Thr Glu Leu Ile Gln Glu Leu Ala Gln
                20                  25                  30
Gly Leu Gly Gly Phe Glu Lys Lys Asn Phe Pro Thr Leu Gly Asp Glu
            35                  40                  45
Asp Leu Asp His Thr Tyr Met Thr Lys Leu Leu Thr Tyr Leu Gln Glu
        50                  55                  60
Arg Glu Gln Ala Glu Asn Ser Trp Arg Lys Arg Leu Leu Lys Gly Ile
65                  70                  75                  80
Gln Asp His Ala Leu Asp Leu Val Pro Arg Gly Ser Pro Gly Pro Arg
```

-continued

```
                        85                  90                  95
Gly Glu Gln Gly Pro Thr Gly Pro Thr Gly Pro Ala Gly Pro Arg Gly
                100                 105                 110
Leu Gln Gly Leu Gln Gly Leu Gln Gly Glu Arg Gly Glu Gln Gly Pro
            115                 120                 125
Thr Gly Pro Ala Gly Pro Arg Gly Leu Gln Gly Glu Arg Gly Glu Gln
        130                 135                 140
Gly Pro Thr Gly Leu Ala Gly Lys Ala Gly Glu Ala Gly Ala Lys Gly
145                 150                 155                 160
Glu Thr Gly Pro Ala Gly Pro Gln Gly Arg Gly Glu Gln Gly Pro
                165                 170                 175
Gln Gly Leu Pro Gly Lys Asp Gly Glu Ala Gly Ala Gln Gly Pro Ala
                180                 185                 190
Gly Pro Met Gly Pro Ala Gly Glu Arg Gly Glu Lys Gly Glu Pro Gly
                195                 200                 205
Thr Gln Gly Ala Lys Gly Asp Arg Gly Glu Thr Gly Pro Val Gly Pro
        210                 215                 220
Arg Gly Glu Arg Gly Glu Ala Gly Pro Ala Gly Lys Asp Gly Glu Arg
225                 230                 235                 240
Gly Pro Val Gly Pro Ala Gly Lys Asp Gly Gln Asn Gly Gln Asp Gly
                245                 250                 255
Leu Pro Gly Lys Asp Gly Lys Asp Gly Gln Asn Gly Lys Asp Gly Leu
            260                 265                 270
Pro Gly Lys Asp Gly Lys Asp Gly Gln Asn Gly Lys Asp Gly Leu Pro
        275                 280                 285
Gly Lys Asp Gly Lys Asp Gly Gln Asp Gly Lys Asp Gly Leu Pro Gly
        290                 295                 300
Lys Asp Gly Lys Asp Gly Leu Pro Gly Lys Asp Gly Lys Asp Gly Gln
305                 310                 315                 320
Pro Gly Lys Pro Gly Pro Leu Gly Ile Ala Gly Ile Thr Gly Ala Arg
                325                 330                 335
Gly Pro Arg Gly Glu Gln Gly Pro Thr Gly Pro Thr Gly Pro Ala Gly
            340                 345                 350
Pro Arg Gly Leu Gln Gly Leu Gln Gly Leu Gln Gly Glu Arg Gly Glu
        355                 360                 365
Gln Gly Pro Thr Gly Pro Ala Gly Pro Arg Gly Leu Gln Gly Glu Arg
    370                 375                 380
Gly Glu Gln Gly Pro Thr Gly Leu Ala Gly Lys Ala Gly Glu Ala Gly
385                 390                 395                 400
Ala Lys Gly Glu Thr Gly Pro Ala Gly Pro Gln Gly Pro Arg Gly Glu
                405                 410                 415
Gln Gly Pro Gln Gly Leu Pro Gly Lys Asp Gly Glu Ala Gly Ala Gln
            420                 425                 430
Gly Pro Ala Gly Pro Met Gly Pro Ala Gly Glu Arg Gly Glu Lys Gly
        435                 440                 445
Glu Pro Gly Thr Gln Gly Ala Lys Gly Asp Arg Gly Glu Thr Gly Pro
    450                 455                 460
Val Gly Pro Arg Gly Glu Arg Gly Glu Ala Gly Pro Ala Gly Lys Asp
465                 470                 475                 480
Gly Glu Arg Gly Pro Val Gly Pro Ala Gly Lys Asp Gly Gln Asn Gly
                485                 490                 495
Gln Asp Gly Leu Pro Gly Lys Asp Gly Lys Asp Gly Gln Asn Gly Lys
            500                 505                 510
```

```
Asp Gly Leu Pro Gly Lys Asp Gly Lys Asp Gly Gln Asn Gly Lys Asp
            515                 520                 525

Gly Leu Pro Gly Lys Asp Gly Lys Asp Gly Gln Asp Gly Lys Asp Gly
        530                 535                 540

Leu Pro Gly Lys Asp Gly Lys Asp Gly Leu Pro Gly Lys Asp Gly Lys
545                 550                 555                 560

Asp Gly Gln Pro Gly Lys Pro Gly Lys Tyr
                565                 570

<210> SEQ ID NO 33
<211> LENGTH: 582
<212> TYPE: PRT
<213> ORGANISM: Artificial Sequence
<220> FEATURE:
<223> OTHER INFORMATION: Chimeric collagen like proteins

<400> SEQUENCE: 33

Met Asn His Lys Val His Met His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
        50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
                85                  90                  95

Gly Glu Gln Gly Pro Thr Gly Pro Thr Gly Pro Ala Gly Pro Arg Gly
            100                 105                 110

Leu Gln Gly Leu Gln Gly Leu Gln Gly Glu Arg Gly Glu Gln Gly Pro
        115                 120                 125

Thr Gly Pro Ala Gly Pro Arg Gly Leu Gln Gly Glu Arg Gly Glu Gln
    130                 135                 140

Gly Pro Thr Gly Leu Ala Gly Lys Ala Gly Glu Ala Gly Ala Lys Gly
145                 150                 155                 160

Glu Thr Gly Pro Ala Gly Pro Gln Gly Pro Arg Gly Glu Gln Gly Pro
                165                 170                 175

Gln Gly Leu Pro Gly Lys Asp Gly Glu Ala Gly Ala Gln Gly Pro Ala
            180                 185                 190

Gly Pro Met Gly Pro Ala Gly Glu Arg Gly Glu Lys Gly Glu Pro Gly
        195                 200                 205

Thr Gln Gly Ala Lys Gly Asp Arg Gly Glu Thr Gly Pro Val Gly Pro
    210                 215                 220

Arg Gly Glu Arg Gly Glu Ala Gly Pro Ala Gly Lys Asp Gly Glu Arg
225                 230                 235                 240

Gly Pro Val Gly Pro Ala Gly Lys Asp Gly Gln Asn Gly Gln Asp Gly
                245                 250                 255

Leu Pro Gly Lys Asp Gly Lys Asp Gly Gln Asn Gly Lys Asp Gly Leu
            260                 265                 270

Pro Gly Lys Asp Gly Lys Asp Gly Gln Asn Gly Lys Asp Gly Leu Pro
        275                 280                 285

Gly Lys Asp Gly Lys Asp Gly Gln Asp Gly Lys Asp Gly Leu Pro Gly
    290                 295                 300
```

```
Lys Asp Gly Lys Asp Gly Leu Pro Gly Lys Asp Gly Lys Asp Gly Gln
305                 310                 315                 320

Pro Gly Lys Pro Gly Ala Gln Gly Pro Pro Gly Ala Pro Gly Pro Leu
            325                 330                 335

Gly Ile Ala Gly Ile Thr Gly Ala Arg Gly Leu Ala Gly Pro Arg Gly
            340                 345                 350

Glu Gln Gly Pro Thr Gly Pro Thr Gly Pro Ala Gly Pro Arg Gly Leu
            355                 360                 365

Gln Gly Leu Gln Gly Leu Gln Gly Glu Arg Gly Glu Gln Gly Pro Thr
370                 375                 380

Gly Pro Ala Gly Pro Arg Gly Leu Gln Gly Glu Arg Gly Glu Gln Gly
385                 390                 395                 400

Pro Thr Gly Leu Ala Gly Lys Ala Gly Glu Ala Gly Ala Lys Gly Glu
            405                 410                 415

Thr Gly Pro Ala Gly Pro Gln Gly Pro Arg Gly Glu Gln Gly Pro Gln
            420                 425                 430

Gly Leu Pro Gly Lys Asp Gly Glu Ala Gly Ala Gln Gly Pro Ala Gly
            435                 440                 445

Pro Met Gly Pro Ala Gly Glu Arg Gly Glu Lys Gly Glu Pro Gly Thr
    450                 455                 460

Gln Gly Ala Lys Gly Asp Arg Gly Glu Thr Gly Pro Val Gly Pro Arg
465                 470                 475                 480

Gly Glu Arg Gly Glu Ala Gly Pro Ala Gly Lys Asp Gly Glu Arg Gly
                485                 490                 495

Pro Val Gly Pro Ala Gly Lys Asp Gly Gln Asn Gly Gln Asp Gly Leu
            500                 505                 510

Pro Gly Lys Asp Gly Lys Asp Gly Gln Asn Gly Lys Asp Gly Leu Pro
            515                 520                 525

Gly Lys Asp Gly Lys Asp Gly Gln Asn Gly Lys Asp Gly Leu Pro Gly
            530                 535                 540

Lys Asp Gly Lys Asp Gly Gln Asp Gly Lys Asp Gly Leu Pro Gly Lys
545                 550                 555                 560

Asp Gly Lys Asp Gly Leu Pro Gly Lys Asp Gly Lys Asp Gly Gln Pro
                565                 570                 575

Gly Lys Pro Gly Lys Tyr
            580

<210> SEQ ID NO 34
<211> LENGTH: 570
<212> TYPE: PRT
<213> ORGANISM: Artificial Sequence
<220> FEATURE:
<223> OTHER INFORMATION: Chimeric collagen like proteins

<400> SEQUENCE: 34

Met Asn His Lys Val His Met His His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
    50                  55                  60

Arg Glu Gln Ala Glu Asn Ser Trp Arg Lys Arg Leu Leu Lys Gly Ile
65                  70                  75                  80
```

```
Gln Asp His Ala Leu Asp Leu Val Pro Arg Gly Ser Pro Gly Pro Arg
                85                  90                  95
Gly Glu Gln Gly Pro Thr Gly Pro Thr Gly Pro Ala Gly Pro Arg Gly
            100                 105                 110
Leu Gln Gly Leu Gln Gly Leu Gln Gly Glu Arg Gly Glu Gln Gly Pro
        115                 120                 125
Thr Gly Pro Ala Gly Pro Arg Gly Leu Gln Gly Glu Arg Gly Glu Gln
    130                 135                 140
Gly Pro Thr Gly Leu Ala Gly Lys Ala Gly Glu Ala Gly Ala Lys Gly
145                 150                 155                 160
Glu Thr Gly Pro Ala Gly Pro Gln Gly Pro Arg Gly Glu Gln Gly Pro
                165                 170                 175
Gln Gly Leu Pro Gly Lys Asp Gly Glu Ala Gly Ala Gln Gly Pro Ala
            180                 185                 190
Gly Pro Met Gly Pro Ala Gly Glu Arg Gly Glu Lys Gly Glu Pro Gly
        195                 200                 205
Thr Gln Gly Ala Lys Gly Asp Arg Gly Glu Thr Gly Pro Val Gly Pro
    210                 215                 220
Arg Gly Glu Arg Gly Glu Ala Gly Pro Ala Gly Lys Asp Gly Glu Arg
225                 230                 235                 240
Gly Pro Val Gly Pro Ala Gly Lys Asp Gly Gln Asn Gly Gln Asp Gly
                245                 250                 255
Leu Pro Gly Lys Asp Gly Lys Asp Gly Gln Asn Gly Lys Asp Gly Leu
            260                 265                 270
Pro Gly Lys Asp Gly Lys Asp Gly Gln Asn Gly Lys Asp Gly Leu Pro
        275                 280                 285
Gly Lys Asp Gly Lys Asp Gly Gln Asp Gly Lys Asp Gly Leu Pro Gly
    290                 295                 300
Lys Asp Gly Lys Asp Gly Leu Pro Gly Lys Asp Gly Lys Asp Gly Gln
305                 310                 315                 320
Pro Gly Lys Pro Gly Pro Gln Gly Leu Ala Gly Gln Arg Gly Ile Val
                325                 330                 335
Gly Pro Arg Gly Glu Gln Gly Pro Thr Gly Pro Thr Gly Pro Ala Gly
            340                 345                 350
Pro Arg Gly Leu Gln Gly Leu Gln Gly Leu Gln Gly Glu Arg Gly Glu
        355                 360                 365
Gln Gly Pro Thr Gly Pro Ala Gly Pro Arg Gly Leu Gln Gly Glu Arg
    370                 375                 380
Gly Glu Gln Gly Pro Thr Gly Leu Ala Gly Lys Ala Gly Glu Ala Gly
385                 390                 395                 400
Ala Lys Gly Glu Thr Gly Pro Ala Gly Pro Gln Gly Pro Arg Gly Glu
                405                 410                 415
Gln Gly Pro Gln Gly Leu Pro Gly Lys Asp Gly Glu Ala Gly Ala Gln
            420                 425                 430
Gly Pro Ala Gly Pro Met Gly Pro Ala Gly Glu Arg Gly Glu Lys Gly
        435                 440                 445
Glu Pro Gly Thr Gln Gly Ala Lys Gly Asp Arg Gly Glu Thr Gly Pro
    450                 455                 460
Val Gly Pro Arg Gly Glu Arg Gly Glu Ala Gly Pro Ala Gly Lys Asp
465                 470                 475                 480
Gly Glu Arg Gly Pro Val Gly Pro Ala Gly Lys Asp Gly Gln Asn Gly
                485                 490                 495
```

```
Gln Asp Gly Leu Pro Gly Lys Asp Gly Lys Asp Gly Gln Asn Gly Lys
                500                 505                 510
Asp Gly Leu Pro Gly Lys Asp Gly Lys Asp Gly Gln Asn Gly Lys Asp
            515                 520                 525
Gly Leu Pro Gly Lys Asp Gly Lys Asp Gly Gln Asp Gly Lys Asp Gly
        530                 535                 540
Leu Pro Gly Lys Asp Gly Lys Asp Gly Leu Pro Gly Lys Asp Gly Lys
545                 550                 555                 560
Asp Gly Gln Pro Gly Lys Pro Gly Lys Tyr
                565                 570

<210> SEQ ID NO 35
<211> LENGTH: 582
<212> TYPE: PRT
<213> ORGANISM: Artificial Sequence
<220> FEATURE:
<223> OTHER INFORMATION: Chimeric collagen like proteins

<400> SEQUENCE: 35

Met Asn His Lys Val His Met His His His His His Asp Glu Gln
1               5                   10                  15
Glu Glu Lys Ala Lys Val Arg Thr Glu Leu Ile Gln Glu Leu Ala Gln
                20                  25                  30
Gly Leu Gly Gly Phe Glu Lys Lys Asn Phe Pro Thr Leu Gly Asp Glu
            35                  40                  45
Asp Leu Asp His Thr Tyr Met Thr Lys Leu Leu Thr Tyr Leu Gln Glu
        50                  55                  60
Arg Glu Gln Ala Glu Asn Ser Trp Arg Lys Arg Leu Leu Lys Gly Ile
65                  70                  75                  80
Gln Asp His Ala Leu Asp Leu Val Pro Arg Gly Ser Pro Gly Pro Arg
                85                  90                  95
Gly Glu Gln Gly Pro Thr Gly Pro Thr Gly Pro Ala Gly Pro Arg Gly
            100                 105                 110
Leu Gln Gly Leu Gln Gly Leu Gln Gly Glu Arg Gly Glu Gln Gly Pro
        115                 120                 125
Thr Gly Pro Ala Gly Pro Arg Gly Leu Gln Gly Glu Arg Gly Glu Gln
    130                 135                 140
Gly Pro Thr Gly Leu Ala Gly Lys Ala Gly Glu Ala Gly Ala Lys Gly
145                 150                 155                 160
Glu Thr Gly Pro Ala Gly Pro Gln Gly Arg Gly Glu Gln Gly Pro
                165                 170                 175
Gln Gly Leu Pro Gly Lys Asp Gly Glu Ala Gly Ala Gln Gly Pro Ala
            180                 185                 190
Gly Pro Met Gly Pro Ala Gly Glu Arg Gly Glu Lys Gly Glu Pro Gly
        195                 200                 205
Thr Gln Gly Ala Lys Gly Asp Arg Gly Glu Thr Gly Pro Val Gly Pro
    210                 215                 220
Arg Gly Glu Arg Gly Glu Ala Gly Pro Ala Gly Lys Asp Gly Glu Arg
225                 230                 235                 240
Gly Pro Val Gly Pro Ala Gly Lys Asp Gly Gln Asn Gly Gln Asp Gly
                245                 250                 255
Leu Pro Gly Lys Asp Gly Lys Asp Gly Gln Asn Gly Lys Asp Gly Leu
            260                 265                 270
Pro Gly Lys Asp Gly Lys Asp Gly Gln Asn Gly Lys Asp Gly Leu Pro
        275                 280                 285
```

```
Gly Lys Asp Gly Lys Asp Gly Gln Asp Gly Lys Asp Gly Leu Pro Gly
    290                 295                 300
Lys Asp Gly Lys Asp Gly Leu Pro Gly Lys Asp Gly Lys Asp Gly Gln
305                 310                 315                 320
Pro Gly Lys Pro Gly Pro Ser Gly Ala Glu Gly Pro Pro Gly Pro Gln
                325                 330                 335
Gly Leu Ala Gly Gln Arg Gly Ile Val Gly Leu Pro Gly Pro Arg Gly
            340                 345                 350
Glu Gln Gly Pro Thr Gly Pro Thr Gly Pro Ala Gly Pro Arg Gly Leu
        355                 360                 365
Gln Gly Leu Gln Gly Leu Gln Gly Glu Arg Gly Glu Gln Gly Pro Thr
    370                 375                 380
Gly Pro Ala Gly Pro Arg Gly Leu Gln Gly Glu Arg Gly Glu Gln Gly
385                 390                 395                 400
Pro Thr Gly Leu Ala Gly Lys Ala Gly Glu Ala Gly Ala Lys Gly Glu
                405                 410                 415
Thr Gly Pro Ala Gly Pro Gln Gly Pro Arg Gly Glu Gln Gly Pro Gln
            420                 425                 430
Gly Leu Pro Gly Lys Asp Gly Glu Ala Gly Ala Gln Gly Pro Ala Gly
        435                 440                 445
Pro Met Gly Pro Ala Gly Glu Arg Gly Glu Lys Gly Glu Pro Gly Thr
    450                 455                 460
Gln Gly Ala Lys Gly Asp Arg Gly Glu Thr Gly Pro Val Gly Pro Arg
465                 470                 475                 480
Gly Glu Arg Gly Glu Ala Gly Pro Ala Gly Lys Asp Gly Glu Arg Gly
                485                 490                 495
Pro Val Gly Pro Ala Gly Lys Asp Gly Gln Asn Gly Gln Asp Gly Leu
            500                 505                 510
Pro Gly Lys Asp Gly Lys Asp Gly Gln Asn Gly Lys Asp Gly Leu Pro
        515                 520                 525
Gly Lys Asp Gly Lys Asp Gly Gln Asn Gly Lys Asp Gly Leu Pro Gly
    530                 535                 540
Lys Asp Gly Lys Asp Gly Gln Asp Gly Lys Asp Gly Leu Pro Gly Lys
545                 550                 555                 560
Asp Gly Lys Asp Gly Leu Pro Gly Lys Asp Gly Lys Asp Gly Gln Pro
                565                 570                 575
Gly Lys Pro Gly Lys Tyr
            580

<210> SEQ ID NO 36
<211> LENGTH: 282
<212> TYPE: PRT
<213> ORGANISM: Artificial Sequence
<220> FEATURE:
<223> OTHER INFORMATION: Reincombinant collagen like protein

<400> SEQUENCE: 36

Met Asn His Lys Val His Met His His His His Asp Glu Gln
1               5                   10                  15
Glu Glu Lys Ala Lys Val Arg Thr Glu Leu Ile Gln Glu Leu Ala Gln
            20                  25                  30
Gly Leu Gly Gly Phe Glu Lys Lys Asn Phe Pro Thr Leu Gly Asp Glu
        35                  40                  45
Asp Leu Asp His Thr Tyr Met Thr Lys Leu Leu Thr Tyr Leu Gln Glu
    50                  55                  60
```

```
Arg Glu Gln Ala Glu Asn Ser Trp Arg Lys Arg Leu Leu Lys Gly Ile
 65                  70                  75                  80

Gln Asp His Ala Leu Asp Leu Val Pro Arg Gly Ser Pro Gly Pro Arg
                 85                  90                  95

Gly Pro Arg Gly Pro Gln Gly Glu Gln Gly Pro Gln Gly Glu Arg Gly
            100                 105                 110

Phe Thr Gly Pro Gln Gly Pro Val Gly Pro Gln Gly Glu Gln Gly Pro
            115                 120                 125

Gln Gly Glu Arg Gly Phe Thr Gly Pro Gln Gly Pro Ile Gly Leu Gln
130                 135                 140

Gly Glu Gln Gly Pro Gln Gly Glu Arg Gly Phe Thr Gly Pro Gln Gly
145                 150                 155                 160

Pro Val Gly Pro Gln Gly Glu Gln Gly Pro Gln Gly Glu Arg Gly Phe
                165                 170                 175

Thr Gly Pro Gln Gly Pro Val Gly Pro Gln Gly Glu Gln Gly Pro Gln
            180                 185                 190

Gly Glu Arg Gly Phe Thr Gly Pro Gln Gly Pro Ile Gly Pro Gln Gly
            195                 200                 205

Glu Gln Gly Pro Gln Gly Glu Arg Gly Phe Thr Gly Pro Gln Gly Pro
210                 215                 220

Ile Gly Pro Gln Gly Asn Gln Gly Pro Ile Gly Pro Gln Gly Glu Gln
225                 230                 235                 240

Gly Pro Gln Gly Ala Thr Gly Pro Gln Gly Pro Gln Gly Pro Val Gly
                245                 250                 255

Pro Gln Gly Asn Gln Gly Pro Ile Gly Pro Gln Gly Pro Val Gly Pro
            260                 265                 270

Gln Gly Pro Gln Gly Gln Pro Gly Val Asn
            275                 280

<210> SEQ ID NO 37
<211> LENGTH: 285
<212> TYPE: PRT
<213> ORGANISM: Artificial Sequence
<220> FEATURE:
<223> OTHER INFORMATION: Reincombinant collagen like protein

<400> SEQUENCE: 37

Met His His His His His Gly Pro Arg Gly Pro Arg Gly Pro Gln
 1               5                  10                  15

Gly Glu Gln Gly Pro Gln Gly Glu Arg Gly Phe Thr Gly Pro Gln Gly
                 20                  25                  30

Pro Val Gly Pro Gln Gly Glu Gln Gly Pro Gln Gly Glu Arg Gly Phe
            35                  40                  45

Thr Gly Pro Gln Gly Pro Ile Gly Leu Gln Gly Glu Gln Gly Pro Gln
            50                  55                  60

Gly Glu Arg Gly Phe Thr Gly Pro Gln Gly Pro Val Gly Pro Gln Gly
 65                  70                  75                  80

Glu Gln Gly Pro Gln Gly Glu Arg Gly Phe Thr Gly Pro Gln Gly Pro
                 85                  90                  95

Val Gly Pro Gln Gly Glu Gln Gly Pro Gln Gly Glu Arg Gly Phe Thr
            100                 105                 110

Gly Pro Gln Gly Pro Ile Gly Pro Gln Gly Glu Gln Gly Pro Gln Gly
            115                 120                 125

Glu Arg Gly Phe Thr Gly Pro Gln Gly Pro Ile Gly Pro Gln Gly Asn
130                 135                 140
```

```
Gln Gly Pro Ile Gly Pro Gln Gly Glu Gln Gly Pro Gln Gly Ala Thr
145                 150                 155                 160

Gly Pro Gln Gly Pro Gln Gly Pro Val Gly Pro Gln Gly Asn Gln Gly
                165                 170                 175

Pro Ile Gly Pro Gln Gly Pro Val Gly Pro Gln Gly Pro Gln Gly Gln
                180                 185                 190

Pro Gly Val Asn Gly Pro Arg Pro Ser Ile Glu Gln Val Met Pro Trp
            195                 200                 205

Leu His Leu Ile Phe Asp Ala Tyr Glu Asp Tyr Lys Ala Gln Arg Ala
210                 215                 220

Arg Glu Ala Arg Glu Leu Glu Arg Leu Ala Ala Glu Ala Leu Glu
225                 230                 235                 240

Gln Ala Ala Arg Glu Ala Ala Glu Arg Glu Val Ala Ala Ala Ile Glu
                245                 250                 255

Ala Ala Asn Ala Glu Ala Glu Ile Met Leu Asp Asp Glu Thr His Ala
                260                 265                 270

Glu Gly Gly Lys Lys Lys Lys Arg Lys His Lys Asp
                275                 280                 285

<210> SEQ ID NO 38
<211> LENGTH: 477
<212> TYPE: PRT
<213> ORGANISM: Artificial Sequence
<220> FEATURE:
<223> OTHER INFORMATION: Reincombinant collagen like protein

<400> SEQUENCE: 38

Met Asn His Lys Val His Met His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
                85                  90                  95

Gly Pro Arg Gly Pro Gln Gly Glu Gln Gly Pro Gln Gly Glu Arg Gly
                100                 105                 110

Phe Thr Gly Pro Gln Gly Pro Val Gly Pro Gln Gly Glu Gln Gly Pro
            115                 120                 125

Gln Gly Glu Arg Gly Phe Thr Gly Pro Gln Gly Ile Gly Leu Gln
130                 135                 140

Gly Glu Gln Gly Pro Gln Gly Glu Arg Gly Phe Thr Gly Pro Gln Gly
145                 150                 155                 160

Pro Val Gly Pro Gln Gly Glu Gln Gly Pro Gln Gly Glu Arg Gly Phe
                165                 170                 175

Thr Gly Pro Gln Gly Pro Val Gly Pro Gln Gly Glu Gln Gly Pro Gln
            180                 185                 190

Gly Glu Arg Gly Phe Thr Gly Pro Gln Gly Ile Gly Pro Gln Gly
                195                 200                 205

Glu Gln Gly Pro Gln Gly Glu Arg Gly Phe Thr Gly Pro Gln Gly Pro
210                 215                 220
```

Ile Gly Pro Gln Gly Asn Gln Gly Pro Ile Gly Pro Gln Gly Glu Gln
225                 230                 235                 240

Gly Pro Gln Gly Ala Thr Gly Pro Gln Gly Pro Gln Gly Pro Val Gly
                245                 250                 255

Pro Gln Gly Asn Gln Gly Pro Ile Gly Pro Gln Gly Pro Val Gly Pro
                260                 265                 270

Gln Gly Pro Gln Gly Gln Pro Gly Val Asn Gly Ala Ala Gly Val Met
                275                 280                 285

Gly Pro Arg Gly Pro Arg Gly Pro Gln Gly Glu Gln Gly Pro Gln Gly
            290                 295                 300

Glu Arg Gly Phe Thr Gly Pro Gln Gly Pro Val Gly Pro Gln Gly Glu
305                 310                 315                 320

Gln Gly Pro Gln Gly Glu Arg Gly Phe Thr Gly Pro Gln Gly Pro Ile
                325                 330                 335

Gly Leu Gln Gly Glu Gln Gly Pro Gln Gly Glu Arg Gly Phe Thr Gly
                340                 345                 350

Pro Gln Gly Pro Val Gly Pro Gln Gly Glu Gln Gly Pro Gln Gly Glu
                355                 360                 365

Arg Gly Phe Thr Gly Pro Gln Gly Pro Val Gly Pro Gln Gly Glu Gln
            370                 375                 380

Gly Pro Gln Gly Glu Arg Gly Phe Thr Gly Pro Gln Gly Pro Ile Gly
385                 390                 395                 400

Pro Gln Gly Glu Gln Gly Pro Gln Gly Glu Arg Gly Phe Thr Gly Pro
                405                 410                 415

Gln Gly Pro Ile Gly Pro Gln Gly Asn Gln Gly Pro Ile Gly Pro Gln
                420                 425                 430

Gly Glu Gln Gly Pro Gln Gly Ala Thr Gly Pro Gln Gly Pro Gln Gly
            435                 440                 445

Pro Val Gly Pro Gln Gly Asn Gln Gly Pro Ile Gly Pro Gln Gly Pro
                450                 455                 460

Val Gly Pro Gln Gly Pro Gln Gln Pro Gly Val Asn
465                 470                 475

<210> SEQ ID NO 39
<211> LENGTH: 477
<212> TYPE: PRT
<213> ORGANISM: Artificial Sequence
<220> FEATURE:
<223> OTHER INFORMATION: Reincombinant collagen like protein

<400> SEQUENCE: 39

Met Asn His Lys Val His Met His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
        50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
                85                  90                  95

Gly Pro Arg Gly Pro Gln Gly Glu Gln Gly Pro Gln Gly Glu Arg Gly
                100                 105                 110

```
Phe Thr Gly Pro Gln Gly Pro Val Gly Pro Gln Gly Glu Gln Gly Pro
            115                 120                 125
Gln Gly Glu Arg Gly Phe Thr Gly Pro Gln Gly Ile Gly Leu Gln
130                 135                 140
Gly Glu Gln Gly Pro Gln Gly Glu Arg Gly Phe Thr Gly Pro Gln Gly
145                 150                 155                 160
Pro Val Gly Pro Gln Gly Glu Gln Pro Gln Gly Glu Arg Gly Phe
                165                 170                 175
Thr Gly Pro Gln Gly Pro Val Gly Pro Gln Gly Glu Gln Gly Pro Gln
            180                 185                 190
Gly Glu Arg Gly Phe Thr Gly Pro Gln Gly Ile Gly Pro Gln Gly
            195                 200                 205
Glu Gln Gly Pro Gln Gly Glu Arg Gly Phe Thr Gly Pro Gln Gly Pro
210                 215                 220
Ile Gly Pro Gln Gly Asn Gln Gly Pro Ile Gly Pro Gln Gly Glu Gln
225                 230                 235                 240
Gly Pro Gln Gly Ala Thr Gly Pro Gln Gly Pro Gln Gly Pro Val Gly
                245                 250                 255
Pro Gln Gly Asn Gln Gly Pro Ile Gly Pro Gln Gly Pro Val Gly Pro
                260                 265                 270
Gln Gly Pro Gln Gly Gln Pro Gly Val Asn Gly Phe Pro Gly Glu Arg
                275                 280                 285
Gly Pro Arg Gly Pro Arg Gly Pro Gln Gly Glu Gln Gly Pro Gln Gly
            290                 295                 300
Glu Arg Gly Phe Thr Gly Pro Gln Gly Pro Val Gly Pro Gln Gly Glu
305                 310                 315                 320
Gln Gly Pro Gln Gly Glu Arg Gly Phe Thr Gly Pro Gln Gly Pro Ile
                325                 330                 335
Gly Leu Gln Gly Glu Gln Gly Pro Gln Gly Glu Arg Gly Phe Thr Gly
            340                 345                 350
Pro Gln Gly Pro Val Gly Pro Gln Gly Glu Gly Pro Gln Gly Glu
            355                 360                 365
Arg Gly Phe Thr Gly Pro Gln Gly Pro Val Gly Pro Gln Gly Glu Gln
370                 375                 380
Gly Pro Gln Gly Glu Arg Gly Phe Thr Gly Pro Gln Gly Pro Ile Gly
385                 390                 395                 400
Pro Gln Gly Glu Gln Gly Pro Gln Gly Glu Arg Gly Phe Thr Gly Pro
                405                 410                 415
Gln Gly Pro Ile Gly Pro Gln Gly Asn Gln Gly Pro Ile Gly Pro Gln
            420                 425                 430
Gly Glu Gln Gly Pro Gln Gly Ala Thr Gly Pro Gln Gly Pro Gln Gly
            435                 440                 445
Pro Val Gly Pro Gln Gly Asn Gln Gly Pro Ile Gly Pro Gln Gly Pro
            450                 455                 460
Val Gly Pro Gln Gly Pro Gln Gly Gln Pro Gly Val Asn
465                 470                 475

<210> SEQ ID NO 40
<211> LENGTH: 480
<212> TYPE: PRT
<213> ORGANISM: Artificial Sequence
<220> FEATURE:
<223> OTHER INFORMATION: Reincombinant collagen like protein

<400> SEQUENCE: 40
```

-continued

```
Met Asn His Lys Val His Met His His His His His Asp Glu Gln
1               5               10                      15

Glu Glu Lys Ala Lys Val Arg Thr Glu Leu Ile Gln Glu Leu Ala Gln
                20              25                      30

Gly Leu Gly Gly Phe Glu Lys Lys Asn Phe Pro Thr Leu Gly Asp Glu
                35              40                      45

Asp Leu Asp His Thr Tyr Met Thr Lys Leu Leu Thr Tyr Leu Gln Glu
        50              55                      60

Arg Glu Gln Ala Glu Asn Ser Trp Arg Lys Arg Leu Leu Lys Gly Ile
65                      70              75                      80

Gln Asp His Ala Leu Asp Leu Val Pro Arg Gly Ser Pro Gly Pro Arg
                85              90                      95

Gly Pro Arg Gly Pro Gln Gly Glu Gln Gly Pro Gln Gly Glu Arg Gly
                100             105                     110

Phe Thr Gly Pro Gln Gly Pro Val Gly Pro Gln Gly Glu Gln Gly Pro
                115             120                     125

Gln Gly Glu Arg Gly Phe Thr Gly Pro Gln Gly Ile Gly Leu Gln
            130             135                     140

Gly Glu Gln Gly Pro Gln Gly Glu Arg Gly Phe Thr Gly Pro Gln Gly
145                     150             155                     160

Pro Val Gly Pro Gln Gly Glu Gln Gly Pro Gln Gly Glu Arg Gly Phe
                165             170                     175

Thr Gly Pro Gln Gly Pro Val Gly Pro Gln Gly Glu Gln Gly Pro Gln
                180             185                     190

Gly Glu Arg Gly Phe Thr Gly Pro Gln Gly Ile Gly Pro Gln Gly
            195             200                     205

Glu Gln Gly Pro Gln Gly Glu Arg Gly Phe Thr Gly Pro Gln Gly Pro
            210             215                     220

Ile Gly Pro Gln Gly Asn Gln Gly Pro Ile Gly Pro Gln Gly Glu Gln
225                     230             235                     240

Gly Pro Gln Gly Ala Thr Gly Pro Gln Gly Pro Gln Gly Pro Val Gly
                245             250                     255

Pro Gln Gly Asn Gln Gly Pro Ile Gly Pro Gln Gly Pro Val Gly Pro
            260             265                     270

Gln Gly Pro Gln Gly Gln Pro Gly Val Asn Gly Pro Leu Gly Ile Ala
            275             280                     285

Gly Ile Thr Gly Ala Arg Gly Pro Arg Gly Pro Gln Gly Glu Gln Gly
        290             295                     300

Pro Gln Gly Glu Arg Gly Phe Thr Gly Pro Gln Gly Pro Val Gly Pro
305                     310             315                     320

Gln Gly Glu Gln Gly Pro Gln Gly Glu Arg Gly Phe Thr Gly Pro Gln
            325             330                     335

Gly Pro Ile Gly Leu Gln Gly Glu Gln Gly Pro Gln Gly Glu Arg Gly
            340             345                     350

Phe Thr Gly Pro Gln Gly Pro Val Gly Pro Gln Gly Glu Gln Gly Pro
                355             360                     365

Gln Gly Glu Arg Gly Phe Thr Gly Pro Gln Gly Pro Val Gly Pro Gln
            370             375                     380

Gly Glu Gln Gly Pro Gln Gly Glu Arg Gly Phe Thr Gly Pro Gln Gly
385                     390             395                     400

Pro Ile Gly Pro Gln Gly Glu Gln Gly Pro Gln Gly Glu Arg Gly Phe
                405             410                     415

Thr Gly Pro Gln Gly Pro Ile Gly Pro Gln Gly Asn Gln Gly Pro Ile
```

```
                420            425            430
Gly Pro Gln Gly Glu Gln Gly Pro Gln Gly Ala Thr Gly Pro Gln Gly
            435            440            445

Pro Gln Gly Pro Val Gly Pro Gln Gly Asn Gln Gly Pro Ile Gly Pro
            450            455            460

Gln Gly Pro Val Gly Pro Gly Gln Gly Gln Pro Gly Val Asn
465            470            475            480

<210> SEQ ID NO 41
<211> LENGTH: 492
<212> TYPE: PRT
<213> ORGANISM: Artificial Sequence
<220> FEATURE:
<223> OTHER INFORMATION: Reincombinant collagen like protein

<400> SEQUENCE: 41

Met Asn His Lys Val His Met His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Phe Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
    50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
                85                  90                  95

Gly Pro Arg Gly Pro Gln Gly Glu Gln Gly Pro Gln Gly Glu Arg Gly
            100                 105                 110

Phe Thr Gly Pro Gln Gly Pro Val Gly Pro Gln Gly Glu Gln Gly Pro
        115                 120                 125

Gln Gly Glu Arg Gly Phe Thr Gly Pro Gln Gly Pro Ile Gly Leu Gln
    130                 135                 140

Gly Glu Gln Gly Pro Gln Gly Glu Arg Gly Phe Thr Gly Pro Gln Gly
145                 150                 155                 160

Pro Val Gly Pro Gln Gly Glu Gln Gly Pro Gln Gly Glu Arg Gly Phe
                165                 170                 175

Thr Gly Pro Gln Gly Pro Val Gly Pro Gln Gly Glu Gln Gly Pro Gln
            180                 185                 190

Gly Glu Arg Gly Phe Thr Gly Pro Gln Gly Pro Ile Gly Pro Gln Gly
        195                 200                 205

Glu Gln Gly Pro Gln Gly Glu Arg Gly Phe Thr Gly Pro Gln Gly Pro
    210                 215                 220

Ile Gly Pro Gln Gly Asn Gln Gly Pro Ile Gly Pro Gln Gly Glu Gln
225                 230                 235                 240

Gly Pro Gln Gly Ala Thr Gly Pro Gln Gly Pro Gln Gly Pro Val Gly
                245                 250                 255

Pro Gln Gly Asn Gln Gly Pro Ile Gly Pro Gln Gly Pro Val Gly Pro
            260                 265                 270

Gln Gly Pro Gln Gly Gln Pro Gly Val Asn Gly Ala Gln Gly Pro Pro
        275                 280                 285

Gly Ala Pro Gly Pro Leu Gly Ile Ala Gly Ile Thr Gly Ala Arg Gly
    290                 295                 300

Leu Ala Gly Pro Arg Gly Pro Gln Gly Glu Gln Gly Pro Gln Gly Glu
```

```
305                 310                 315                 320
Arg Gly Phe Thr Gly Pro Gln Gly Pro Val Gly Pro Gln Gly Glu Gln
                325                 330                 335

Gly Pro Gln Gly Glu Arg Gly Phe Thr Gly Pro Gln Gly Pro Ile Gly
            340                 345                 350

Leu Gln Gly Glu Gln Gly Pro Gln Gly Glu Arg Gly Phe Thr Gly Pro
            355                 360                 365

Gln Gly Pro Val Gly Pro Gln Gly Glu Gln Gly Pro Gln Gly Glu Arg
        370                 375                 380

Gly Phe Thr Gly Pro Gln Gly Pro Val Gly Pro Gln Gly Glu Gln Gly
385                 390                 395                 400

Pro Gln Gly Glu Arg Gly Phe Thr Gly Pro Gln Gly Pro Ile Gly Pro
                405                 410                 415

Gln Gly Glu Gln Gly Pro Gln Gly Glu Arg Gly Phe Thr Gly Pro Gln
            420                 425                 430

Gly Pro Ile Gly Pro Gln Gly Asn Gln Gly Pro Ile Gly Pro Gln Gly
        435                 440                 445

Glu Gln Gly Pro Gln Gly Ala Thr Gly Pro Gln Gly Pro Gln Gly Pro
    450                 455                 460

Val Gly Pro Gln Gly Asn Gln Gly Pro Ile Gly Pro Gln Gly Pro Val
465                 470                 475                 480

Gly Pro Gln Gly Pro Gln Gly Gln Pro Gly Val Asn
                485                 490

<210> SEQ ID NO 42
<211> LENGTH: 480
<212> TYPE: PRT
<213> ORGANISM: Artificial Sequence
<220> FEATURE:
<223> OTHER INFORMATION: Reincombinant collagen like protein

<400> SEQUENCE: 42

Met Asn His Lys Val His Met His His His His Asp Glu Gln
1               5                   10                  15

Glu Glu Lys Ala Lys Val Arg Thr Glu Leu Ile Gln Glu Leu Ala Gln
            20                  25                  30

Gly Leu Gly Gly Phe Glu Lys Lys Asn Phe Pro Thr Leu Gly Asp Glu
        35                  40                  45

Asp Leu Asp His Thr Tyr Met Thr Lys Leu Leu Thr Tyr Leu Gln Glu
    50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Arg
                85                  90                  95

Gly Pro Arg Gly Pro Gln Gly Glu Gln Gly Pro Gln Gly Glu Arg Gly
            100                 105                 110

Phe Thr Gly Pro Gln Gly Pro Val Gly Pro Gln Gly Glu Gln Gly Pro
        115                 120                 125

Gln Gly Glu Arg Gly Phe Thr Gly Pro Gln Gly Pro Ile Gly Leu Gln
    130                 135                 140

Gly Glu Gln Gly Pro Gln Gly Glu Arg Gly Phe Thr Gly Pro Gln Gly
145                 150                 155                 160

Pro Val Gly Pro Gln Gly Glu Gln Gly Pro Gln Gly Glu Arg Gly Phe
                165                 170                 175

Thr Gly Pro Gln Gly Pro Val Gly Pro Gln Gly Glu Gln Gly Pro Gln
```

```
            180                 185                 190
Gly Glu Arg Gly Phe Thr Gly Pro Gln Gly Pro Ile Gly Pro Gln Gly
            195                 200                 205

Glu Gln Gly Pro Gln Gly Glu Arg Gly Phe Thr Gly Pro Gln Gly Pro
            210                 215                 220

Ile Gly Pro Gln Gly Asn Gln Gly Pro Ile Gly Pro Gln Gly Glu Gln
225                 230                 235                 240

Gly Pro Gln Gly Ala Thr Gly Pro Gln Gly Pro Gln Gly Pro Val Gly
                    245                 250                 255

Pro Gln Gly Asn Gln Gly Pro Ile Gly Pro Gln Gly Pro Val Gly Pro
                    260                 265                 270

Gln Gly Pro Gln Gly Gln Pro Gly Val Asn Gly Pro Gln Gly Leu Ala
                    275                 280                 285

Gly Gln Arg Gly Ile Val Gly Pro Arg Gly Pro Gln Gly Glu Gln Gly
                    290                 295                 300

Pro Gln Gly Glu Arg Gly Phe Thr Gly Pro Gln Gly Pro Val Gly Pro
305                 310                 315                 320

Gln Gly Glu Gln Gly Pro Gln Gly Glu Arg Gly Phe Thr Gly Pro Gln
                    325                 330                 335

Gly Pro Ile Gly Leu Gln Gly Glu Gln Gly Pro Gln Gly Glu Arg Gly
                    340                 345                 350

Phe Thr Gly Pro Gln Gly Pro Val Gly Pro Gln Gly Glu Gln Gly Pro
                    355                 360                 365

Gln Gly Glu Arg Gly Phe Thr Gly Pro Gln Gly Pro Val Gly Pro Gln
                    370                 375                 380

Gly Glu Gln Gly Pro Gln Gly Glu Arg Gly Phe Thr Gly Pro Gln Gly
385                 390                 395                 400

Pro Ile Gly Pro Gln Gly Glu Gln Gly Pro Gln Gly Glu Arg Gly Phe
                    405                 410                 415

Thr Gly Pro Gln Gly Pro Ile Gly Pro Gln Gly Asn Gln Gly Pro Ile
                    420                 425                 430

Gly Pro Gln Gly Glu Gln Gly Pro Gln Gly Ala Thr Gly Pro Gln Gly
                    435                 440                 445

Pro Gln Gly Pro Val Gly Pro Gln Gly Asn Gln Gly Pro Ile Gly Pro
                    450                 455                 460

Gln Gly Pro Val Gly Pro Gln Gly Pro Gln Gly Gln Pro Gly Val Asn
465                 470                 475                 480

<210> SEQ ID NO 43
<211> LENGTH: 492
<212> TYPE: PRT
<213> ORGANISM: Artificial Sequence
<220> FEATURE:
<223> OTHER INFORMATION: Reincombinant collagen like protein

<400> SEQUENCE: 43

Met Asn His Lys Val His Met His His His His His Asp Glu Gln
1                 5                   10                  15

Glu Glu Lys Ala Lys Val Arg Thr Glu Leu Ile Gln Glu Leu Ala Gln
                    20                  25                  30

Gly Leu Gly Gly Phe Glu Lys Lys Asn Phe Pro Thr Leu Gly Asp Glu
                    35                  40                  45

Asp Leu Asp His Thr Tyr Met Thr Lys Leu Leu Thr Tyr Leu Gln Glu
            50                  55                  60

Arg Glu Gln Ala Glu Asn Ser Trp Arg Lys Arg Leu Leu Lys Gly Ile
```

```
                65                  70                  75                  80
Gln Asp His Ala Leu Asp Leu Val Pro Arg Gly Ser Pro Gly Pro Arg
                        85                  90                  95

Gly Pro Arg Gly Pro Gln Gly Glu Gln Gly Pro Gln Gly Glu Arg Gly
                100                 105                 110

Phe Thr Gly Pro Gln Gly Pro Val Gly Pro Gln Gly Glu Gln Gly Pro
                115                 120                 125

Gln Gly Glu Arg Gly Phe Thr Gly Pro Gln Gly Pro Ile Gly Leu Gln
            130                 135                 140

Gly Glu Gln Gly Pro Gln Gly Glu Arg Gly Phe Thr Gly Pro Gln Gly
145                 150                 155                 160

Pro Val Gly Pro Gln Gly Glu Gln Gly Pro Gln Gly Glu Arg Gly Phe
                165                 170                 175

Thr Gly Pro Gln Gly Pro Val Gly Pro Gln Gly Glu Gln Gly Pro Gln
                180                 185                 190

Gly Glu Arg Gly Phe Thr Gly Pro Gln Gly Pro Ile Gly Pro Gln Gly
            195                 200                 205

Glu Gln Gly Pro Gln Gly Glu Arg Gly Phe Thr Gly Pro Gln Gly Pro
210                 215                 220

Ile Gly Pro Gln Gly Asn Gln Gly Pro Ile Gly Pro Gln Gly Glu Gln
225                 230                 235                 240

Gly Pro Gln Gly Ala Thr Gly Pro Gln Gly Pro Gln Gly Pro Val Gly
                245                 250                 255

Pro Gln Gly Asn Gln Gly Pro Ile Gly Pro Gln Gly Pro Val Gly Pro
                260                 265                 270

Gln Gly Pro Gln Gly Gln Pro Gly Val Asn Gly Pro Ser Gly Ala Glu
            275                 280                 285

Gly Pro Pro Gly Pro Gln Gly Leu Ala Gly Gln Arg Gly Ile Val Gly
        290                 295                 300

Leu Pro Gly Pro Arg Gly Pro Gln Gly Glu Gln Gly Pro Gln Gly Glu
305                 310                 315                 320

Arg Gly Phe Thr Gly Pro Gln Gly Pro Val Gly Pro Gln Gly Glu Gln
                325                 330                 335

Gly Pro Gln Gly Glu Arg Gly Phe Thr Gly Pro Gln Gly Pro Ile Gly
            340                 345                 350

Leu Gln Gly Glu Gln Gly Pro Gln Gly Glu Arg Gly Phe Thr Gly Pro
        355                 360                 365

Gln Gly Pro Val Gly Pro Gln Gly Glu Gln Gly Pro Gln Gly Glu Arg
            370                 375                 380

Gly Phe Thr Gly Pro Gln Gly Pro Val Gly Pro Gln Gly Glu Gln Gly
385                 390                 395                 400

Pro Gln Gly Glu Arg Gly Phe Thr Gly Pro Gln Gly Pro Ile Gly Pro
                405                 410                 415

Gln Gly Glu Gln Gly Pro Gln Gly Glu Arg Gly Phe Thr Gly Pro Gln
                420                 425                 430

Gly Pro Ile Gly Pro Gln Gly Asn Gln Gly Pro Ile Gly Pro Gln Gly
            435                 440                 445

Glu Gln Gly Pro Gln Gly Ala Thr Gly Pro Gln Gly Pro Gln Gly Pro
        450                 455                 460

Val Gly Pro Gln Gly Asn Gln Gly Pro Ile Gly Pro Gln Gly Pro Val
465                 470                 475                 480

Gly Pro Gln Gly Pro Gln Gly Gln Pro Gly Val Asn
                485                 490
```

<210> SEQ ID NO 44
<211> LENGTH: 339
<212> TYPE: PRT
<213> ORGANISM: Artificial Sequence
<220> FEATURE:
<223> OTHER INFORMATION: Reincombinant collagen like protein

<400> SEQUENCE: 44

```
Met Asn His Lys Val His Met His His His His His Asp Glu Gln
1               5                   10                  15

Glu Glu Lys Ala Lys Val Arg Thr Glu Leu Ile Gln Glu Leu Ala Gln
            20                  25                  30

Gly Leu Gly Gly Phe Glu Lys Lys Asn Phe Pro Thr Leu Gly Asp Glu
        35                  40                  45

Asp Leu Asp His Thr Tyr Met Thr Lys Leu Leu Thr Tyr Leu Gln Glu
    50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg Gly Ser Pro Gly Pro Ala
            85                  90                  95

Gly Pro Ala Gly Pro Gln Gly Pro Ala Gly Pro Ala Gly Ala Gln Gly
            100                 105                 110

Pro Ala Gly Pro Ala Gly Pro Gln Gly Pro Ala Gly Pro Gln Gly Ser
        115                 120                 125

Ala Gly Ala Gln Gly Pro Lys Gly Asp Thr Gly Ala Ala Gly Pro Ala
    130                 135                 140

Gly Glu Ala Gly Pro Lys Gly Glu Thr Gly Ala Ala Gly Pro Lys Gly
145                 150                 155                 160

Asp Thr Gly Ala Ala Gly Pro Ala Gly Pro Lys Gly Asp Thr Gly Ala
            165                 170                 175

Ala Gly Pro Ala Gly Pro Lys Gly Asp Thr Gly Ala Ala Gly Ala Thr
        180                 185                 190

Gly Pro Lys Gly Glu Lys Gly Glu Thr Gly Ala Ala Gly Pro Lys Gly
    195                 200                 205

Asp Lys Gly Glu Thr Gly Ala Ala Gly Pro Lys Gly Asp Lys Gly Glu
    210                 215                 220

Thr Gly Ala Ala Gly Pro Lys Gly Glu Lys Gly Glu Thr Gly Ala Val
225                 230                 235                 240

Gly Pro Lys Gly Asp Lys Gly Glu Thr Gly Ala Ala Gly Pro Lys Gly
            245                 250                 255

Asp Arg Gly Glu Thr Gly Ala Val Gly Pro Lys Gly Asp Lys Gly Glu
        260                 265                 270

Thr Gly Ala Val Gly Pro Lys Gly Asp Lys Gly Glu Thr Gly Ala Ile
    275                 280                 285

Gly Pro Lys Gly Asp Lys Gly Asp Lys Gly Asp Lys Gly Asp Ala Gly
    290                 295                 300

Val Ala Gly Pro Gln Gly Ile Gln Val Lys Gly Asp Thr Gly Leu
305                 310                 315                 320

Gln Gly Pro Lys Gly Asp Ala Pro Gln Gly Ala Pro Gly Thr Pro
            325                 330                 335

Gly Gly Gly
```

<210> SEQ ID NO 45
<211> LENGTH: 210

```
<212> TYPE: PRT
<213> ORGANISM: Artificial Sequence
<220> FEATURE:
<223> OTHER INFORMATION: Reincombinant collagen like protein

<400> SEQUENCE: 45

Met His His His His His Gly Arg Pro Gly Pro Gln Gly Pro Arg
1               5                   10                  15

Gly Arg Pro Gly Glu Pro Gly Arg Pro Gly Pro Gln Gly His Pro Gly
            20                  25                  30

Arg Pro Gly Pro Glu Gly Pro Arg Gly Lys Gln Gly Pro Val Gly Lys
            35                  40                  45

Pro Gly Pro Gln Gly Lys Ala Gly Pro Gln Gly Lys Pro Gly Ile Ala
    50                  55                  60

Gly Lys Pro Gly Pro Asp Gly Lys Pro Gly Pro Ile Gly Pro Gln Gly
65                  70                  75                  80

Lys Ala Gly Pro Gln Gly Pro Arg Gly Glu Gln Gly Leu Arg Gly Glu
                85                  90                  95

Gln Gly Pro Arg Gly Glu Gln Gly Pro Gln Gly Pro Arg Gly Glu Gln
            100                 105                 110

Gly Pro Arg Gly Glu Pro Gly Pro Ala Gly Ala Leu Pro Ser Ile Glu
            115                 120                 125

Gln Val Met Pro Trp Leu His Leu Ile Phe Asp Ala Tyr Glu Asp Tyr
130                 135                 140

Lys Ala Gln Arg Ala Arg Glu Ala Arg Glu Leu Glu Arg Leu Ala
145                 150                 155                 160

Ala Glu Ala Leu Glu Gln Ala Ala Arg Glu Ala Ala Glu Arg Glu Val
                165                 170                 175

Ala Ala Ala Ile Glu Ala Ala Asn Ala Glu Ala Glu Ile Met Leu Asp
            180                 185                 190

Asp Glu Thr His Ala Glu Gly Gly Lys Lys Lys Lys Arg Lys His
            195                 200                 205

Lys Asp
    210

<210> SEQ ID NO 46
<211> LENGTH: 136
<212> TYPE: PRT
<213> ORGANISM: Artificial Sequence
<220> FEATURE:
<223> OTHER INFORMATION: Reincombinant collagen like protein

<400> SEQUENCE: 46

Met His His His His His Gly Leu Pro Gly Pro Lys Gly Asp Pro
1               5                   10                  15

Gly Pro Gln Gly Pro Ala Gly Pro Lys Gly Glu Pro Gly Pro Lys Gly
            20                  25                  30

Glu Pro Gly Pro Lys Gly Glu Pro Gly Pro Lys Gly Glu Pro Gly Pro
            35                  40                  45

Lys Gly Glu Pro Gly Pro Lys Gly Glu Pro Gly Pro Lys Gly Glu Pro
    50                  55                  60

Gly Pro Lys Gly Glu Pro Gly Arg Gly Glu Ala Gly Pro Gln Gly
65                  70                  75                  80

Ala Leu Gly Pro Lys Gly Glu Ala Gly Ser Arg Gly Glu Pro Gly Pro
                85                  90                  95

Arg Gly Glu Pro Gly Pro Lys Gly Glu Ala Gly Leu Ala Gly Ala Pro
            100                 105                 110
```

Gly Pro Lys Gly Glu Ala Gly Pro Arg Gly Pro Gln Gly Glu Arg Gly
            115                 120                 125

Pro Pro Gly Ala Pro Gly Ala Ala
        130                 135

<210> SEQ ID NO 47
<211> LENGTH: 67
<212> TYPE: PRT
<213> ORGANISM: Streptococcus pyogenes

<400> SEQUENCE: 47

Glu Glu Asn Glu Lys Val Arg Glu Gln Glu Lys Leu Ile Gln Gln Leu
1               5                   10                  15

Ser Glu Lys Leu Val Glu Ile Asn Asp Leu Gln Thr Leu Asn Gly Asp
            20                  25                  30

Lys Glu Ser Ile Gln Ser Leu Val Asp Tyr Leu Thr Arg Arg Gly Lys
        35                  40                  45

Leu Glu Glu Glu Trp Met Glu Tyr Leu Asn Ser Gly Ile Gln Arg Lys
    50                  55                  60

Leu Phe Val
65

<210> SEQ ID NO 48
<211> LENGTH: 147
<212> TYPE: PRT
<213> ORGANISM: Bacillus cereus

<400> SEQUENCE: 48

Met Asn Asn Lys Asn Lys Gly Lys Val Phe Tyr Gly Asn Asp Cys Cys
1               5                   10                  15

Glu Val Arg Ala Cys Ser His Ile Asn Ile Ser Lys Ser Glu Leu Thr
            20                  25                  30

Glu Phe Val Arg Leu Leu Gln Ala Leu Gly Gln Ala Ile Gln Ala Val
        35                  40                  45

Phe Gln Asn Pro Ser Gln Asn Asn Ile Asp Asn Leu Ile Ala Ala Leu
    50                  55                  60

Asn Asn Leu Gln Lys Phe Leu Asn Cys Leu Asp Leu Ser Pro Ala Gln
65                  70                  75                  80

Arg Gln Ile Gly Asn Ser Ile Ile Ala Asn Leu Leu Thr Ile Leu Arg
                85                  90                  95

Thr Thr Pro Phe Ser Cys Gly Ala Leu Tyr Val Glu Leu Gln Ser Leu
            100                 105                 110

Leu Asn Tyr Leu Leu Tyr Ile Ala Lys Leu Phe Lys Val Asp Cys Cys
        115                 120                 125

Thr Thr Asp Lys Leu Val Lys Leu Ile Thr Glu Ile Gln Ala Ile Leu
    130                 135                 140

Val Gln Tyr
145

<210> SEQ ID NO 49
<211> LENGTH: 86
<212> TYPE: PRT
<213> ORGANISM: Rhodopseudomonas palustris tie-1

<400> SEQUENCE: 49

Pro Ser Ile Glu Gln Val Met Pro Trp Leu His Leu Ile Phe Asp Ala
1               5                   10                  15

```
Tyr Glu Asp Tyr Lys Ala Gln Arg Ala Arg Glu Ala Arg Glu Leu Glu
             20                  25                  30

Glu Arg Leu Ala Ala Glu Ala Leu Glu Gln Ala Ala Arg Glu Ala Ala
         35                  40                  45

Glu Arg Glu Val Ala Ala Ala Ile Glu Ala Ala Asn Ala Glu Ala Glu
     50                  55                  60

Ile Met Leu Asp Asp Glu Thr His Ala Glu Gly Gly Lys Lys Lys Lys
65                  70                  75                  80

Lys Arg Lys His Lys Asp
                85

<210> SEQ ID NO 50
<211> LENGTH: 15
<212> TYPE: PRT
<213> ORGANISM: Artificial Sequence
<220> FEATURE:
<223> OTHER INFORMATION: Non collagen natural break

<400> SEQUENCE: 50

Gly Pro Gly Glu Phe Tyr Phe Asp Leu Arg Leu Lys Gly Pro Gly
1               5                   10                  15

<210> SEQ ID NO 51
<211> LENGTH: 86
<212> TYPE: PRT
<213> ORGANISM: Rhodopseudomonas palustris tie-1

<400> SEQUENCE: 51

Pro Ser Ile Glu Gln Val Met Pro Trp Leu His Leu Ile Phe Asp Ala
1               5                   10                  15

Tyr Glu Asp Tyr Lys Ala Gln Arg Ala Arg Glu Ala Arg Glu Leu Glu
             20                  25                  30

Glu Arg Leu Ala Ala Glu Ala Leu Glu Gln Ala Ala Arg Glu Ala Ala
         35                  40                  45

Glu Arg Glu Val Ala Ala Ala Ile Glu Ala Ala Asn Ala Glu Ala Glu
     50                  55                  60

Ile Met Leu Asp Asp Glu Thr His Ala Glu Gly Gly Lys Lys Lys Lys
65                  70                  75                  80

Lys Arg Lys His Lys Asp
                85

<210> SEQ ID NO 52
<211> LENGTH: 27
<212> TYPE: PRT
<213> ORGANISM: Artificial Sequence
<220> FEATURE:
<223> OTHER INFORMATION: Forward Primer

<400> SEQUENCE: 52

Ala Gly Ala Ala Gly Cys Thr Cys Cys Ala Ala Thr Gly Gly Cys Ala
1               5                   10                  15

Ala Ala Gly Gly Ala Ala Gly Ala Thr Gly Ala
             20                  25

<210> SEQ ID NO 53
<211> LENGTH: 29
<212> TYPE: PRT
<213> ORGANISM: Artificial Sequence
<220> FEATURE:
<223> OTHER INFORMATION: Reverse Primer

<400> SEQUENCE: 53
```

-continued

Ala Cys Thr Cys Ala Thr Thr Cys Ala Ala Cys Thr Gly Gly Ala Gly
1               5                   10                  15

Gly Cys Gly Thr Ala Thr Gly Cys Ala Thr Thr Thr Cys
            20                  25

<210> SEQ ID NO 54
<211> LENGTH: 24
<212> TYPE: PRT
<213> ORGANISM: Artificial Sequence
<220> FEATURE:
<223> OTHER INFORMATION: Forward Primer

<400> SEQUENCE: 54

Thr Cys Cys Cys Gly Ala Thr Thr Gly Ala Gly Gly Cys Gly Ala Ala
1               5                   10                  15

Gly Cys Ala Ala Ala Cys Thr Thr
            20

<210> SEQ ID NO 55
<211> LENGTH: 24
<212> TYPE: PRT
<213> ORGANISM: Artificial Sequence
<220> FEATURE:
<223> OTHER INFORMATION: Reverse Primer

<400> SEQUENCE: 55

Thr Ala Cys Gly Cys Gly Ala Thr Gly Ala Cys Gly Cys Ala Thr Thr
1               5                   10                  15

Gly Ala Gly Gly Gly Ala Ala Ala
            20

<210> SEQ ID NO 56
<211> LENGTH: 24
<212> TYPE: PRT
<213> ORGANISM: Artificial Sequence
<220> FEATURE:
<223> OTHER INFORMATION: Forward Primer

<400> SEQUENCE: 56

Ala Ala Thr Cys Thr Cys Gly Ala Cys Cys Gly Cys Ala Ala Gly Gly
1               5                   10                  15

Ala Cys Cys Thr Cys Thr Ala Cys
            20

<210> SEQ ID NO 57
<211> LENGTH: 21
<212> TYPE: PRT
<213> ORGANISM: Artificial Sequence
<220> FEATURE:
<223> OTHER INFORMATION: Reverse Primer

<400> SEQUENCE: 57

Ala Cys Ala Thr Cys Cys Gly Cys Ala Ala Gly Gly Cys Gly Ala Ala
1               5                   10                  15

Gly Cys Ala Ala Thr
            20

<210> SEQ ID NO 58
<211> LENGTH: 24
<212> TYPE: PRT
<213> ORGANISM: Artificial Sequence
<220> FEATURE:
<223> OTHER INFORMATION: Forward Primer

<400> SEQUENCE: 58

Ala Ala Thr Thr Gly Ala Ala Gly Cys Cys Gly Thr Cys Ala Cys Gly
1               5                   10                  15

Cys Ala Ala Gly Cys Thr Cys Thr
            20

<210> SEQ ID NO 59
<211> LENGTH: 26
<212> TYPE: PRT
<213> ORGANISM: Artificial Sequence
<220> FEATURE:
<223> OTHER INFORMATION: Reverse Primer

<400> SEQUENCE: 59

Thr Gly Ala Cys Gly Gly Ala Ala Cys Ala Thr Cys Ala Ala Gly Ala
1               5                   10                  15

Cys Gly Cys Thr Gly Thr Thr Cys Ala Ala
            20                  25

<210> SEQ ID NO 60
<211> LENGTH: 24
<212> TYPE: PRT
<213> ORGANISM: Artificial Sequence
<220> FEATURE:
<223> OTHER INFORMATION: Forward Primer

<400> SEQUENCE: 60

Ala Ala Cys Thr Thr Thr Cys Cys Cys Gly Cys Cys Gly Thr Gly Thr
1               5                   10                  15

Thr Gly Thr Cys Cys Ala Ala Thr
            20

<210> SEQ ID NO 61
<211> LENGTH: 24
<212> TYPE: PRT
<213> ORGANISM: Artificial Sequence
<220> FEATURE:
<223> OTHER INFORMATION: Reverse Primer

<400> SEQUENCE: 61

Thr Gly Cys Ala Ala Gly Ala Ala Thr Thr Gly Thr Thr Gly Gly Gly
1               5                   10                  15

Cys Cys Ala Thr Gly Cys Gly Ala
            20

<210> SEQ ID NO 62
<211> LENGTH: 15
<212> TYPE: PRT
<213> ORGANISM: Artificial Sequence
<220> FEATURE:
<223> OTHER INFORMATION: MMP cleavage site

<400> SEQUENCE: 62

Gly Pro Gln Gly Ile Ala Gly Gln Arg Gly Val Val Gly Leu Pro
1               5                   10                  15

<210> SEQ ID NO 63
<211> LENGTH: 6
<212> TYPE: PRT
<213> ORGANISM: Methylobacterium sp. 4-46

<400> SEQUENCE: 63

Gly Pro Lys Gly Glu Pro
1               5

```
<210> SEQ ID NO 64
<211> LENGTH: 14
<212> TYPE: PRT
<213> ORGANISM: Solibacter Usitatus Ellin6076

<400> SEQUENCE: 64

Gly Pro Ala Gly Pro Ala Gly Pro Gln Gly Pro Ala Gly Pro
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Non collagen natural break

<400> SEQUENCE: 65

Gly Gln Ile Ser Glu Gln Lys Arg Pro Ile Asp Val Glu Phe Gln Lys
1               5                   10                  15

Gly

<210> SEQ ID NO 66
<211> LENGTH: 90
<212> TYPE: PRT
<213> ORGANISM: Streptococcus pyogenes

<400> SEQUENCE: 66

Met Asn His Lys Val His Met His His His His Asp Glu Gln
1               5                   10                  15

Glu Glu Lys Ala Lys Val Arg Thr Glu Leu Ile Gln Glu Leu Ala Gln
                20                  25                  30

Gly Leu Gly Gly Ile Glu Lys Lys Asn Phe Pro Thr Leu Gly Asp Glu
            35                  40                  45

Asp Leu Asp His Thr Tyr Met Thr Lys Leu Leu Thr Tyr Leu Gln Glu
        50                  55                  60

Arg Glu Gln Ala Glu Asn Ser Trp Arg Lys Arg Leu Leu Lys Gly Ile
65                  70                  75                  80

Gln Asp His Ala Leu Asp Leu Val Pro Arg
                85                  90

<210> SEQ ID NO 67
<211> LENGTH: 15
<212> TYPE: PRT
<213> ORGANISM: Artificial Sequence
<220> FEATURE:
<223> OTHER INFORMATION: MMP cleavage site

<400> SEQUENCE: 67

Gly Pro Gln Gly Leu Leu Gly Ala Pro Gly Ile Leu Gly Leu Pro
1               5                   10                  15

<210> SEQ ID NO 68
<211> LENGTH: 9
<212> TYPE: PRT
<213> ORGANISM: Artificial Sequence
<220> FEATURE:
<223> OTHER INFORMATION: MMP cleavage site

<400> SEQUENCE: 68

Gly Glu Gln Gly Pro Gln Gly Leu Pro
1               5
```

```
<210> SEQ ID NO 69
<211> LENGTH: 12
<212> TYPE: PRT
<213> ORGANISM: Artificial Sequence
<220> FEATURE:
<223> OTHER INFORMATION: MMP cleavage site

<400> SEQUENCE: 69

Gly Pro Gln Gly Leu Ala Gly Gln Arg Gly Ile Val
1               5                   10

<210> SEQ ID NO 70
<211> LENGTH: 35
<212> TYPE: PRT
<213> ORGANISM: Artificial Sequence
<220> FEATURE:
<223> OTHER INFORMATION: MMP cleavage site

<400> SEQUENCE: 70

Gly Ala Gln Gly Pro Pro Gly Ala Pro Gly Pro Leu Gly Ile Ala Gly
1               5                   10                  15

Ile Thr Gly Ala Arg Gly Leu Ala Gly Pro Pro Gly Met Pro Gly Pro
            20                  25                  30

Arg Gly Ser
        35

<210> SEQ ID NO 71
<211> LENGTH: 12
<212> TYPE: PRT
<213> ORGANISM: Artificial Sequence
<220> FEATURE:
<223> OTHER INFORMATION: MMP cleavage site

<400> SEQUENCE: 71

Gly Pro Leu Gly Ile Ala Gly Ile Thr Gly Ala Arg
1               5                   10

<210> SEQ ID NO 72
<211> LENGTH: 24
<212> TYPE: PRT
<213> ORGANISM: Artificial Sequence
<220> FEATURE:
<223> OTHER INFORMATION: MMP cleavage site

<400> SEQUENCE: 72

Gly Ala Gln Gly Pro Pro Gly Ala Pro Gly Pro Leu Gly Ile Ala Gly
1               5                   10                  15

Ile Thr Gly Ala Arg Gly Leu Ala
            20

<210> SEQ ID NO 73
<211> LENGTH: 33
<212> TYPE: PRT
<213> ORGANISM: Artificial Sequence
<220> FEATURE:
<223> OTHER INFORMATION: MMP cleavage site

<400> SEQUENCE: 73

Gly Pro Ser Gly Ala Glu Gly Pro Pro Gly Pro Gln Gly Leu Ala Gly
1               5                   10                  15

Gln Arg Gly Ile Val Gly Leu Pro Gly Gln Arg Gly Glu Arg Gly Phe
            20                  25                  30

Pro
```

<210> SEQ ID NO 74
<211> LENGTH: 12
<212> TYPE: PRT
<213> ORGANISM: Artificial Sequence
<220> FEATURE:
<223> OTHER INFORMATION: MMP cleavage site

<400> SEQUENCE: 74

Gly Pro Gln Gly Leu Ala Gly Gln Arg Gly Ile Val
1               5                   10

<210> SEQ ID NO 75
<211> LENGTH: 24
<212> TYPE: PRT
<213> ORGANISM: Artificial Sequence
<220> FEATURE:
<223> OTHER INFORMATION: MMP cleavage site

<400> SEQUENCE: 75

Gly Pro Ser Gly Ala Glu Gly Pro Pro Gly Pro Gln Gly Leu Ala Gly
1               5                   10                  15

Gln Arg Gly Ile Val Gly Leu Pro
            20

<210> SEQ ID NO 76
<211> LENGTH: 12
<212> TYPE: PRT
<213> ORGANISM: Streptococcus pyogenes

<400> SEQUENCE: 76

Gly Lys Asp Gly Lys Asp Gly Gln Pro Gly Lys Pro
1               5                   10

<210> SEQ ID NO 77
<211> LENGTH: 12
<212> TYPE: PRT
<213> ORGANISM: Streptococcus pyogenes

<400> SEQUENCE: 77

Gly Pro Arg Gly Glu Gln Gly Pro Thr Gly Pro Thr
1               5                   10

<210> SEQ ID NO 78
<211> LENGTH: 12
<212> TYPE: PRT
<213> ORGANISM: Artificial Sequence
<220> FEATURE:
<223> OTHER INFORMATION: DDR2 binding sequence

<400> SEQUENCE: 78

Gly Pro Arg Gly Gln Pro Gly Val Met Gly Phe Pro
1               5                   10

<210> SEQ ID NO 79
<211> LENGTH: 20
<212> TYPE: PRT
<213> ORGANISM: Clostridium perfringens

<400> SEQUENCE: 79

Gly Pro Arg Gly Pro Val Gly Pro Gln Gly Glu Gln Gly Pro Gln Gly
1               5                   10                  15

Glu Arg Gly

```
<210> SEQ ID NO 80
<211> LENGTH: 20
<212> TYPE: PRT
<213> ORGANISM: Clostridium perfringens

<400> SEQUENCE: 80

Gly Pro Arg Gly Pro Val Gly Leu Gln Gly Glu Gln Gly Pro Gln Gly
1               5                   10                  15

Glu Arg Gly Phe
            20

<210> SEQ ID NO 81
<211> LENGTH: 20
<212> TYPE: PRT
<213> ORGANISM: Clostridium perfringens

<400> SEQUENCE: 81

Gly Pro Arg Gly Pro Ile Gly Pro Gln Gly Glu Gln Gly Pro Gln Gly
1               5                   10                  15

Glu Arg Gly Phe
            20

<210> SEQ ID NO 82
<211> LENGTH: 20
<212> TYPE: PRT
<213> ORGANISM: Clostridium perfringens

<400> SEQUENCE: 82

Gly Pro Arg Gly Pro Ile Gly Leu Gln Gly Glu Gln Gly Pro Gln Gly
1               5                   10                  15

Glu Arg Gly Phe
            20

<210> SEQ ID NO 83
<211> LENGTH: 20
<212> TYPE: PRT
<213> ORGANISM: Clostridium perfringens

<400> SEQUENCE: 83

Gly Pro Arg Gly Pro Arg Gly Pro Gln Gly Glu Gln Gly Pro Gln Gly
1               5                   10                  15

Glu Arg Gly Phe
            20

<210> SEQ ID NO 84
<211> LENGTH: 20
<212> TYPE: PRT
<213> ORGANISM: Clostridium perfringens

<400> SEQUENCE: 84

Gly Pro Arg Gly Pro Arg Gly Leu Gln Gly Glu Gln Gly Pro Gln Gly
1               5                   10                  15

Glu Arg Gly Phe
            20

<210> SEQ ID NO 85
<211> LENGTH: 20
<212> TYPE: PRT
<213> ORGANISM: Clostridium perfringens

<400> SEQUENCE: 85

Gly Pro Gln Gly Pro Val Gly Pro Gln Gly Glu Gln Gly Pro Gln Gly
1               5                   10                  15
```

Glu Arg Gly Phe
        20

<210> SEQ ID NO 86
<211> LENGTH: 20
<212> TYPE: PRT
<213> ORGANISM: Clostridium perfringens

<400> SEQUENCE: 86

Gly Pro Gln Gly Pro Val Gly Leu Gln Gly Glu Gln Gly Pro Gln Gly
1               5                   10                  15

Glu Arg Gly Phe
        20

<210> SEQ ID NO 87
<211> LENGTH: 20
<212> TYPE: PRT
<213> ORGANISM: Clostridium perfringens

<400> SEQUENCE: 87

Gly Pro Gln Gly Pro Ile Gly Pro Gln Gly Glu Gln Gly Pro Gln Gly
1               5                   10                  15

Glu Arg Gly Phe
        20

<210> SEQ ID NO 88
<211> LENGTH: 20
<212> TYPE: PRT
<213> ORGANISM: Clostridium perfringens

<400> SEQUENCE: 88

Gly Pro Gln Gly Pro Ile Gly Leu Gln Gly Glu Gln Gly Pro Gln Gly
1               5                   10                  15

Glu Arg Gly Phe
        20

<210> SEQ ID NO 89
<211> LENGTH: 20
<212> TYPE: PRT
<213> ORGANISM: Clostridium perfringens

<400> SEQUENCE: 89

Gly Pro Gln Gly Pro Arg Gly Pro Gln Gly Glu Gln Gly Pro Gln Gly
1               5                   10                  15

Glu Arg Gly Phe
        20

<210> SEQ ID NO 90
<211> LENGTH: 20
<212> TYPE: PRT
<213> ORGANISM: Clostridium perfringens

<400> SEQUENCE: 90

Gly Pro Gln Gly Pro Arg Gly Leu Gln Gly Glu Gln Gly Pro Gln Gly
1               5                   10                  15

Glu Arg Gly Phe
        20

<210> SEQ ID NO 91
<211> LENGTH: 4
<212> TYPE: PRT
<213> ORGANISM: Artificial Sequence

```
<220> FEATURE:
<223> OTHER INFORMATION: MMP cleavage site

<400> SEQUENCE: 91

Gly Leu Tyr Gly
1

<210> SEQ ID NO 92
<211> LENGTH: 4
<212> TYPE: PRT
<213> ORGANISM: Artificial Sequence
<220> FEATURE:
<223> OTHER INFORMATION: MMP cleavage site

<400> SEQUENCE: 92

Gly Ile Tyr Gly
1
```